US012753212B2

(12) United States Patent
Mojzita et al.

(10) Patent No.: US 12,753,212 B2
(45) Date of Patent: Oct. 6, 2026

(54) NON-VIRAL TRANSCRIPTION ACTIVATION DOMAINS AND METHODS AND USES RELATED THERETO

(71) Applicant: Teknologian tutkimuskeskus VTT Oy, Espoo (FI)

(72) Inventors: Dominik Mojzita, Espoo (FI); Outi Koivistoinen, Espoo (FI); Astrid Salumäe, Espoo (FI)

(73) Assignee: Teknologian tutkimuskeskus VTT Oy, Espoo (FI)

(*) Notice: Subject to any disclaimer, the term of this patent is extended or adjusted under 35 U.S.C. 154(b) by 594 days.

(21) Appl. No.: 17/777,885

(22) PCT Filed: Nov. 18, 2020

(86) PCT No.: PCT/FI2020/050772
§ 371 (c)(1),
(2) Date: May 18, 2022

(87) PCT Pub. No.: WO2021/099685
PCT Pub. Date: May 27, 2021

(65) Prior Publication Data

US 2023/0111619 A1 Apr. 13, 2023

(30) Foreign Application Priority Data

Nov. 19, 2019 (FI) .................................... 20195988

(51) Int. Cl.
*C07K 14/415* (2006.01)
*C12N 15/80* (2006.01)
*C12N 15/81* (2006.01)

(52) U.S. Cl.
CPC ............ *C07K 14/415* (2013.01); *C12N 15/80* (2013.01); *C12N 15/815* (2013.01);
(Continued)

(58) Field of Classification Search
CPC ............. C07K 14/415; C07K 2319/02; C07K 2319/71; C07K 2319/80; C12N 15/80;
(Continued)

(56) References Cited

FOREIGN PATENT DOCUMENTS

| | | | |
|---|---|---|---|
| CN | 105949293 | A | 8/2019 |
| EP | 1151103 | B1 | 8/2004 |

(Continued)

OTHER PUBLICATIONS

Shuichi Yanagisawa, The Transcriptional Activation Domain of the Plant-Specific Dof1 Factor Functions in Plant, Animal, and Yeast Cells, Plant and Cell Physiology, vol. 42, Issue 8, Aug. 15, 2001, pp. 813-822, https://doi.org/10.1093/pcp/pce105 (Year: 2001).*

(Continued)

*Primary Examiner* — Robert B Mondesi
(74) *Attorney, Agent, or Firm* — Meunier Carlin & Curfman LLC

(57) ABSTRACT

The present invention relates to the fields of life sciences, genetics and regulation of gene expression. Specifically, the invention relates to a non-viral transcription activation domain for a eukaryotic host. Also, the present invention relates to a polypeptide or artificial transcription factor comprising the transcription activation domain of the present invention. And furthermore, the present invention relates to a polynucleotide, an expression cassette, expression system, and/or a eukaryotic host. Still, the present invention relates to a method for producing a desired protein product in the eukaryotic host of the present invention or to a method of preparing a non-viral transcription activation domain of the present invention or a polynucleotide encoding said non-viral transcription activation domain. And still further, the present invention relates to use of the transcription activation domain, polypeptide, artificial transcription factor, polynucleotide, expression cassette, expression system (Continued)

or eukaryotic host of the present invention for metabolic engineering and/or production of a desired protein product.

17 Claims, 6 Drawing Sheets

Specification includes a Sequence Listing.

(52) U.S. Cl.
CPC ...... *C07K 2319/02* (2013.01); *C07K 2319/71* (2013.01); *C07K 2319/80* (2013.01)

(58) Field of Classification Search
CPC ... C12N 15/815; C12N 15/8216; C12N 15/79
USPC .......................................................... 530/379
See application file for complete search history.

(56) References Cited

FOREIGN PATENT DOCUMENTS

| | | | |
|---|---|---|---|
| WO | 2009158591 | A1 | 12/2009 |
| WO | 20130116731 | A1 | 8/2013 |

OTHER PUBLICATIONS

Shuichi Yanagisawa, Jen Sheen, Involvement of Maize Dof Zinc Finger Proteins in Tissue-Specific and Light-Regulated Gene Expression, The Plant Cell, vol. 10, Issue 1, Jan. 1998, pp. 75-89, https://doi.org/10.1105/tpc.10.1.75 (Year: 1998).*
Sadowski MI, Jones DT. The sequence-structure relationship and protein function prediction. Curr Opin Struct Biol. Jun. 2009;19(3): 357-62. doi: 10.1016/j.sbi.2009.03.008. Epub May 4, 2009. PMID: 19406632. (Year: 2009).*
Seffernick JL, de Souza ML, Sadowsky MJ, Wackett LP. Melamine deaminase and atrazine chlorohydrolase: 98 percent identical but functionally different. J Bacteriol. Apr. 2001;183(8):2405-10. doi: 10.1128/JB.183.8.2405-2410.2001. PMID: 11274097; PMCID: PMC95154. (Year: 2001).*
Tang S, Edwards EA. Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318. PMID: 23479748; PMCID: PMC3638459. (Year: 2013).*
Yanagisawa S. The transcriptional activation domain of the plant-specific Dof1 factor functions in plant, animal, and yeast cells. Plant Cell Physiol. Aug. 2001;42(8):813-22. doi: 10.1093/pcp/pce105. PMID: 11522906. (Year: 2001).*
Duval M, Hsieh TF, Kim SY, Thomas TL. Molecular characterization of AtNAM: a member of the *Arabidopsis* NAC domain superfamily. Plant Mol Biol. Sep. 2002;50(2):237-48. doi: 10.1023/a:1016028530943. PMID: 12175016. (Year: 2002).*
UniProt Accession No. A0A078FSA1; Published Oct. 29, 2014 (Year: 2014).*
Chalhoub B, et al. Early allopolyploid evolution in the post-Neolithic *Brassica napus* oilseed genome. Science. Aug. 22, 2014;345(6199):950-3. doi: 10.1126/science.1253435. Epub Aug. 21, 2014. PMID: 25146293. (Year: 2014).*
Chavez A et al. (2015). "Highly efficient Cas9-mediated transcriptional programming." Nat Methods, 12(4), 326-328.
Lu, Y. et al. (2016). "High-level expression of improved thermostable alkaline xylanase variant in Pichia Pastoris through codon optimization, multiple gene insertion and high-density fermentation." Scientific Reports vol. 6, Article No. 37869.
Olsen, A. N., H. A. Ernst, et al. (2005). "NAC transcription factors: structurally distinct, functionally diverse." Trends Plant Sci 10(2): 79-87.
Zhang, J. et al. (2016). "Site-directed mutagenesis and thermal stability analysis of phytase from *Escherichia coli.*" Biosci. Biotech. Res. Comm. 9(3): 357-365.
Jianquan Li et al: "Activation domains for controlling plant gene expression using designed transcription factors", Plant Biotechnology Journal, vol. 11, No. 6, Mar. 22, 2013 (Mar. 22, 2013)—pp. 671-680, XP055543759.
Gita Naseri et al: Plant-Derived Transcription Factors for Orthologous Regulation of Gene Expression in the Yeast *Saccharomyces cerevisiae,* ACS Synthetic Biology, vol. 6, No. 9, Jun. 9, 2017 (Jun. 9, 2017), pp. 1742-1756, XP055768362.
Yanagisawa S: The Transcriptional Activation Domain of the Plant-Specific DOFI Factor Functions in Plant, Animal, and Yeast Cells11, Plant and Cell Physiology, Oxford University Press, UK, vol. 42, No. 8, Aug. 1, 2001 (Aug. 1, 2001). pp. 813-822, XP008046200.
Cho S et al: Analysis of the C-Terminal Region of *Arabidopsis thaliana* Apetalai as a Transcription Activation Domain11, Plant Molecular Biology, Springer, Dordrecht, NL, vol. 40, Jan. 1, 1999 (Jan. 1, 1999), pp. 419-429, XP002931726.
Shiv B. Tiwari et al: The EDLL motif: a potent plant transcriptional activation domain from AP2/ERF transcription factors, The Plant Journal, vol. 70, No. 5, Mar. 12, 2012 (Mar. 12, 2012), pp. 855-865, XP055348017.
Jed A. Christianson et al: The Low-Oxygen-Induced NAC Domain Transcription Factor ANAC102 Affects Viability of *Arabidopsis* Seeds following Low-Oxygen Treatment, Plant Physiology, vol. 149, No. 4, Jan. 28, 2009 (Jan. 28, 2009), pp. 1724-1738, XP055768009.
Anssi Rantasalo et al: A universal gene expression system for fungi Nucleic Acids Research, vol. 46, No. 18, Jun. 19, 2018 (Jun. 19, 2018), pp. elll-elll, XP055674339.
Database UniProt [Online] Nov. 2015 (Nov. 11, 2015), RecName: Full=NAC domain-containing protein {EC0:0000259:PROSITE:PS51005}; XP55767881, retrieved from EBI accession No. UNIPROT:A0AOK9QZX0 Database accession No. AOAOK9QZX0 the whole document.
Pattanaik S et al.: Directed evolution of plant basic helix-loop-helix transcription factors for the improvement of transactivational properties11, Biochimica Et Biophysica Acta. Gene Structure and Expression, Elsevier, Amsterdam, NL, vol. 1759, No. 6, Jun. 1, 2006 (Jun. 1, 2006), pp. 308-318, XP027896519.
Sainz MB et al: Extensive mutagenesis of a transcriptional activation domain identifies single hydrophobic and acidic amino acids important for activation in vivo., Molecular and Cellular Biology, vol. 17 , No. 1, Jan. 1, 1997 (Jan. 1, 1997), pp. 115-122, XP055803778.
Staller Max V. et al: 11A High-Throughput Mutational Scan of an Intrinsically Disordered Acidic Transcriptional Activation Domain11, Cell Systems, vol. 6, No. 4, Apr. 25, 2018 (Apr. 25, 2018), pp. 444-455.e6, XP055803792.
L. Warfield et al: A sequence-specific transcription activator motif and powerful synthetic variants that bind Mediator using a fuzzy protein interface, Proceedings of the National Academy of Sciences, vol. 111, No. 34, Aug. 13, 2014 (Aug. 13, 2014), pp. E3506-E3513, XP055767832.
Ko, JH. et al. ANAC012, a member of the plant-specific NAC transcription factor family, negatively regulates xylary fiber development in *Arabidopsis thaliana.* In: The Plant Journal 2007, vol. 50, No. 6, pp. 1035-1048.
International Search Report and Written Opinion, in connection with International Application No. PCT/FI2020/050772, dated May 25, 2021.
English translation of an Office Action in corresponding application CN2020800935991. Dated on Feb. 4, 2024.
Gene Bank Accession XP_021863783. NAC domain-containing protein 2-like (Spinacial oleracea). Jun. 6, 2023.
Benuck ML et al, "Mutations that increase acidity enhance the transcriptional activity of the glutamine-rich activation domain in stage-specific activator protein", Journal of Biological Chemistry, 274(36), pp. 25419-25425, DOI: 10.1074/jbc.274.36.25419, Sep. 3, 1999 (Mar. 9, 1999).
Office Action of corresponding Application No. 3,161,146, dated Feb. 20, 2025 (8 pages).
Wang, B et al. Identification and characterization of plant-specific NAC gene family in canola (Brassica napus L.) reveal novel members involved in cell death. Plant Molecular Biology. vol. 87. Nos. 4-5. pp. 395-411. 2015.

(56) References Cited

OTHER PUBLICATIONS

Supplementary files to: Wang, B et al. Identification and characterization of plant-specific NAC gene family in canola (Brassica napus L.) reveal novel members involved in cell death. Plant Molecular Biology. vol. 87. Nos. 4-5. pp. 395-411. 2015.
Office Action issued in corresponding South Korean Patent Application No. 10-2022-7017955 on Aug. 26, 2026.

* cited by examiner

NON-VIRAL TRANSCRIPTION ACTIVATION DOMAINS AND METHODS AND USES RELATED THERETO

CROSS REFERENCE TO RELATED APPLICATIONS

This application is a United States National Phase Patent Application of International Patent Application Number PCT/FI2020/050772, filed on Nov. 18, 2020, which claims the benefit of priority to Finnish National Patent Application number FI 20195988, filed on Oct. 19, 2019, both of which are incorporated by reference herein in their entireties.

FIELD OF THE INVENTION

The present invention relates to the fields of life sciences, genetics and regulation of gene expression. Specifically, the invention relates to a non-viral transcription activation domain for a eukaryotic host. Also, the present invention relates to a polypeptide or artificial transcription factor comprising the transcription activation domain of the present invention. And furthermore, the present invention relates to a polynucleotide, an expression cassette, expression system, and/or a eukaryotic host. Still, the present invention relates to a method for producing a desired protein product in the eukaryotic host of the present invention or to a method of preparing a non-viral transcription activation domain of the present invention or a polynucleotide encoding said non-viral transcription activation domain. And still further, the present invention relates to use of the transcription activation domain, polypeptide, artificial transcription factor, polynucleotide, expression cassette, expression system or eukaryotic host of the present invention for metabolic engineering and/or production of a desired protein product.

BACKGROUND OF THE INVENTION

Controlled and predictable gene expression is very difficult to achieve even in well-established hosts, especially in terms of stable expression in diverse cultivation conditions or stages of growth. In addition, for many potentially interesting industrial hosts, there is a very limited (or even absent) spectrum of tools and/or methods to accomplish expression of heterologous genes or to control expression of endogenous genes. In many instances, this prohibits the use of said interesting industrial hosts (often very promising hosts) in industrial applications.

Transcription factors greatly influence the regulation of gene expression. Usually there are at least two domains in transcription factors. DNA binding domains (DBD) bind promoters of target genes and activation domains (AD) participate in activating the transcription by interacting with the transcriptional machinery. There have been numerous previous attempts to introduce new transcription factors or domains thereof suitable for robust control of gene expression in engineered bio-logical systems.

In artificial gene expression systems, the use of virus-derived transcription activation domains (e.g. VP16 or VP64) is currently the most common solution for high-level expression. Also, other components derived from viruses or cancer-development-associated proteins may be used in efficient artificial expression systems. For example, Chavez A et al. describe an improved transcriptional regulator obtained through the rational design of a tripartite activator, VP64-p65-Rta (VPR) fused to nuclease-null Cas9, where the VP64 is derived from human herpes simplex virus, p65 is a human protein associated with multiple types of cancer, and Rta is derived from the Epstein-Barr virus (Chavez A et al. 2015, Nat Methods, 12(4), 326-328).

Use of plant (*Arabidopsis thaliana*) native transcription factors for regulation of gene expression in yeast have been described by Naseri G et al. (2017, ACS Synthetic Biology, 6, 1742-1756). In that study, Naseri G et al., focused on use of fusion transcription factors containing additional activation domains in their structure, especially the virus-based VP16 activation domain, the GAL4-activation domain of *Saccharomyces cerevisiae* origin, and the EDLL motif of *Arabidopsis thaliana* origin.

While the expression systems containing viral or cancer associated transcription activation domains are highly efficient, their use in many biotechnological applications, especially in food or medicine production, might be problematic due to the current regulations and customer and/or patient acceptance. There is, therefore, a need for novel transcription activation domains, which would replace the currently used virus-based domains. Furthermore, the new types of activation domains must provide sufficient level of functionality in the gene expression systems to achieve similar or better production of the target compounds. In addition, the efficient non-viral transcription activation domains, and gene expression systems based on them, should provide robust and stable gene expression in several different species and genera of production organisms.

BRIEF DESCRIPTION OF THE INVENTION

The objects of the invention, namely novel efficient transcription activation domains and tools and methods related thereto, can be used for functionally replacing the virus-based activation domains without compromising the performance of the gene expression system. The expression systems, containing the novel transcription activation domains, will provide robust and stable expression, a broad spectrum of expression levels, and can be used in several different species and genera. This is achieved by utilizing transcription activation domains derived from transcription factors found in plant species, e.g. in the species of edible plants.

Indeed, it has now been surprisingly found that modifications of plant derived transcription activation domains rendered novel activation domains, which are highly active, and, importantly, retain high activity in diverse eukaryotic organisms. These novel activation domains are non-viral transcription activation domains originating from plants that can be used for regulation of gene expression in an expression system e.g. in eukaryotes.

With the present invention defects of the prior art including but not limited to use of viral DNA-elements in an artificial expression system, can be overcome. The prior art lacks efficient activation domains and expression systems, which are functional across diverse species and at the same time are acceptable or suitable for all technological fields and industries utilizing gene expression including food and pharma.

Surprisingly, the inventors were able to develop specific activation domains originating from plants species. Said activation domains can be used in diverse expression systems as such, e.g. replacing the current activation domains used. Indeed, the activation domains of the present invention can be incorporated into expression systems based on the artificial (synthetic) transcription factors, without compromising the function of said systems; all previously demonstrated benefits of the artificial transcription systems can be retained or improved.

The present invention enables e.g. efficient transfer to and testing of engineered metabolic pathways simultaneously in several potential production hosts for functionality evaluation. Furthermore, the present invention provides tools for an orthogonal gene expression thus providing benefits to the scientific community stud-ying e.g. eukaryotic organisms.

Furthermore, the present invention allows broadening the use of artificial expression systems in applications, where the use of potentially problematic (viral) DNA elements is not welcome.

The present invention relates to a non-viral transcription activation domain for a eukaryotic host or for an artificial expression system in a eukaryotic host, wherein said transcription activation domain originates from a plant or from a plant transcription factor, e.g. from an edible plant or found in an edible plant.

Also, the present invention relates to a polypeptide comprising a non-viral transcription activation domain for a eukaryotic host or for an artificial expression system in a eukaryotic host, wherein said transcription activation domain originates from a plant or from a plant transcription factor.

Also, the present invention relates to an artificial transcription factor, wherein said artificial transcription factor comprises a non-viral transcription activation domain for a eukaryotic host or for an artificial expression system in a eukaryotic host, a DNA-binding domain and a nuclear localization signal, wherein said transcription activation domain originates from a plant or from a plant transcription factor. Still, the present invention relates to a polynucleotide encoding the transcription activation domain, polypeptide or artificial transcription factor of the present invention.

And still, the present invention relates to an expression cassette or expression system, wherein said expression cassette or expression system comprises the polynucleotide encoding the transcription activation domain, polypeptide or artificial transcription factor of the present invention.

Still furthermore, the present invention relates to a eukaryotic host comprising the transcription activation domain, polypeptide, artificial transcription factor, polynucleotide, expression cassette or expression system of the present invention.

Still furthermore, the present invention relates to a method for producing a desired protein product in a eukaryotic host comprising cultivating the host of the present invention under suitable cultivation conditions.

And still furthermore, the present invention relates to use of the transcription activation domain, polypeptide, artificial transcription factor, polynucleotide, expression cassette, expression system or eukaryotic host of the present invention for metabolic engineering and/or production of a desired protein product.

And still furthermore, the present invention relates to a method of preparing a non-viral transcription activation domain of the present invention or a polynucleotide encoding said non-viral transcription activation domain, wherein said method comprises obtaining a transcription activation domain polypeptide originating from a plant transcription factor or obtaining a polynucleotide encoding said transcription activation domain polypeptide originating from a plant transcription factor, and modifying the obtained transcription activation domain polypeptide or polynucleotide.

Other objects, details and advantages of the present invention will become apparent from the following drawings, detailed description and examples.

BRIEF DESCRIPTION OF THE DRAWINGS

FIG. 1 illustrates an example of a scheme of an expression system for testing transcription activation domains, and production of protein product of interest, in a eukaryotic organism or microorganism, exemplified on the assessment of production of e.g. red fluorescent protein, mCherry, e.g. in *Trichoderma reesei* (Example 1 and Example 8). Thus, the scheme also illustrates an expression system used for heterologous protein production e.g. in *Trichoderma reesei* (Example 3), *Myceliophthora thermophila* (Example 5), and/or *Aspergillus oryzae* (Example 7). The expression system is constructed as a single DNA molecule, and it comprises or is composed of a target gene expression cassette, a sTF expression cassette, selection marker (SM) expression cassette, and genome integration DNA regions (flanks), here exemplified by genomic DNA sequences from *Trichoderma reesei* located upstream of the egl1 gene (EGL1-5') and downstream of the egl1 gene (EGL1-3'). In one embodiment FIG. 1 shows a synthetic expression system used for filamentous fungi—e.g. *T. reesei, M. thermophila*, and/or *Aspergillus oryzae.*

The target gene expression cassette can comprise or comprises multiple sTF-specific binding sites, here exemplified by eight sTF-specific binding sites (8 BS) positioned upstream of a core promoter, here exemplified by An_201cp (SEQ ID NO: 23) of *Aspergillus niger* origin. The eight sTF-binding sites and the core promoter form a synthetic promoter, which strongly activates the transcription of a target gene, in presence of synthetic transcription factor (sTF). The target gene could be any DNA sequence encoding a protein product of interest, here exemplified by mCherry-encoding DNA sequence (see Example 1, Example 2, and Example 8), or exemplified by a xylanase enzyme-encoding DNA sequence (see Example 3 and Example 5), or exemplified by a bovine β-lactoblobulin B-encoding DNA sequence (see Example 7). The transcription of the target gene can be terminated on the terminator sequence, here exemplified by the *Trichoderma reesei* pdc1 terminator (Tr_PDC1t).

The synthetic transcription factor (sTF) expression cassette contains a core promoter (Tr_hfb2cp; SEQ ID NO: 25), a sTF coding sequence, and a terminator. The core promoter provides constitutive low expression of the sTF. The sTF binds to the sTF-dependent synthetic promoter in the target gene expression cassette facilitating its transcription. The sTF comprises or is composed of a DNA-binding-domain (BDB), which consists of bacterial DNA binding protein and nuclear localization signal, such as the SV40 NLS, and the transcription activation domain (AD). The AD is any transcription activation domain of plant origin, here exemplified by ten examples based on or originating from transcription factors found in *Arabidopsis thaliana, Brassica napus*, and *Spinacia oleracea*. The control AD is VP16 of herpes simplex virus origin. The transcription of the sTF gene can be terminated on the terminator sequence, here exemplified by the *Trichoderma reesei* tef1 terminator (Tr_TEF1t).

The selection marker (SM) expression cassette is any expression cassette allowing production of a specific protein in a host organism, which provides to the host organism means to grown under selection conditions, such as in presence of an antibiotic compound or an absence of essential metabolite. The SM cassette is exemplified here by the expression cassette allowing expression of the pyr4 gene (encoding orotidine 5'-phosphate decarboxylase enzyme) in *Trichoderma reesei* strain (Example 1, Example 3, and Example 8), or allowing expression of the hygR gene (encoding Hygromycin-B 4-O-kinase) in *Myceliophthora thermophila* (Example 5), or allowing expression of the pyrG gene (encoding orotidine 5'-phosphate decarboxylase enzyme) in *Aspergillus oryzae* strain (Example 7).

Figure 2:
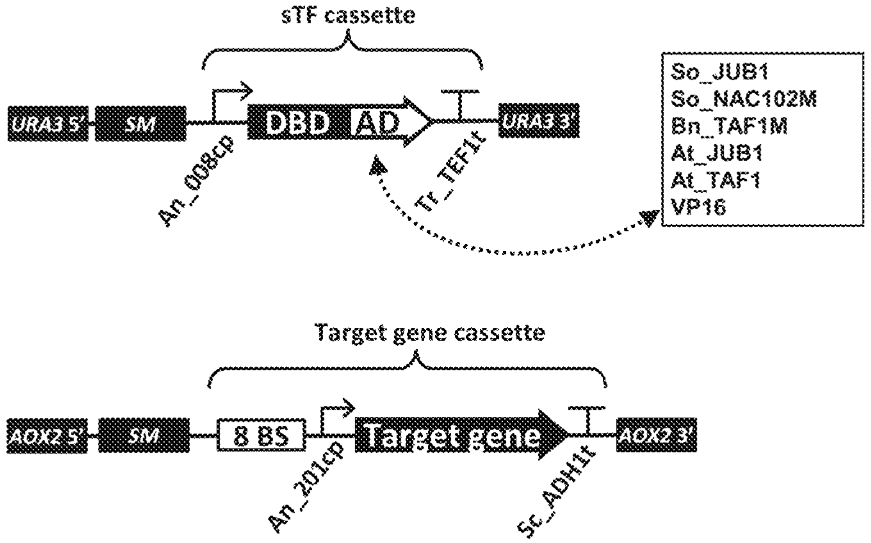

FIG. 2 illustrates an example of a scheme of an expression system comprising a transcription activation domain of the present invention. Indeed, FIG. 2 illustrates an example of a scheme of an expression system for testing transcription activation domains, and production of a protein product of interest, in a eukaryotic organism or microorganism, exemplified on the assessment of production of heterologous protein, e.g. phytase enzyme of bacterial origin, e.g. in *Pichia pastoris* (Example 4). The expression system can comprise or is constructed as two separate DNA molecules; the first DNA comprising or is composed of a sTF expression cassette, a selection marker (SM) expression cassette, and genome integration DNA regions (flanks); and the second DNA comprising or is composed of a target gene expression cassette, selection marker (SM) expression cassette, and genome integration DNA regions (flanks). Each cassette is integrated into separate locus of the host genome, together forming a functional gene expression system. In one embodiment FIG. 2 shows a synthetic expression system used for *Pichia pastoris.*

Figure 4:
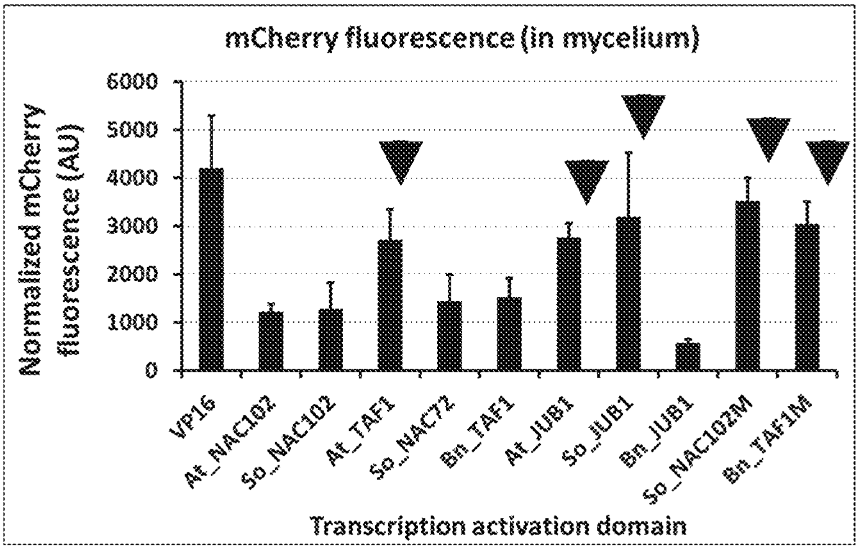

The sTF expression cassette can comprise (or consists of) a core promoter (An_008cp SEQ ID NO: 22), a sTF coding sequence, and a terminator. The sTF comprises (or consists of) DNA-binding-domain (BDB), which consists of bacterial DNA binding protein, here exemplified by the Bm3R1 repressor (Example 4), and nuclear localization signal, such as the SV40 NLS, and the transcription activation domain (AD). The AD is any transcription activation domain of plant origin, here exemplified by five examples based on or originating from transcription factors found in *Arabidopsis thaliana, Brassica napus*, and *Spinacia oleracea* selected based on the analysis performed in Example 1 (FIG. 4). The control AD can be e.g. VP16 of herpes simplex virus origin. The transcription of the sTF gene can be terminated on the terminator sequence, here exemplified by the *Trichoderma reesei* tef1 terminator (Tr_TEF1t). The SM cassette is exemplified here by the expression cassette allowing expression of the kanR gene (encoding aminoglycoside phosphotransferase enzyme) in *Pichia pastoris* strain (Example 4). The genome integration DNA regions (flanks), here exemplified by genomic DNA sequences from *Pichia pastoris* located upstream of the URA3 gene (URA3-5') and downstream of the URA3 gene (URA3-3').

The target gene expression cassette can comprise or comprises multiple sTF-specific binding sites, here exemplified by eight Bm3R1-specific binding sites (8 BS) positioned upstream of a core promoter, here exemplified by An_201cp (SEQ ID NO: 23) of *Aspergillus niger* origin. The target gene could be any DNA sequence encoding a protein product of interest, here exemplified by a phytase enzyme-encoding DNA sequence (see Example 4). The transcription of the target gene can be terminated on the terminator sequence, here exemplified by the *Saccharomyces cerevisiae* ADH1 terminator (Sc_ADH1t). The SM cassette is exemplified here by the expression cassette allowing expression of the *Pichia pastoris* URA3 gene (encoding orotidine 5'-phosphate decarboxylase enzyme) in *Pichia pastoris* (Example 4). The genome integration DNA regions (flanks) are exemplified here by genomic DNA sequences from *Pichia pastoris* located upstream of the AOX2 gene (AOX2-5') and downstream of the AOX2 gene (AOX2-3').

Figure 3:
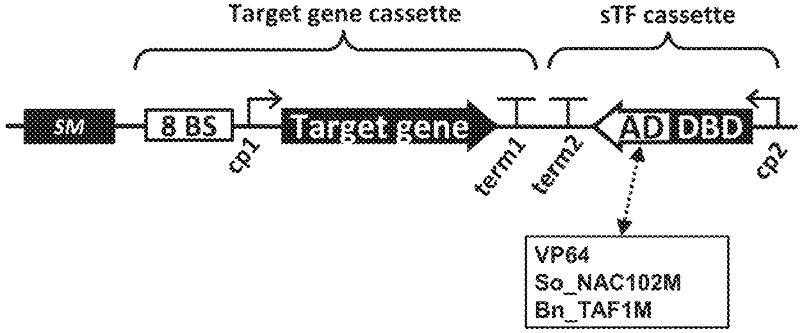

FIG. 3 illustrates an example of a scheme of an expression system comprising a transcription activation domain of the present invention. Indeed, FIG. 3 illustrates an example of a scheme of an expression system for testing transcription activation domains, and production of protein product of interest, in a eukaryotic organism or microorganism, exemplified on the assessment of production of e.g. red fluorescent protein, mCherry, e.g. in CHO cells (*Cricetulus griseus*) (Example 6). The expression system is constructed as a single DNA molecule, and it comprises or is composed of a target gene expression cassette, a sTF expression cassette, and a selection marker (SM) expression cassette. More specifically FIG. 3 shows a synthetic expression system used for CHO cells.

The target gene expression cassette can comprise or comprises multiple sTF-specific binding sites, here exemplified by eight sTF-specific binding sites (8 BS) positioned upstream of a core promoter (CP1), here exemplified by any of Mm_Atp5Bcp (SEQ ID NO: 26), or Mm_Eef2cp (SEQ ID NO: 27), or Mm_Rpl4cp (SEQ ID NO: 28) of *Mus musculus* origin. The target gene could be any DNA sequence encoding a protein product of interest, here exemplified by mCherry-encoding DNA sequence (see Example 6). The transcription of the target gene can be terminated on the terminator sequence (term1), here exemplified by any of SV40 terminator of simian virus 40 origin, or FTH1 terminator of *Mus musculus* origin (Table 1F; sequences shown in italics with grey highlight).

The sTF expression cassette can comprise a core promoter (CP2), a sTF coding sequence, and a terminator. The CP2 is exemplified here by any of Mm_Atp5Bcp (SEQ ID NO: 26), or Mm_Eef2cp (SEQ ID NO: 27), or Mm_Rpl4cp (SEQ ID NO: 28) of *Mus musculus* origin (Example 6). The sTF comprises or is composed of a DNA-binding-domain (BDB), which comprises or consists of bacterial DNA binding protein, exemplified here by the PhlF repressor of *Pseudomonas protegens* origin, or exemplified by the McbR repressor of *Corynebacterium* sp. origin (Example 6), and nuclear localization signal, such as the SV40 NLS, and the transcription activation domain (AD). The AD is any transcription activation domain of plant origin, here exemplified by two examples (So-NAC102M—SEQ ID NO: 10, and Bn-TAF1M—SEQ ID NO: 11) based on transcription factors found in *Brassica napus*, and *Spinacia oleracea*, which were selected based on the analysis performed in fungal hosts (Example 3, Example 4, Example 5). The control AD is VP64 of herpes simplex virus origin (SEQ ID NO: 30). The transcription of the sTF gene can be terminated on the terminator sequence (term2), here exemplified by any of SV40 terminator of simian virus 40 origin, or FTH1 terminator of *Mus musculus* origin (Table 1F; sequences shown in italics with grey highlight). The SM cassette is exemplified here by the expression cassette allowing expression of the pac gene (encoding puromycin N-acetyltransferase enzyme) in CHO cells (Example 6).

Figure 1:
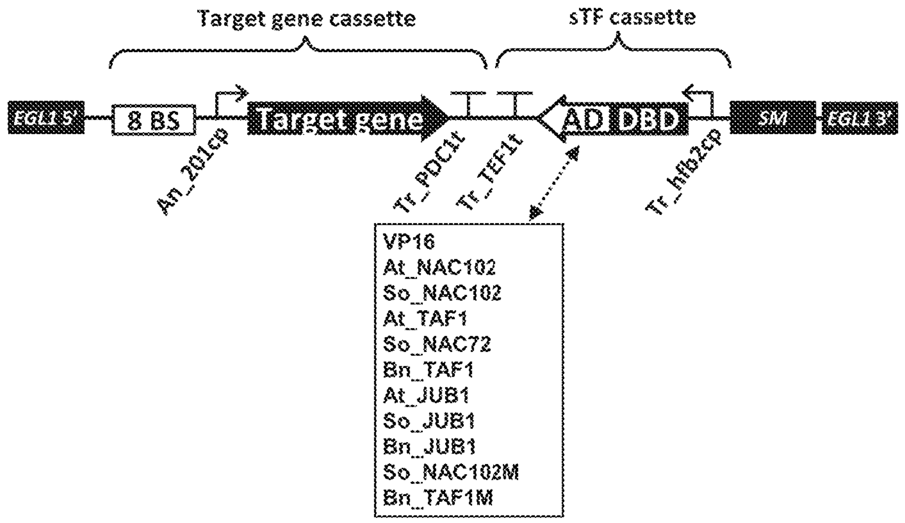
FIG. 1 illustrates an example of a scheme of an expression system comprising a transcription activation domain of the present invention. Indeed.

FIG. 4 depicts an example of the analysis of red fluorescent protein, mCherry, expressed in *Trichoderma reesei* strains transformed with the expression systems shown in FIG. 1. The aim of the experiment was to assess the performance of the plant-based transcription activation domains in comparison with the viral-based VP16 activation domain (Example 1, Example 2). A set of eleven *T. reesei* strains, each containing an expression system with an indicated AD integrated in the genome in the egl1 locus (egl1 gene replaced by the expression system), were cultivated for 24 hours in YE-glucose medium prior to the analysis. Quantitative analysis was performed by fluorometry measurement of mycelia suspensions using the VARIOSKAN® instrument (Thermo Electron Corporation). The graphs show fluorescence intensity (mCherry) normalized by the optical density of the mycelium suspensions used for the fluorometric analysis. The columns represent average values and the error bars standard deviations from at least three experimental replicates. Five activation domains (marked with arrow in the graph) were selected for additional testing.

Figure 5:
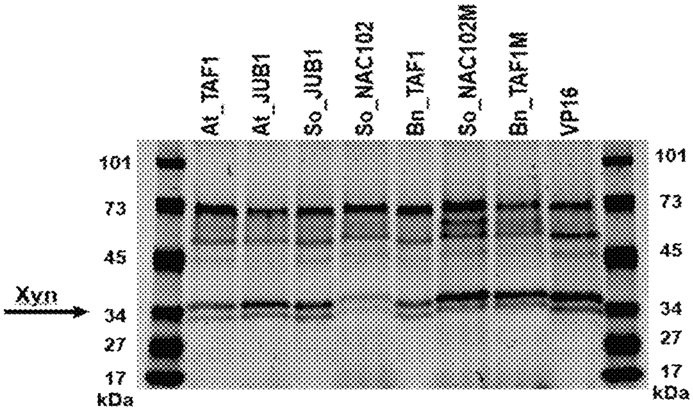

FIG. 5 depicts SDS-PAGE analysis (Coomassie stain gel) of xylanase protein (Xyn) produced by *Trichoderma reesei* strains with use of the expression systems containing diverse transcription activation domains (24 well plate, see Example 3). A set of eight *T. reesei* strains, each containing an expression system with an indicated AD, integrated in the genome in the egl1 locus (egl1 gene replaced by the expression system), were cultivated for 3 days in 4 mL of the YE-glc medium prior to the analysis. Equivalent of 10 μL of the culture supernatant from each culture was loaded on a gel (4-20% gradient) and the proteins were separated in an electric field (PowerPac HC; BioRad). The gel was stained with colloidal coomassie (PageBlue Protein Staining Solution; THERMO FISHER SCIENTIFIC®), and the visualization was performed on the ODYSSEY® CLx Imaging System instrument (LI-COR® Biosciences). The xylanase protein (Xyn) is indicated by an arrow. Three strains were selected for bioreactor cultivations; the strain with expression systems containing So-NAC102M (SEQ ID NO: 10) and Bn-TAF1M (SEQ ID NO: 11) activation domains, and the control strain with the VP16 AD (SEQ ID NO: 1).

Figure 6:
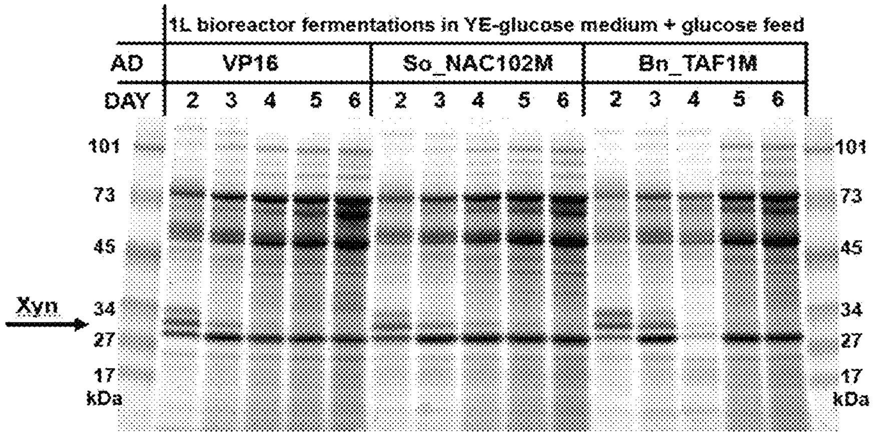

FIG. 6 depicts SDS-PAGE analysis (Coomassie stain gel) of xylanase protein (Xyn) produced by *Trichoderma reesei* strains in 1 L bioreactors (see Example 3). A set of three *T. reesei* strains were cultivated for 6 days in the YE-glucose medium with continuous glucose feeding. Equivalent of 2 μL of different time-points culture supernatants from each culture was loaded on a gel (4-20% gradient) and the proteins were separated in in an electric field (PowerPac HC; BioRad). The gel was stained with colloidal coomassie (PageBlue Protein Staining Solution; THERMO FISHER SCIENTIFIC®), and the visualization was performed on the ODYSSEY® CLx Imaging System instrument (LI-COR® Biosciences). The xylanase protein (Xyn) is indicated by an arrow. The cultures from time-points day 5 and day 6 were analyzed for specific xylanase activity (FIG. 7).

Figure 7:
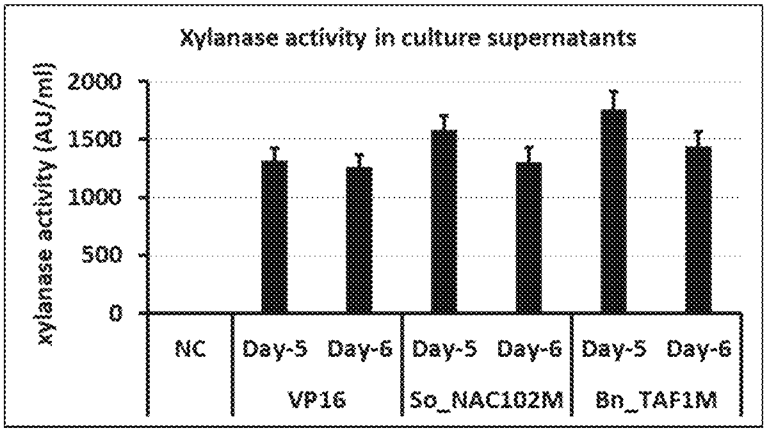

FIG. 7 depicts the xylanase activity analysis in culture supernatants of *Trichoderma reesei* strains cultivated in 1 L bioreactors (see Example 3). The culture supernatants from day 5 and day 6—diluted in 50 mM Tris·HCl (pH 8.0)—were assayed for the xylanase activity by EnzCheck® Ultra Xylanase Assay Kit (INVITROGEN®). The activity is expressed in arbitrary units per mL of the culture supernatant (AU/mL). The negative control (NC) represents a culture supernatant of 1 L bioreactor cultivation (day 6) of *Trichoderma reesei* strain not producing the xylanase. The columns represent average values and the error bars standard deviations from at least three technical replicates.

Figure 8:
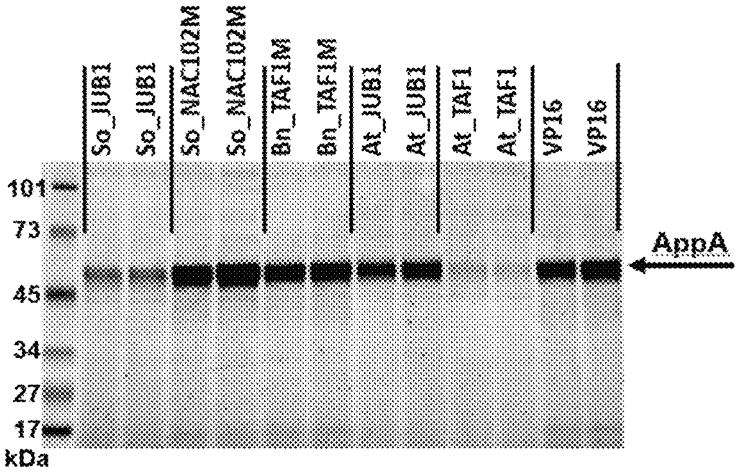

FIG. 8 shows SDS-PAGE analysis (Coomassie stain gel) of phytase protein (Appa) produced by *Pichia pastoris* strains with use of the expression systems containing diverse transcription activation domains (24 well plate, FIG. 2, Example 4). A set of five *P. pastoris* strains were cultivated in duplicates for 3 days in 4 mL of the BMG-medium prior to the analysis. Each strain contained an expression system with an indicated AD; the sTF expression cassette integrated in the genome in the ura3 locus (ura3 gene replaced by the sTF expression cassette), and the target gene cassette integrated in the aox2 locus (aox2 gene replaced by the target gene expression cassette). Equivalent of 10 μL of the culture supernatant from each culture was loaded on a gel (4-20% gradient) and the proteins were separated in an electric field (PowerPac HC; BioRad). The gel was stained with colloidal coomassie (PageBlue Protein Staining Solution; THERMO FISHER SCIENTIFIC®), and the visualization was performed on the ODYSSEY® CLx Imaging System instrument (LI-COR® Biosciences). The phytase (AppA) is indicated by an arrow. Three strains were selected for bioreactor cultivations; the strain with expression systems containing So-NAC102M (SEQ ID NO: 10) and Bn-TAF1M (SEQ ID NO: 11) activation domains, and the control strain with the VP16 AD (SEQ ID NO: 1) (FIG. 9).

Figure 9:
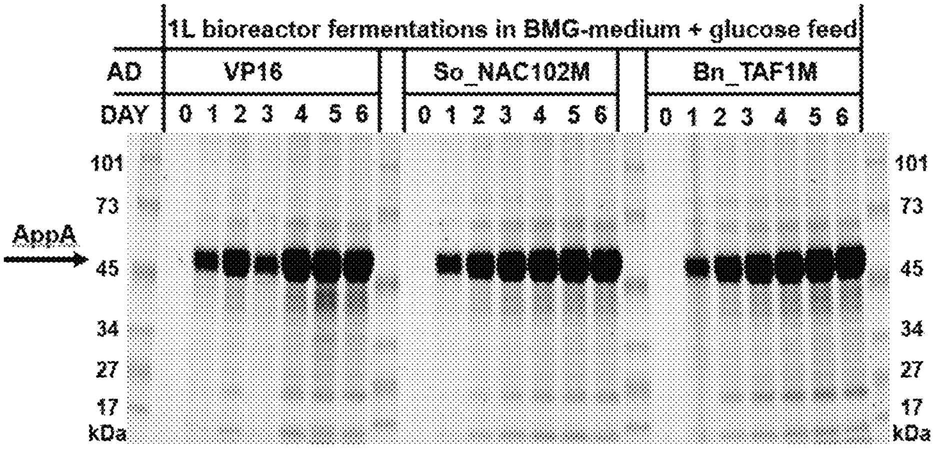

FIG. 9 depicts SDS-PAGE analysis (Coomassie stain gel) of phytase protein (AppA) produced by *Pichia pastoris* strains in 1 L bioreactors (see Example 4). A set of three *P. pastoris* strains were cultivated for 6 days in the BMG-medium with continuous glucose feeding. Equivalent of 2 μL of different time-points culture supernatants from each culture and was loaded on a gel (4-20% gradient) and the proteins were separated in an electric field (PowerPac HC; BioRad). The gel was stained with colloidal coomassie (PageBlue Protein Staining Solution; THERMO FISHER SCIENTIFIC®), and the visualization was performed on the ODYSSEY® CLx Imaging System instrument (LI-COR® Biosciences). The phytase protein (AppA) is indicated by an arrow.

Figure 10:
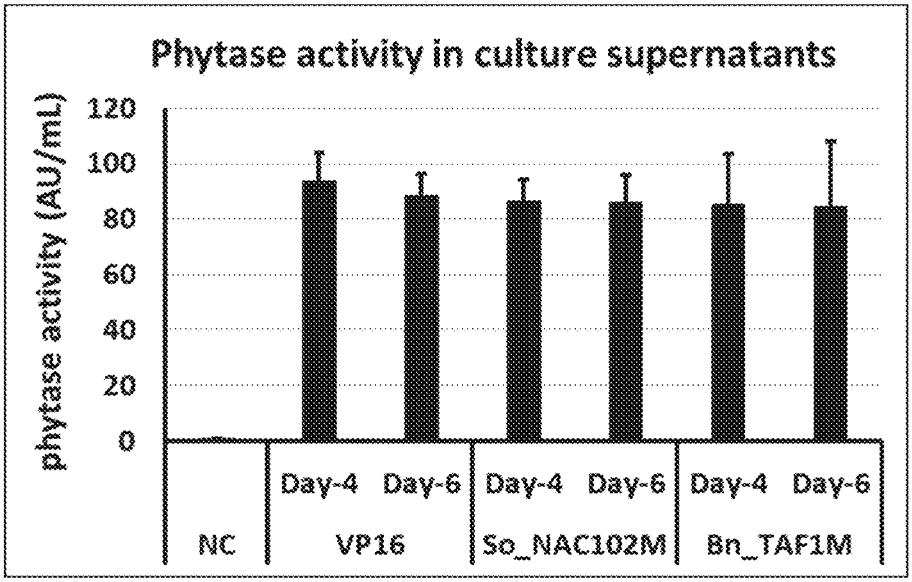

FIG. 10 depicts the phytase (AppA) activity analysis in culture supernatants of *Pichia pastoris* strains cultivated in 1 L bioreactors (see Example 4). One mL samples of the culture supernatants from day 4 and day 6 were diluted in 100 mM Na-acetate solution (pH 4.7) and processed by a gravity gel filtration (PD-10 desalting columns; BioRad). The phytase activity was assayed by Phytase Assay Kit (MyBioSource). The activity is expressed in arbitrary units per mL of the culture supernatant (AU/mL). The negative control (NC) represents a culture supernatant of 1 L bioreactor cultivation of *Pichia pastoris* strain not producing the phytase. The columns represent average values and the error bars standard deviations from three technical replicates.

Figure 11:
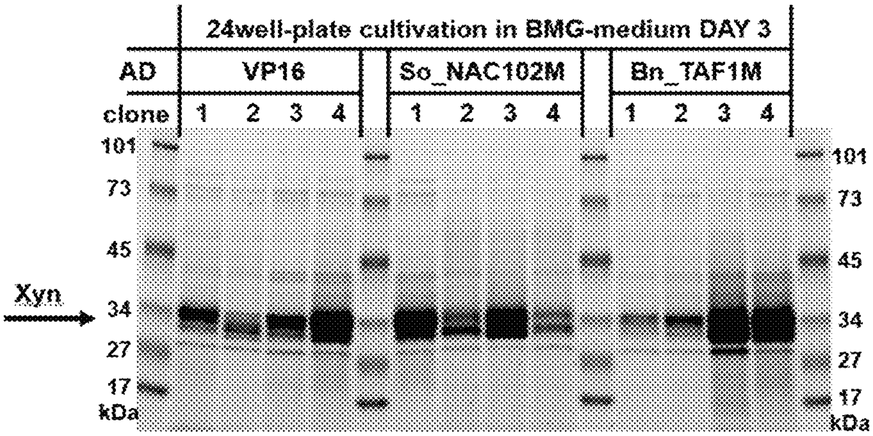

FIG. 11 depicts SDS-PAGE analysis (Coomassie stain gel) of xylanase protein (Xyn) produced by *Myceliophthora thermophila* strains with use of the expression systems containing three selected transcription activation domains (24 well plate, FIG. 1, Example 5). A set of four *M. thermophila* clones from each transformation was analyzed. Each clone was containing an expression system with an indicated AD, integrated in the genome in a random manner (1 or more integration events in unknown genomic loci). The strains were cultivated for 3 days in 4 mL of the BMG-medium prior to the analysis. Equivalent of 10 μL of the culture supernatant from each culture was loaded on a gel (4-20% gradient). The gel was stained with colloidal coomassie (PageBlue Protein Staining Solution; THERMO FISHER SCIENTIFIC®), and the visualization was performed on the ODYSSEY® CLx Imaging System instrument (LI-COR® Biosciences). The xylanase protein (Xyn) is indicated by an arrow. All cultures were analyzed for specific xylanase activity (FIG. 12).

Figure 12:
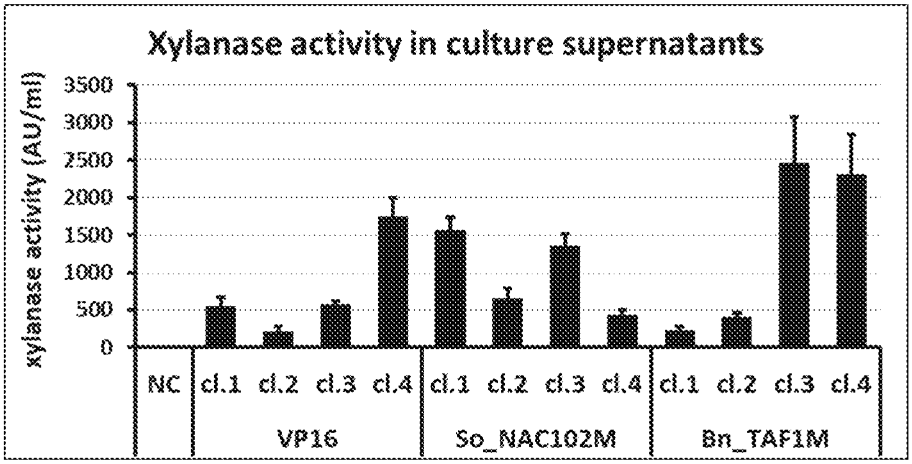

FIG. 12 depicts the xylanase activity analysis in culture supernatants of *Myceliophthora thermophila* strains cultivated in 4 mL of the BMG-medium for 3 days (24 well plate, FIG. 11, Example 5). The culture supernatants were diluted in 50 mM Tris·HCl (pH 8.0) and assayed for the xylanase activity by EnzCheck® Ultra Xylanase Assay Kit (INVITROGEN®). The activity is expressed in arbitrary units per mL of the culture supernatant (AU/mL). The negative control (NC) represents a culture supernatant from the parental *Myceliophthora thermophila* strain cultivated in BMG-medium. The columns represent average values and the error bars standard deviations from at least three technical replicates.

Figure 13:
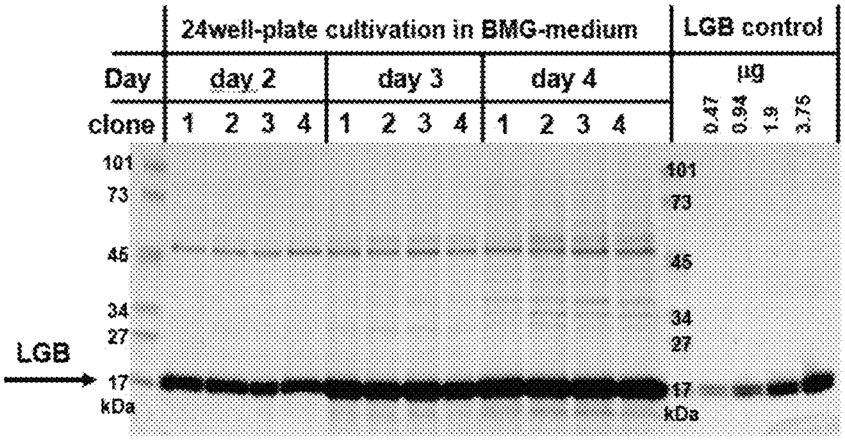

FIG. 13 depicts SDS-PAGE analysis (Coomassie stain gel) of a bovine 3-lactoglobulin B protein (LGB) produced by *Aspergillus oryzae* strains with use of the expression system containing Bn-TAF1M (SEQ ID NO: 11) transcription activation domain (24 well plate cultivation, the expression system scheme shown in FIG. 1; details described in Example 7). A set of four *A. oryzae* clones was analyzed. The clones were containing an expression system integrated in the genome in two selected loci (see Example 7). The strains were cultivated for up to 4 days in 4 mL of the BMG-medium prior to the analysis. Equivalent of 10 μL of the culture supernatant from each culture was loaded on a gel (4-20% gradient); a commercially available pure bovine β-lactoglobulin B protein was loaded as a positive control. The gel was stained with colloidal coomassie (PageBlue Protein Staining Solution; THERMO FISHER SCIENTIFIC®), and the visualization was performed on the ODYSSEY® CLx Imaging System instrument (LI-COR® Biosciences). The β-lactoglobulin B protein (LGB) is indicated by an arrow.

Figure 14:
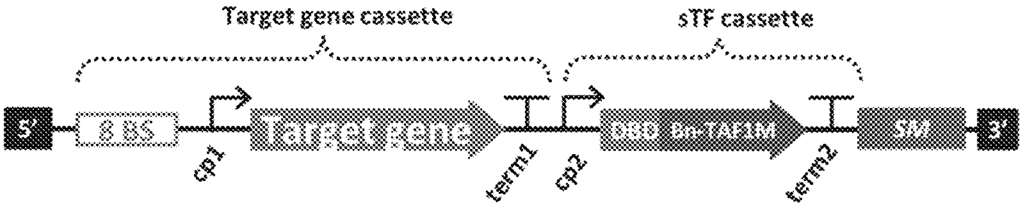

FIG. 14 illustrates an example of a scheme of an expression system comprising a transcription activation domain of the present invention. Indeed, FIG. 14 illustrates an example of a scheme of an expression system for testing transcription activation domain, and production of protein product of interest, in a eukaryotic organism or microorganism, exemplified on the assessment of regulated production of e.g. red fluorescent protein, mCherry, e.g. in *Pichia pastoris* or *Yarrowia lipolytica* (Example 8), or exemplified on the assessment of constitutive production of e.g. red fluorescent protein, mCherry, e.g. in *Yarrowia lipolytica* or *Cutaneotrichosporon oleaginosus* (Example 9). The expression system is constructed as a single DNA molecule, and it comprises or is composed of a target gene expression cassette, a sTF expression cassette, selection marker (SM) expression cassette, and genome integration DNA regions (flanks), here exemplified by genomic DNA sequences from *P. pastoris* located upstream of the ADE1 gene (5') and downstream of the ADE1 gene (3') or sequences from *Y. lipolytica* located upstream of the ANT1 gene (5') and downstream of the ANT1 gene (3'). In one embodiment FIG. 14 shows a synthetic expression system used for yeast species—e.g. *P. pastoris, Y. lipolytica*, and/or *C. oleaginosus.*

The target gene expression cassette can comprise or comprises multiple sTF-specific binding sites, here exemplified by eight sTF-specific binding sites (8 BS) positioned upstream of a core promoter (cp1), exemplified in Example 8 by An_201cp (SEQ ID NO: 23) of *Aspergillus niger* origin or exemplified by YI_565cp (SEQ ID NO: 32) of *Yarrowia lipolytica* origin, or exemplified in Example 9 by other core promoters. The eight sTF-binding sites and the core promoter form a synthetic promoter, which strongly activates the transcription of a target gene, in presence of synthetic transcription factor (sTF). The target gene could be any DNA sequence encoding a protein product of interest, here exemplified by mCherry-encoding DNA sequence (see Example 8 and Example 9). The transcription of the target gene can be terminated on the terminator sequence, here exemplified by the *Saccharomyces cerevisiae* ADH1 terminator (term1).

The synthetic transcription factor (sTF) expression cassette contains a core promoter (cp2), exemplified in Example 8 by An_008cp (SEQ ID NO: 22) or YI_242cp (SEQ ID NO: 33) or exemplified in Example 9 by other core promoters; the expression cassette further contains a sTF coding sequence, and a terminator. The core promoter provides constitutive low expression of the sTF. The sTF comprises or is composed of a DNA-binding-domain (BDB), which consists of bacterial DNA binding protein, such as Bm3R1 or TetR, and nuclear localization signal, such as the SV40 NLS, and the transcription activation domain, here exemplified by Bn_TAF1M (SEQ ID NO: 11). The sTF binds to the sTF-dependent synthetic promoter in the target gene expression cassette facilitating its transcription. In Example 8, where the TetR was used as the DBD of the sTF, the binding occurs in the absence of doxycycline, and the presence of increasing amounts of doxycycline leads to inhibition of the binding. The transcription of the sTF gene can be terminated on the terminator sequence, here exemplified by the *Trichoderma reesei* tef1 terminator (term2).

The selection marker (SM) expression cassette is any expression cassette allowing production of a specific protein in a host organism, which provides to the host organism means to grown under selection conditions, such as in presence of an antibiotic compound or an absence of essential metabolite. The SM cassette is exemplified here by the expression cassette allowing expression of the kanR gene (encoding aminoglycoside phosphotransferase enzyme) in *Pichia pastoris* strain (Example 8), or the expression cassette allowing expression of the NAT gene (encoding nourseothricin N-acetyl transferase) in *Yarrowia lipolytica* (Example 8 and Example 9) or *Cutaneotrichosporon oleaginosus* (Example 9).

Figure 15:
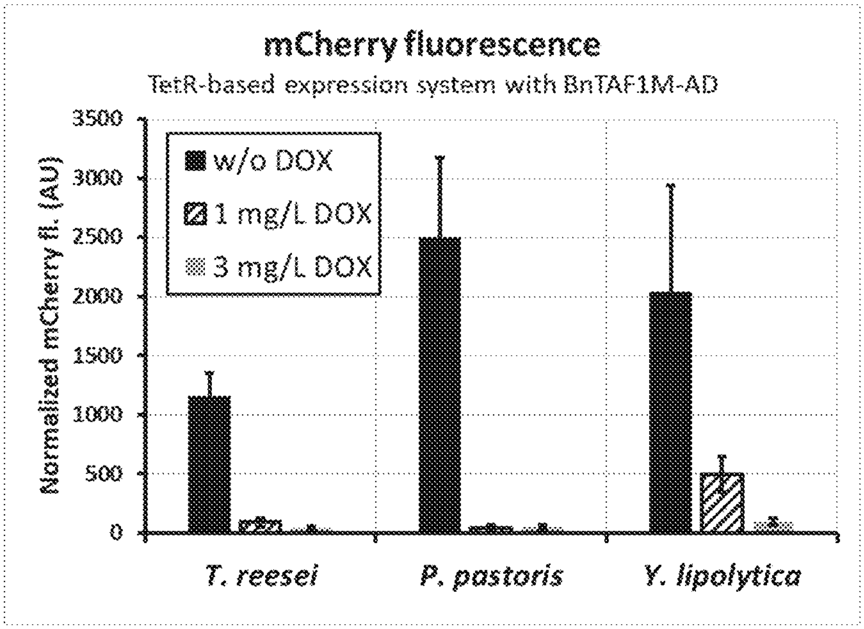

FIG. 15 depicts an example of the analysis of red fluorescent protein, mCherry, expressed in *Trichoderma reesei* strain transformed with the expression systems shown in FIG. 1 (the version with TetR-based sTF); and in *Pichia pastoris* and *Yarrowia lipolytica* strains transformed with the expression systems shown in FIG. 14. The aim of the experiment was to demonstrate possibility to use the plant-based transcription activation domain (here exemplified by Bn_TAF1M) in a doxycycline-regulated Tet-OFF-like expression system (Example 8). A set of strains, each containing an expression system integrated in the genome, were cultivated for 24 hours in BMG-medium prior to the analysis. The BMG-media without doxycycline (w/o DOX), and with 1 mg/L or 3 mg/L doxycycline (DOX) were used to assess the doxycycline dependent inhibition of the reporter gene expression. Quantitative analysis was performed by fluorometry measurement of mycelia or cell suspensions using the VARIOSKAN® instrument (Thermo Electron Corporation). The graphs show fluorescence intensity (mCherry) normalized by the optical density of the mycelium/cells suspensions used for the fluorometric analysis. The columns represent average values and the error bars standard deviations from three experimental replicates (three individual clones tested for each species).

Figure 16:
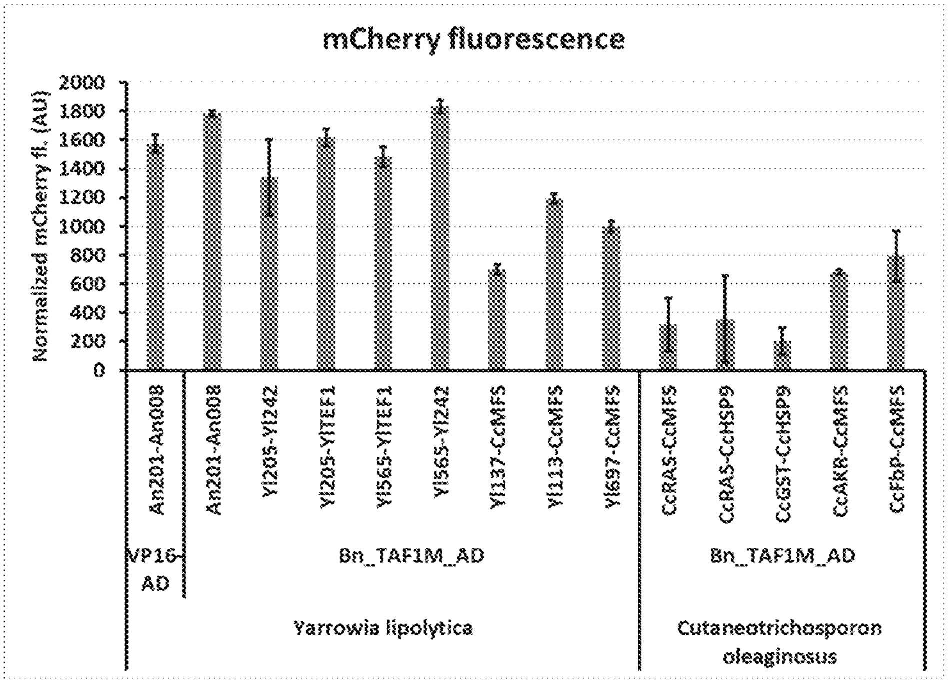

FIG. 16 depicts an example of the analysis of red fluorescent protein, mCherry, expressed in *Yarrowia lipolytica* and *Cutaneotrichosporon oleaginosus* strains transformed with the expression systems shown in FIG. 14. The aim of the experiment was to demonstrate the use of the plant-based transcription activation domain (here exemplified by Bn_TAF1M) in industrially relevant yeast production hosts (Example 9). A set of strains, each containing an expression system integrated in the genome, were cultivated for 24 hours in YPD medium prior to the analysis. Quantitative analysis was performed by fluorometry measurement of cell suspensions using the VARIOSKAN® instrument (Thermo Electron Corporation). The graphs show fluorescence intensity (mCherry) normalized by the optical density of the cells suspensions used for the fluorometric analysis. The columns represent average values and the error bars standard deviations from three experimental replicates.

SEQUENCE LISTING

| | |
|---|---|
| SEQ ID NO: 1 | VP16 |
| SEQ ID NO: 2 | At_NAC102 |
| SEQ ID NO: 3 | So_NAC102 |
| SEQ ID NO: 4 | At_TAF1 |
| SEQ ID NO: 5 | So_NAC72 |
| SEQ ID NO: 6 | Bn_TAF1 |
| SEQ ID NO: 7 | At_JUB1 |
| SEQ ID NO: 8 | So_JUB1 |
| SEQ ID NO: 9 | Bn_JUB1 |
| SEQ ID NO: 10 | So_NAC102M |
| SEQ ID NO: 11 | Bn_TAF1M |
| SEQ ID NO: 12 | At_NAC102 (comprises a nuclear localization signal) |
| SEQ ID NO: 13 | So_NAC102 (comprises a nuclear localization signal) |
| SEQ ID NO: 14 | At_TAF1 (comprises a nuclear localization signal) |
| SEQ ID NO: 15 | So_NAC72 (comprises a nuclear localization signal) |
| SEQ ID NO: 16 | Bn_TAF1 (comprises a nuclear localization signal) |
| SEQ ID NO: 17 | At_JUB1 (comprises a nuclear localization signal) |
| SEQ ID NO: 18 | So_JUB1 (comprises a nuclear localization signal) |
| SEQ ID NO: 19 | Bn_JUB1 (comprises a nuclear localization signal) |
| SEQ ID NO: 20 | So_NAC102M (comprises a nuclear localization signal) |
| SEQ ID NO: 21 | Bn_TAF1 M (comprises a nuclear localization signal) |
| SEQ ID NO: 22 | An_008cp |
| SEQ ID NO: 23 | An_201cp |
| SEQ ID NO: 24 | a phytase enzyme, thermo-stable mutated version Ap-pA_K24E |
| SEQ ID NO: 25 | Tr_hfb2cp |
| SEQ ID NO: 26 | Mm_Atp5Bcp |
| SEQ ID NO: 27 | Mm_Eef2cp |
| SEQ ID NO: 28 | Mm_Rpl4cp |
| SEQ ID NO: 29 | a bovine β-Lactoglobulin B protein |
| SEQ ID NO: 30 | VP64 |
| SEQ ID NO: 31 | an alkaline xylanase, thermo-stable mutated version xynHB_N188A |
| SEQ ID NO: 32 | Yl_565cp |
| SEQ ID NO: 33 | Yl_242cp |
| SEQ ID NO: 34 | Yl_205cp |
| SEQ ID NO: 35 | Yl_TEF1cp |
| SEQ ID NO: 36 | Yl_137cp |
| SEQ ID NO: 37 | Yl_113cp |
| SEQ ID NO: 38 | Yl_697cp |
| SEQ ID NO: 39 | Cc_RAScp |
| SEQ ID NO: 40 | Cc_MFScp |
| SEQ ID NO: 41 | Cc_HSP9cp |
| SEQ ID NO: 42 | Cc_GSTcp |
| SEQ ID NO: 43 | Cc_AKRcp |
| SEQ ID NO: 44 | Cc_FbPcp |

DETAILED DESCRIPTION OF THE INVENTION

The transcription factors studied by Naseri G et al. (2017, ACS Synthetic Biology, 6, 1742-1756) were from the NAC family of the *Arabidopsis thaliana* transcription factors, and some of the tested transcription factors, namely JUB1 and ATAF1, were shown to activate the transcription in *Saccharomyces cerevisiae* also without a fusion with other activation domains.

The NAC (i.e. NAM, ATAF, and CUC) family of the transcription factors is a large protein family containing functionally and structurally dissimilar proteins (Olsen, Ernst et al. 2015, Trends Plant Sci 10(2): 79-87). The NAC transcription factors share high degree of homology in the DNA-binding domains (the NAC domain), but often very low homology in the transcription activation domains.

The inventors of the present disclosure have now been able to identify the transcription activation domains of (e.g. NAC-family) transcription factors from e.g. *Arabidopsis thaliana, Brassica napus*, and *Spinacia oleracea*, the latter two species being common edible plant species, oilseed rape and spinach, respectively. While the high degree of sequence identity was present within the NAC domain, a large variation of sequence homology was found between the corresponding activation domains. For instance, the amino-acid sequence identity between TAF1-activation domain from *Arabidopsis thaliana* and *Brassica napus* was approximately 77%, while, the amino-acid sequence identity between JUB1-activation domain from *Arabidopsis thaliana* and *Spinacia oleracea* was only approximately 23%.

Also, the level of the activation domains functionality in the expression systems implemented in diverse fungal hosts was highly variable. For instance, the TAF1 activation domain of *Arabidopsis thaliana* origin was highly active in *Trichoderma reesei*, but almost inactive in *Pichia pastoris* (FIG. 4 and FIG. 8).

In addition, the EDLL motif previously successfully used by Naseri G et al. in *S. cerevisiae*, or by Tiwari, Belachew et al. (2012, The Plant Journal 70(5): 855-865) in *Arabidopsis thaliana*, proved to be completely inactive when tested in *Trichoderma reesei* (data not shown). Therefore, observations of the present disclosure indicate unpredictable function of (some) plant activation domains in diverse host organisms.

The inventors noticed that some of the tested plant-derived activation domains, in particular the TAF1 activation domain of *Brassica napus* (Bn-TAF1—SEQ ID NO: 6) and the NAC102 activation domain of *Spinacia oleracea* (So-NAC102—SEQ ID NO: 3); comprise an amino-acid composition resembling the typical acidic activation domains, enriched with acidic amino acids (such as glutamate and/or aspartate) and hydrophobic amino acids (such as leucine, isoleucine, and/or phenylalanine). The native versions of these activation domains, however, also contained some basic amino acids (e.g. especially lysine), which was hypothesized to limit the activity of the activation domains. The inventors modified the sequences of the two mentioned activation domains by replacing the unfavorable amino acids (e.g. lysines) in their structures for the amino acids more fitting the typical acidic activation domains sequence (e.g. leucines and/or glutamates). Surprising results were found with the modified domains.

Indeed, the inventors of the present disclosure were able to create modified effective transcription activation domains from native plant transcription activation domains. Very strong domains were obtained, which can be successfully used e.g. for replacing the current viral or other domains in artificial expression systems.

Indeed, the present invention concerns a modified non-viral transcription activation domain i.e. a variant of a non-viral transcription activation domain. As used herein "a modified domain" or "a modified transcription activation domain" refers to any non-native domain or transcription activation domain, respectively, that contains different material (e.g. a different amino acid or modified amino acid) compared to a corresponding unmodified (i.e. native or wild type) domain. As an example, a modified domain may comprise a deletion, substitution, disruption or insertion of one or more amino acids or parts of a domain, or insertion of one or more modified amino acids, compared to the corresponding (native or wild type) domain without said modification.

A modification of a domain may have been obtained e.g. by modifying the polynucleotide encoding said domain by any genetic method. Methods for making genetic modifications are generally well known and are described in various practical manuals describing laboratory molecular techniques. Some examples of the general procedure and specific embodiments are described in the Examples chapter. In one specific embodiment of the invention a modified non-viral transcription activation domain has been obtained by rational mutagenesis or random mutagenesis of the polynucleotide encoding said transcription activation domain.

In one embodiment of the invention the transcription activation domain comprises one or several modifications and/or mutations compared to the corresponding wild type transcription activation domain (amino acid) sequence. In a specific embodiment said transcription activation domain comprises one or several amino acid modifications or amino acid mutations compared to the corresponding wild type (i.e. native) transcription activation domain sequence.

In one embodiment the modified transcription activation domain is a transcription activation domain variant comprising increased acidic and/or hydrophobic amino acid content compared to a native (i.e. unmodified) transcription activation domain. The acidic amino acids include aspartate and glutamate. The hydrophobic amino acids include alanine, valine, leucine, isoleucine, proline, phenylalanine, cysteine and methionine. In a specific embodiment the modified transcription activation domain or the transcription activation domain variant comprises more aspartate, glutamate, leucine, isoleucine, and/or phenylalanine amino acids compared to the native (i.e. unmodified) transcription activation domain.

In one embodiment the transcription activation domain is a recombinant, synthetic or artificial transcription activation domain. As used herein "a recombinant activation domain" refers to an activation domain that has been obtained by genetically modifying genetic material, i.e. said domain may have been produced by a recombinant DNA technology. In one embodiment a polynucleotide encoding "a recombinant activation domain" comprises mutations compared to the corresponding wild type polynucleotide (e.g. comprise a deletion, substitution, disruption or insertion of one or more nucleic acids including an entire gene(s) or parts thereof compared to the domain before modification). In one embodiment "a recombinant activation domain" comprises or is a polypeptide encoded by a polynucleotide that has been cloned in a system that supports expression of said polynucleotide and furthermore translation of said polypeptide. Indeed, a (genetically) modified polynucleotide can encode a mutant polypeptide. As used herein "a synthetic domain" refers to a domain that has been produced by linking multiple amino acids via amide bonds. Synthesis of polypeptides can be carried out by methods including but not limited to classical solution-phase techniques and solid-phase methods. Also, in some embodiments "synthetic" can be seen as a synonym for "recombinant" as defined above. "An artificial domain" refers to a domain, which is non-native i.e. has not been made by nature or does not occur in nature, or e.g. a wild type domain when used in a non-native context.

A transcription activation domain (e.g. a modified transcription activation domain) of the present invention originates from a plant or plant transcription factor (e.g. an edible plant). As used herein "originates from a plant or plant transcription factor" i.e. "is of plant or plant transcription factor origin" or "is derived from a plant or plant transcription factor" refers to a situation, wherein said transcription activation domain is a protein or polypeptide, typically transcription factor, which exists in plants. Indeed, in one embodiment of the invention the amino acid sequence of a plant activation domain or a nucleotide sequence encoding said plant activation domain has been modified. In one specific embodiment the transcription activation domain originates from an edible plant or plant species, or from a food grade plant or plant species. As used herein "a food grade plant" refers to a non-toxic plant, which is safe for consumption, and is e.g. of sufficient quality to be used for food production, food storage, or food preparation purposes.

In one embodiment, the transcription activation domain originates from *Spinacia, Brassica, Ocimum* or *Arabidopsis*, or from *Spinacia oleracea, Brassica napus, Ocimum basilicum* or *Arabidopsis thaliana*. The transcription activation domain is any transcription activation domain of plant origin, here exemplified by ten examples based on or originating from transcription factors found in *Arabidopsis thaliana, Brassica napus*, and *Spinacia oleracea*.

Many see the use of viral activation domains or viral transcription factors as a problem in synthetic expression systems. Thus, there is a strong need for highly functional activation domains, which originate from acceptable sources (e.g. as judged by public or industry). The present invention provides a non-viral transcription activation domain originating from a plant, i.e. a transcription activation domain free from any viral components. Said non-viral transcription activation domains can offer the same or improved efficiency as the current virus-based transcription activation domains.

In one embodiment the transcription activation domain is selected from the group consisting of a transcription activation domain from the plant NAC-family transcription factors (e.g. a TAF (e.g. TAF1) transcription activation domain, a JUB (e.g. JUB1) transcription activation domain), or any fragment thereof. JUB transcription activation domains refer to transcription activation domains of JUNGBRUNNEN factors. E.g. among other effects JUB1 acts as a negative regulator of senescence and a positive regulator of the tolerance to heat and salinity stress in plants.

The new activation domains can be incorporated into existing synthetic expression systems, in particular in the structure of the synthetic transcription factors of the expression systems, where they can replace the current activation domains without compromising the function of the systems. In one embodiment the transcription activation domain of the present invention is used in a structure of an artificial transcription factor or said transcription activation domain is for a synthetic expression system.

In one embodiment of the invention the transcription activation domain is functional across diverse species. In cases where the transcription activation domain is for a synthetic expression system, the synthetic expression system is functional across diverse species.

The activation domain of the present invention can be of any length, preferably less than 500 amino acids. In one embodiment the transcription activation domain has a length of 20-300 amino acids, specifically 30-250 amino acids, or more specifically 40-200 amino acids, e.g. 20-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-210, 211-220, 221-230, 231-240, 241-250, 251-260, 261-270, 271-280, 281-290, 291-300 amino acids.

In a specific embodiment the transcription activation domain comprises or consists of an amino acid sequence having 70-100%, 75-100%, 80-100, 85-100%, 90-100%, or 95-100% sequence identity, e.g. at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity, to the amino acid sequence of SEQ ID NO: 2, 3, 4, 5, 6, 7, 8, 9, 10 or 11 (no nuclear localization signals comprised within said sequences), e.g. SEQ ID NO: 3, 5, 6, 8, 9, 10 or 11.

In one embodiment the transcription activation domain comprises or consists of an amino acid sequence having 60-100%, 65-100%, 70-100%, 75-100%, 80-100, 85-100%, 90-100%, or 95-100% sequence identity, e.g. at least 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity, to the amino acid sequence of SEQ ID NO: 12, 13, 14, 15, 16, 17, 18, 19, 20 or 21 (nuclear localization signals comprised in the sequences), e.g. SEQ ID NO: 13, 15, 16, 18, 19, 20 or 21.

In a very specific embodiment the transcription activation domain belongs to a group of i) acidic domains (called also "acid blobs" or "negative noodles", rich in D and E amino acids), ii) glutamine-rich domains (comprises multiple repetitions, e.g. "QQQXXXQQQ"-type repetitions), iii) proline-rich domains (comprises repetitions like "PPPXXXPPP") or iv) isoleucine-rich domains (comprises repetitions e.g. "IIXXII").

The present invention also concerns a polypeptide comprising the modified non-viral plant based transcription activation domain of the present invention, and a nuclear localization signal.

In one embodiment the modified activation domain of the present invention is for an artificial transcription factor. The present invention also concerns an artificial transcription factor. Generally, a transcription factors refers to a protein that binds to specific DNA sequences present in the upstream activation sequence (UAS), thereby controlling the rate of transcription, which is performed by RNA II polymerase. Transcription factors perform this function alone or with other proteins in a complex, by promoting (as an activator), or blocking (as a repressor) the recruitment of RNA polymerase to core promoters of genes. Artificial or synthetic transcription factor (sTF) refers to a protein which functions as a transcription factor but is not a native protein of a host organism. The artificial transcription factor of the present invention comprises the transcription activation domain of the present invention, a DNA-binding domain and a nuclear localization signal. In one embodiment, the DNA-binding protein of the artificial transcription factor is of prokaryotic origin. In one embodiment, the artificial transcription factor comprises a transcription activation domain of the present invention, a DNA-binding protein derived from prokaryotic, typically bacterial origin, and a nuclear localization signal, such as the SV40 NLS.

In the polypeptides or artificial transcription factors of the present invention the nuclear localization signal can be any suitable localization signal known to a person skilled in the art e.g. a SV40 nuclear localization signal or the nuclear localization signal can have an amino acid sequence comprising or consisting of PKKKRKV.

DNA-binding domain refers to the region of a protein, typically specific protein domain, which is responsible for interaction (binding) of the protein with a specific DNA sequence, such as a promoter of a target gene.

The modified transcription activation domain, polypeptide or artificial transcription factor of the present invention can be obtained from a polynucleotide encoding said modified transcription activation domain, polypeptide or artificial transcription factor, or from a polynucleotide modified to encode said modified transcription activation domain, polypeptide or artificial transcription factor.

The present invention also concerns a polynucleotide encoding the transcription activation domain, polypeptide or artificial transcription factor of the present invention.

The polynucleotide encoding the transcription activation domain, polypeptide or artificial transcription factor of the present invention may be operatively linked to any suitable promoter or controlling sequence including, but not limited to core promoter sequences, e.g. anyone presented in e.g. SEQ ID NO:s 22, 23, 25, 26, 27, 28, or any of SEQ ID NO:s 32-44, or any combination thereof.

As used herein "polynucleotide" refers to any polynucleotide, such as single or double-stranded DNA (synthetic DNA, genomic DNA, or cDNA) or RNA, comprising a nucleic acid sequence encoding a polymer of amino acids or a polypeptide in question.

Codon is a tri-nucleotide unit which is coding for a single amino acid in the genes that code for proteins. The codons encoding one amino acid may differ in any of their three nucleotides. Different organisms have different frequency of the codons in their genomes, which has implications for the efficiency of the mRNA translation and protein production.

Coding sequence refers to a DNA sequence that encodes a specific RNA or polypeptide (i.e. a specific amino acid sequence). The coding sequence could, in some instances, contain introns (i.e. additional sequences interrupting the reading frame, which are removed during RNA molecule maturation in a process called RNA splicing). If the coding sequence encodes a polypeptide, this sequence contains a reading frame.

Reading frame is defined by a start codon (AUG in RNA; corresponding to ATG in the DNA sequence), and it is a sequence of consecutive codons encoding a polypeptide (protein). The reading frame is ending by a stop codon (one of the three: UAG, UGA, and UAA in RNA; corresponding to TAG, TGA, and TAA in the DNA sequence). A person skilled in the art can predict the location of open reading frames by using generally available computer programs and databases.

Herein, the terms "polypeptide" and "protein" are used interchangeably to refer to polymers of amino acids of any length.

Variations or modifications of any one of the sequences or subsequences set forth in the description and claims are still within the scope of the invention provided that they can be used in the present invention or as activation domains for engineering of gene expressions or polynucleotides encoding said activation domains.

Identity of any sequence or fragments thereof compared to the sequence of this disclosure refers to the identity of any sequence compared to the entire sequence of the present invention. As used herein, the % identity between the two sequences is a function of the number of identical positions shared by the sequences (e.g. % identity=# of identical positions/total # of positions×100), taking into account the number of gaps, and the length of each gap, which need to be introduced for optimal alignment of the two sequences. The comparison of sequences and determination of identity percentage between two sequences can be accomplished using mathematical algorithms available in the art. This applies to both amino acid and nucleic acid sequences. As an example, sequence identity may be determined by using BLAST (Basic Local Alignment Search Tools) or FASTA (FAST-All). In the searches, setting parameters "gap penalties" and "matrix" are typically selected as default.

An expression cassette or expression system of the present invention comprises the polynucleotide encoding the transcription activation domain, polypeptide or artificial transcription factor of the present invention. In one embodiment the expression cassette further comprises a polynucleotide sequence encoding a desired product.

In one embodiment the polynucleotide encoding the modified activation domain of the present invention is for an expression cassette or expression system or the modified activation domain of the present invention is for an expression cassette or expression system.

In one embodiment the expression system comprises one or more expression cassettes, and optionally at least one expression cassette further comprises a polynucleotide sequence encoding a desired product.

An expression system of the present invention can be an orthogonal expression system, i.e. a system comprising or consisting of heterologous (non-native) core promoters, transcription factor(s), and transcription-factor-specific binding sites. Typically, the orthogonal expression system is functional (transferable) in diverse eukaryotic organisms such as eukaryotic microorganisms.

In one embodiment an expression system comprises a target gene expression cassette and/or an artificial transcription factor expression cassette comprising the activation domain of the present invention. Furthermore, the expression system can comprise e.g. one or more selection marker (SM) expression cassettes and optionally genome integration DNA regions (flanks). In one embodiment the expression system is constructed as a single DNA molecule or as two separate DNA molecules.

FIGS. 1, 2 3 and 14 show examples of schemes of an expression system or expression cassette comprising the activation domain of the present invention e.g. for heterologous protein production.

In one embodiment a target gene expression cassette refers to a cassette, which comprises a target gene coding sequence and the sequences controlling the expression (see FIGS. 1-3, 14). In one embodiment the expression cassette comprises a promoter sequence and/or a 3' untranslated region, which optionally comprises a polyadenylation site. Sequences controlling the expression of the target genes can include but are not limited to a promoter (e.g. a core promoter, e.g. as exemplified in FIG. 1 or 2 by An_201cp of *Aspergillus niger* origin or in FIG. 3 or 14 by CP1 (e.g. Mm_Atp5Bcp, or Mm_Eef2cp, or Mm_Rpl4cp of *Mus musculus* origin, or An_201cp of *Aspergillus niger* origin, or Yl_565cp of *Yarrowia lipolytica* origin)) and one or more sTF-specific binding sites (e.g. in FIG. 1, 2, 3 or 14 exemplified by sTF-specific binding sites (BS)), which can be positioned e.g. upstream of a core promoter).

In one embodiment a target gene expression cassette comprises a synthetic promoter, which comprises a variable number of sTF-binding sites, usually 1 to 10, typically 1, 2, 4 or 8, separated by 0-20, typically 5-15, random nucleotides, and a core promoter (CP); a target gene; and a terminator.

A target gene can be any DNA sequence (e.g. native or heterologous) encoding a polypeptide or a protein product of interest (see e.g. Examples 1, 4, 6, 8 and 9, FIGS. 1-3 and 14). In one embodiment the transcription of the target gene is terminated on the terminator sequence (e.g. in FIG. 1 exemplified by the *Trichoderma reesei* pdc1 terminator (Tr_PDC1t), in FIG. 2 by the *Saccharomyces cerevisiae* ADH1 terminator (Sc_ADH1t), in FIG. 3 by any of SV40 terminator of simian virus 40 origin, or FTH1 terminator of *Mus musculus* origin, in FIG. 14 by ADH1 terminator of *Saccharomyces cerevisiae*).

In one embodiment the artificial transcription factor (sTF) expression cassette comprises a core promoter (e.g. exemplified as Tr_hfb2cp in FIG. 1, or An_008cp in FIG. 2, or CP2 (Mm_Atp5Bcp, or Mm_Eef2cp, or Mm_Rpl4cp of *Mus musculus* origin) in FIG. 3, or CP2 (e.g. An_008cp or Yl_242cp) in FIG. 14), a sTF coding sequence, and a terminator (see FIGS. 1-3 and 14). The core promoter provides constitutive low expression of the sTF. The sTF binds to the sTF-dependent synthetic promoter in the target gene expression cassette facilitating its transcription. The sTF comprises or is composed of a DNA-binding-domain (BDB), which optionally comprises or consists of a bacterial DNA binding protein (e.g. Bm3R1 transcriptional regulator from *Bacillus megaterium* in Example 1; PhlF transcriptional regulator from *Pseudomonas protegens* in Example 6; McbR transcriptional regulator from *Corynebacterium* sp. in Example 6; or TetR transcriptional regulator from *Escherichia coli* in example 8) and/or a nuclear localization signal, such as the SV40 NLS, and a transcription activation domain (AD). The transcription of the sTF gene can be terminated on the terminator sequence, (e.g. as exemplified by the *Trichoderma reesei* tef1 terminator (Tr_TEF1 t) in FIG. 1 or 2, or by any of SV40 terminator of simian virus 40 origin, or FTH1 terminator of *Mus musculus* origin in FIG. 3, or *Trichoderma reesei* tef1 terminator in FIG. 14).

In a specific embodiment the expression system comprises at least two individual expression cassettes e.g. formed as one or more DNA molecules (e.g. two or more):

(a) a target gene expression cassette, which comprises a synthetic promoter, which comprises a variable number of sTF-binding sites, usually 1 to 10, typically 1, 2, 4 or 8, separated by 0-20, typically 5-15, random nucleotides, and a CP; a target gene; and a terminator, and (b) an artificial transcription factor cassette, which comprises a CP controlling expression of a gene encoding a fusion protein (artificial transcription factor, sTF), the artificial transcription factor itself (sTF), and a terminator.

A selection marker (SM) expression cassette is any expression cassette allowing production of a specific protein in a host organism, which provides to the host organism means to grown under selection conditions, such as in presence of an antibiotic compound or an absence of essential metabolite. In one embodiment of the invention the SM cassette can be an expression cassette allowing expression of the pyr4 gene (encoding orotidine 5'-phosphate decarboxylase enzyme) e.g. in *Trichoderma reesei* strain (see e.g. Examples 1 and 3), the pyrG gene (encoding orotidine 5'-phosphate decarboxylase enzyme) e.g. in *Aspergillus oryzae* strain (see e.g. Example 7), the hygR gene (encoding Hygromycin-B 4-O-kinase) e.g. in *Myceliophthora thermophila* strain (see e.g. Example 5), the URA3 gene (encoding orotidine 5'-phosphate decarboxylase enzyme) e.g. in *Pichia pastoris* strain (see e.g. Example 4), A (encoding aminoglycoside phosphotransferase enzyme) e.g. in *Pichia pastoris* strain (see e.g. Example 4), the pac gene (encoding puromycin N-acetyltransferase enzyme) e.g. in CHO cells (see e.g. Example 6), kanR gene (encoding aminoglycoside phosphotransferase enzyme) e.g. in *Pichia pastoris* strain (see e.g. Example 8), and/or NAT gene (encoding nourseothricin N-acetyl transferase) e.g. in *Yarrowia lipolytica* or *Cutaneotrichosporon oleaginosus* strain (see e.g. Examples 8 and 9).

When an expression system is constructed as two separate DNA molecules, the first DNA can comprise or can be composed of an artificial transcription factor expression cassette comprising the activation domain of the present invention, and optionally a selection marker (SM) expression cassette and/or genome integration DNA regions (flanks); and the second DNA can comprise or be composed of a target gene expression cassette, and optionally a selection marker (SM) expression cassette and/or genome integration DNA regions (flanks). Each cassette can be integrated into separate locus of the host genome, together forming a functional gene expression system.

The genome integration DNA regions (flanks) used in the present invention can be selected from any genomic loci present in the productions hosts, e.g. the genomic DNA sequences from *Trichoderma reesei* located upstream of the egl1 gene (EGL1-5') and downstream of the egl1 gene (EGL1-3') (see e.g. Example 5), e.g. the genomic DNA sequences from *Pichia pastoris* located upstream of the URA3 gene (URA3-5') and downstream of the URA3 gene (URA3-3') (see e.g. Example 4) and genomic DNA sequences from *Pichia pastoris* located upstream of the AOX2 gene (AOX2-5') and downstream of the AOX2 gene (AOX2-3') (see e.g. Example 4), or e.g. the genomic DNA sequences from *Aspergillus oryzae* located upstream of the gaaC gene (gaaC-5') and downstream of the gaaC gene (gaaC-3') (see e.g. Example 7) and genomic DNA sequences from *Aspergillus oryzae* located upstream of the gluC gene (gluC-5') and downstream of the gluC gene (gluC-3') (see e.g. Example 7), or e.g. the genomic DNA sequences for targeting the ADE1 gene of *Pichia pastoris* or the anti gene of *Y. lipolytica* (examples 8 and 9).

In one specific embodiment of the present invention the expression system e.g. for a eukaryotic or microorganism host, which comprises: (a) an expression cassette comprising a core promoter, said core promoter being the only "promoter" controlling the expression of a DNA sequence encoding the activation domain or artificial transcription factor (sTF) of the present invention, and (b) one or more expression cassettes each comprising a target gene sequence encoding a desired protein product operably linked to a synthetic promoter, said synthetic promoter comprising a core promoter identical to (a) or another core promoter, and activation domain or sTF-specific binding sites upstream of the core promoter.

Eukaryotic promoter is a region of DNA necessary for initiation of transcription of a gene. It is upstream of a DNA sequence encoding a specific RNA or polypeptide (coding sequence). It contains an upstream activation sequence (UAS) and a core promoter. A person skilled in the art can predict the location of a promoter by using generally available computer programs and databases.

Core promoter (CP) is a part of a (eukaryotic) promoter and it is a region of DNA immediately upstream (5'-upstream region) of a coding sequence which encodes a polypeptide, as defined by the start codon. The core promoter comprises all the general transcription regulatory motifs necessary for initiation of transcription, such as a TATA-box, but does not comprise any specific regulatory motifs, such as UAS sequences (binding sites for native activators and repressors).

The selection of the CPs can be based on the level of expression of the genes in the selected organisms, containing the candidate CP in their promoters. Another selection criterion can be the presence of a TATA-box in the candidate CP. In one embodiment the screen for functional CPs to be used in the present invention is advantageously performed by in vivo assembling the candidate CP with the sTF-dependent reporter cassette expressed in an organism, e.g. in *S. cerevisiae* strain, constitutively expressing the sTF. The resulting strains are tested for a level of a reporter, preferably fluorescence, and these levels are compared to a control strain.

The core promoter (CP) typically comprises a DNA sequence containing the 5'-upstream region of a eukaryotic gene, starting 10-50 bp upstream of a TATA-box and ending 9 bp upstream of the ATG start codon. In one embodiment the distance between the TATA-box and the start codon is no greater than 180 bp and no smaller than 80 bp. The core promoter typically comprises also a DNA sequence comprising random 1-20 bp at its 3'-end. In one embodiment the core promoter comprises a DNA sequence having at least 90% sequence identity to said 5'-upstream region of a eukaryotic gene, and a DNA sequence comprising random 1-20 bp at its 3'-end.

In one embodiment the core promoter is a DNA sequence containing: 1) a 5'-upstream region of a highly expressed gene starting 10-50 bp upstream of the TATA box and ending 9 bp upstream of the start codon, where the distance between the TATA box and the start codon is no greater than 180 bp and no smaller than 80 bp, 2) random 1-20 bp, typically 5 to 15 or 6 to 10, which are located in place of the 9 bp of the DNA region (1) immediately upstream of the start codon; or a DNA sequence containing: 1) a DNA sequence having at least 90%, 91%, 92%, 93%, 94%, 95%, 96%, 97%, 98% or 99% sequence identity to said 5'-upstream region and 2) random 1-20 bp, typically 5 to 15 or 6 to 10, which are located in place of the 9 bp of the DNA region (1) immediately upstream of the start codon.

As used in the above chapter "highly expressed gene" in an organism is a gene which has been shown in that organism to be expressed among the top 3% or 5% of all genes in any studied condition as determined by transcriptomics analysis, or a gene, in an organism where the transcriptomics analysis has not been performed, which is the closest sequence homologue to the highly expressed gene.

TATA-box refers to a DNA sequence (TATA) upstream of the start codon, where the distance of the TATA sequence and the start codon is no greater than 180 bp and no smaller than 80 bp. In case of multiple sequences fulfilling the description, the TATA-box is defined as the TATA sequence with smallest distance from the start codon.

The core promoters (CPs) used in the expression system or one or several expression cassettes of the present invention can be different or identical with each other, e.g. the first one, CP1, can be identical to the second one CP2, (or the third one CP3, or the fourth one CP4—in the expression systems composed of multiple expression cassettes), or the first one, CP1, can be different from the second one, CP2.

In one embodiment one or more CPs are universal core promoters functional in diverse eukaryotic organisms. In one embodiment of the present invention, e.g. Tr_hfb2cp (SEQ ID NO: 25), An_008cp (SEQ ID NO: 22), or Yl_242cp (SEQ ID NO: 33) can be used for controlling the expression of the sTF in several organisms, e.g. *Trichoderma reesei* (see e.g. Examples 1 and 3 and 8), *Aspergillus* oryzae (see e.g. Example 7), *Myceliophthora thermophila* strain (see e.g. Example 5), *Pichia pastoris* (see e.g. Example 8) or *Yarrowia lipolytica* (see e.g. Example 8). In another embodiment of the present invention, e.g. An_201cp (SEQ ID NO: 23) can be used for controlling the expression of the target gene in conjunction with upstream located sTF-binding sites in several organisms, e.g. *Pichia pastoris* (see e.g. Example 4 and 8), *Trichoderma reesei* (see e.g. Examples 1 and 3 and 8), *Aspergillus oryzae* (see e.g. Example 7), *Myceliophthora thermophila* strain (see e.g. Example 5) or *Yarrowia lipolytica* (example 8). Also, other CPs suitable for the present invention include but are not limited to An_008cp (SEQ ID NO: 22) (e.g. in *Pichia pastoris*, see example 4), Mm_Atp5Bcp (SEQ ID NO: 26) (e.g. in *Trichoderma reesei* or CHO cells, see examples 1 and 6), Mm_Eef2cp (SEQ ID NO: 27) (e.g. in *Trichoderma reesei* or CHO cells, see examples 1 and 6), Mm_Rpl4cp (SEQ ID NO: 28), any CP of SEQ ID NO:s 32-44, or any combination thereof.

The sTF-binding sites and a core promoter (e.g. eight Bm3R1-specific binding sites and An_201cp; FIGS. 1 and 2) can form a synthetic promoter, which strongly activates the transcription of a target gene, in the presence of an artificial transcription factor. In specific applications, where the target gene is a native (homologous) gene of a host organism, the synthetic promoter can be inserted immediately upstream of the target gene coding region in the genome of the host organism, possibly replacing the original (native) promoter of the target gene.

A synthetic promoter refers to a region of DNA which functions as a eukaryotic promoter, but it is not a naturally occurring promoter of a host organism. It contains an upstream activation sequence (UAS) and a core promoter, wherein the UAS, or the core promoter, or both elements, are not native to the host organism. In one embodiment of the invention, the synthetic promoter comprises (usually 1-10, typically 1, 2, 4 or 8) sTF-specific binding sites (synthetic UAS—sUAS) linked to a core promoter. In one embodiment of the invention sTF-binding sites and the core promoter form a synthetic promoter, which strongly activates the transcription of a target gene, in the presence of an artificial transcription factor capable of binding sTF binding sites. It is also possible to construct multiple synthetic promoters with different numbers of binding sites (usually 1-10, typically 1, 2, 4 or 8, separated by 0-20, typically 5-15 random nucleotides) controlling different target genes simultaneously by one sTF. This would for instance result in a set of differently expressed genes forming a metabolic pathway.

Two or more expression cassettes can be introduced to a eukaryotic host (typically integrated into a genome) as two or more individual DNA molecules, or as one DNA molecule in which the two or more expression cassettes are connected (fused) to form a single DNA.

In one embodiment, the present invention provides tools for expression systems not dependent on the intrinsic transcriptional regulation of the expression host.

The tuning of the expression system for different expression levels of at least target genes and/or transcription factors can be carried out in a host organism where a multitude of options, including choices of CPs, sTFs, different numbers of BSs, and target genes, can be tested.

The present invention concerns a non-viral transcription activation domain, which can be used in a eukaryotic host. In one embodiment the polypeptide, artificial transcription factor, polynucleotide, expression cassette or expression system of the present invention is for a eukaryotic host. A eukaryotic host of the present invention comprises the transcription activation domain, polypeptide, artificial transcription factor, polynucleotide, expression cassette or expression system of the present invention.

A eukaryotic (production) host suitable for the present invention can be selected from the group consisting of:

1) Fungal kingdom, including yeast, such as classes Saccharomycetales, including but not limited to species *Saccharomyces cerevisiae, Kluyveromyces lactis, Candida krusei* (*Pichia kudriavzevii*), *Pichia pastoris* (*Komagataella pastoris*), *Pichia kudriavzevii, Eremothecium gossypii, Kazachstania exigua, Yarrowia lipolytica, Zygosaccharomyces lentus*, and others; or Schizosaccharomycetes, such as *Schizosaccharomyces pombe*; filamentous fungi, such as classes Eurotiomycetes, including but not limited to species *Aspergillus niger, Aspergillus nidulans, Aspergillus oryzae, Penicillium chrysogenum*, and others; Sordariomycetes, including but not limited to species *Trichoderma reesei, Myceliophthora thermophila*, and others; or Mucorales, such as *Mucor indicus* and others;
2) Animal kingdom, including but not limited to mammals (Mammalia) and cells thereof, including but not limited to species *Mus musculus* (mouse), *Cricetulus griseus* (hamster), *Homo sapiens* (human), and others; insects, including but not limited to species *Mamestra brassicae, Spodoptera frugiperda, Trichoplusia ni, Drosophila melanogaster*, and others.

In one embodiment the eukaryotic host is selected from the group consisting of a cell of fungal species including yeast and filamentous fungi, and a cell of animal species including mammals (e.g. non-human mammals); or from the group consisting of a cell of *Trichoderma, Trichoderma reesei, Pichia, Pichia pastoris, Pichia kudriavzevii, Aspergillus, Aspergillus oryzae, Aspergillus niger, Myceliophthora, Myceliophthora thermophila, Saccharomyces, Saccharomyces cerevisiae, Yarrowia, Yarrowia lipolytica, Cutaneotrichosporon, Cutaneotrichosporon oleaginosus* (*Trichosporon oleaginosus, Cryptococcus curvatus*), *Zygosaccharomyces*, Chinese hamster ovary (CHO) cells, and *Cricetulus griseus*.

A method for producing a desired protein product in a eukaryotic host comprises cultivating the host under suitable cultivation conditions. By "suitable cultivation conditions" are meant any conditions allowing survival or growth of the host organism, and/or production of the desired product in the host organism. A desired product can be a product of the target polynucleotide (i.e. a polypeptide or protein), or a compound produced by a polypeptide or protein or by a metabolic pathway. In the present context the desired product is typically a protein product.

The present invention also concerns use of the transcription activation domain, polypeptide, artificial transcription factor, polynucleotide, expression cassette, expression system or eukaryotic host for metabolic engineering and/or production of a desired protein product. As used herein "metabolic engineering" refers to controlling or optimizing genetic or regulatory processes within a cell. Metabolic engineering allows e.g. modified production of a desired protein product in a cell.

The tools of the present invention speed up the process of industrial host development and enable the use of novel hosts which have high potential for specific purposes, but very limited spectrum of tools for genetic engineering.

The present invention also relates to a method of preparing a non-viral transcription activation domain of the present invention or a polynucleotide encoding said non-viral transcription activation domain, wherein said method comprises obtaining a transcription activation domain polypeptide originating from a plant transcription factor or obtaining a polynucleotide encoding said transcription activation domain polypeptide originating from a plant transcription factor, and modifying the obtained transcription activation domain polypeptide or polynucleotide. Methods of modifying polypeptides are well known to a person skilled in the art and include but are not limited to e.g. methods causing a deletion, substitution, disruption or insertion of one or more amino acids or parts of a polypeptide, or insertion of one or more modified amino acids. Methods of modifying polynucleotides are also well known to a person skilled in the art and include but are not limited to e.g. methods causing a deletion, substitution, disruption or insertion of one or more nucleic acids or parts of a polynucleotide, or insertion of one or more modified nucleic acids. A modification of a polypeptide can be obtained e.g. by modifying the polynucleotide encoding the polypeptide by any genetic method. Methods for making genetic modifications are generally well known and are described in various practical manuals describing laboratory molecular techniques. Some examples of the general procedure and specific embodiments are described in the Examples chapter. In one specific embodiment of the invention a modified non-viral transcription activation domain has been obtained by rational mutagenesis or random mutagenesis of the polynucleotide encoding said transcription activation domain.

It will be obvious to a person skilled in the art that, as the technology advances, the inventive concept can be implemented in various ways. The invention and its embodiments are not limited to the examples described below but may vary within the scope of the claims.

EXAMPLES

Example 1

Testing of Transcription Activation Domains from Plant Transcription Factors for Heterologous Gene Expression in *Trichoderma reesei* (FIG. 1, FIG. 4)

The reporter expression systems for testing different transcription activation domains were constructed as single DNA molecules (plasmids) (FIG. 1). All the plasmids contained *Trichoderma reesei* genome-integration flanks to allow integration of the construct into the egl1 locus of *T. reesei* (JGI122081; ge nome.jgi.doe.gov/Trire2/Trire2.home.html). The egl1-integration flanks contained DNA sequences corresponding to outside DNA regions of the egl1 coding region: EGL1-5' was a sequence 811 to 1811 bp upstream of the start codon; EGL1-3' was a sequence 2 to 1001 bp downstream of the stop codon. In addition, the plasmids contained a pyr4 selection marker (SM) gene with a suitable promoter and terminator. In addition, the plasmids contained regions needed for propagation of the plasmids in *E. coli* (not shown in FIG. 1). Also, the plasmids contained target gene cassette, which consisted of eight Bm3R1-biding sites (BS; sequences shown in Table 1A and 1B); An_201 core promoter (An_201cp; sequence shown in Table 1A and 1B); mCherry encoding DNA (target gene; sequence shown in Table 1A and 11B); and *Trichoderma reesei* pdc1 terminator (Tr_PDC1t). The plasmids further contained synthetic transcription factor (sTF) expression cassette, which consisted of *Trichoderma reesei* hfb2 core promoter (Tr_hfb2cp; sequence shown in Table 1A and 1B); the sTF coding region; and *Trichoderma reesei* tef1 terminator (Tr_TEF1t).

The sTF coding regions of all the plasmids contained the same DNA-binding-domain (DBD; Bm3R1 transcriptional regulator from *Bacillus megaterium*; NCBI Reference Sequence: WP_013083972.1; encoding DNA codon optimized for *Aspergillus niger*; sequence shown in Table 1A and 1B), and SV40 NLS. The transcription activation domains (AD) were selected from plant transcription factors available in public databases and the corresponding protein encoding DNA were codon optimized for *T. reesei*. Following protein sequences were selected and used:

- At_NAC102-AD (SEQ ID NO: 2)=Region of amino-acid sequence 126-215 from the AT5G63790 protein of *Arabidopsis thaliana* (GenBank: BAH57132.1)
- So_NAC102-AD (SEQ ID NO: 3)=Region of amino-acid sequence 173-303 from the NAC domain-containing protein 2 of *Spinacia oleracea* (NCBI Reference Sequence: XP_021863783.1)
- At_TAF1-AD (SEQ ID NO: 4)=Region of amino-acid sequence 129-229 from the ATAF1 protein of *Arabidopsis thaliana* (GenBank: CAA52771.1)
- So_NAC72-AD (SEQ ID NO: 5)=Region of amino-acid sequence 185-369 from the NAC domain-containing protein 72 of *Spinacia oleracea* (NCBI Reference Sequence: XP_021840466.1)
- Bn_TAF1-AD (SEQ ID NO: 6)=Region of amino-acid sequence 186-286 from the NAC domain-containing protein 2 of *Brassica napus* (NCBI Reference Sequence: NP_001302866.1)
- At_JUB1-AD (SEQ ID NO: 7)=Region of amino-acid sequence 106-197 from the NAC domain containing protein 42 of *Arabidopsis thaliana* (NCBI Reference Sequence: NP_001324496.1)
- So_JUB1-AD (SEQ ID NO: 8)=Region of amino-acid sequence 227-357 from the JUNGBRUNNEN 1-like protein of *Spinacia oleracea* (NCBI Reference Sequence: XP_021854333.1)
- Bn_JUB1-AD (SEQ ID NO: 9)=Region of amino-acid sequence 189-279 from the JUNGBRUNNEN 1 protein of *Brassica napus* (NCBI Reference Sequence: XP_013670411.1)
- VP16-AD (SEQ ID NO: 1) was used as the transcription activation domain in a control construct.

*Trichoderma reesei* strain M1909 (VTT culture collection) was used as the parental strain. This strain is a mutagenized version of the QM9414 strain and it contains additional deletions including deletion of the pyr4 gene—rendering the uracil auxotrophy of the strain. The reporter expression systems (FIG. 1) were integrated into egl1 locus (replacing the native coding region) using the corresponding flanking regions for homologous recombination. The transformations were done by using the CRISPR-Cas9-protein transformation protocol: Isolated *T. reesei* protoplasts were suspended into 1500 μL of STC solution (1.33 M sorbitol, 10 mM Tris-HCl, 50 mM $CaCl_2$), pH 8.0). For each transformation, one hundred μL of protoplast suspension was mixed with 2 μg of donor DNA (linear fragment corresponding to the construct shown in FIG. 1) and 50 μL of EGL1-targeting RNP-solution (1 μM Cas9 protein (IDT), 1 μM synthetic crRNA (IDT), and 1 μM tracrRNA (IDT)) and 100 μL of the transformation solution (25% PEG 6000, 50 mM $CaCl_2$), 10 mM Tris-HCl, pH 7.5). The mixture was incubated on ice for 20 min. Two mL of transformation solution was added and the mixture was incubated 5 min at room temperature. Four mL of STC was added followed by addition of 7 mL of the molten (50° C.) top agar (200 g/L D-sorbitol, 6.7 g/L of yeast nitrogen base (YNB, Becton, Dickinson and Company), synthetic complete amino acid without uracil, 20 g/L D-glucose, and 20 g/L agar). The mixture was poured onto a selection plate (200 g/L D-sorbitol, 6.7 g/L of yeast nitrogen base (YNB, Becton, Dickinson and Company), synthetic complete amino acid without uracil, 20 g/L D-glucose, 20 g/L agar). Cultivation was done at 28° C. for five or seven days, colonies were picked and re-cultivated on the SCD-URA plates (6.7 g/L of yeast nitrogen base (YNB, Becton, Dickinson and Company), synthetic complete amino acid without uracil, 20 g/L D-glucose, and 20 g/L agar).

The correct strains were selected by qPCR of the genomic DNA of each transformed strain. The qPCR signal of the mCherry gene was compared to a qPCR signal of a unique native sequence in each host. In addition the correct deletion of the egl1 gene was confirmed by absent qPCR signal of the egl1 target. The selected strains were sporulated on PDA agar plates (39 g/L BD-Difco Potato dextrose agar). Spores (conidia) were collected from the PDA plates, and used as inoculum in liquid cultivations for the fluorescence analysis.

For the quantitative fluorometry analysis of the mCherry production in the mycelia of the tested strains (FIG. 4), pre-cultures (inoculated by conidia) of *Trichoderma reesei* strains were grown for 24 hours in YPG medium (20 g/L bacto peptone, 10 g/L yeast extract, and 30 g/L gelatin). Four mL of the YE-glc medium (20 g/L glucose, 10 g/L yeast extract, 15 g/L $KH_2PO_4$, 5 g/L $(NH_4)_2SO_4$, 1 mL/L trace elements (3.7 mg/L $COCl_2$, 5 mg/L $FeSO_4 \cdot 7H_2O$, 1.4 mg/L $ZnSO_4 \cdot 7H_2O$, 1.6 mg/L $MnSO_4 \cdot 7H_2O$), 2.4 mM $MgSO_4$, and 4.1 mM $CaCl_2$, pH adjusted to 4.8) in 24-well cultivation plates was inoculated to OD600=0.5 by the mycelia suspension. The cultures were grown for 24 hours at 800 rpm (Infors HT Microtron) and 28° C., centrifuged, pellets washed with water, and resuspended in 0.2 mL of sterile water. Two hundred μL of each mycelium suspension was analyzed in black 96-well plates (Black Cliniplate; THERMO SCIENTIFIC®) using the VARIOSKAN® (Thermo Electron Corporation) fluorometer. The settings for mCherry were 587 nm (excitation) and 610 nm (emission), respectively. For normalization of the fluorescence results, the analyzed mycelium-suspensions were diluted 100× and OD600 was measured in transparent 96-well microtiter plates (NUNC) using VARIOSKAN® (Thermo Electron Corporation). The results from the analysis are shown in FIG. 4.

TABLE 1

DNA sequences of example sTF-expression cassettes and reporter expression cassettes for testing the engineered plant-based transcription activation domains. The functional DNA parts are indicated: 8xsTF-specific binding site (black bolded text); core promoters (underlined text); mCherry coding region (black bolded underlined text); terminators (italics); and sTF (bolded italics) including the plant-based activation domain (bolded underlined italics).
Example DNA sequences of the tested expression systems with selected activation domains

| | |
|---|---|
| A 8BS(Bm3R 1)-An_201cp-mCherry-Tr_PDC1t + Tr_hfb2cp - BM3R1_So - NAC102M-Tr_TEF1t | TTTGCAGGCATTTGCTCGGCTAGT**CGGAATGAACATTCATTCCG**AGACCTAGGATGTGA**CGGAATGAAGGTT**<br>**CATTCCG**GACTCTAGATAAGCA**CGGAATGAACTTTCATTCCG**CTGAAGCTTGTCAAT**CGGAATGAAGGTTCAT**<br>TCCGGCTAGT**CGGAATGAACATTCATTCCG**AGACCTAGGATGTGA**CGGAATGAAGGTTCATTCCG**GACTCTA<br>GATAAGCA**CGGAATGAACTTTCATTCCG**CTGAAGCTTGTCAAT**CGGAATGAAGGTTCATTCCG**GCTAGTTCTC<br>CCCGGAAACTGTGGCCATATGTTCAAAGACTAGGATGGATAAATGGGGTATATAAAGCACCCTGACTCCCTTC<br>CTCCAAGTTCTATCTAACCAGCCATCCTACACTCTACATATCCACACCAATCTACTACAATTAATTAAA**ATGGTG**<br>**AGCAAGGGCGAGGAGGATAACATGGCCATCATCAAGGAGTTCATGCGCTTCAAGGTGCACATGGAGGGCT**<br>**CCGTGAACGGCCACGAGTTCGAGATCGAGGGCGAGGGCGAGGGCCGCCCCTACGAGGGCACCCAGACCG**<br>**CCAAGCTGAAGGTGACCAAGGGTGGCCCCCTGCCCTTCGCCTGGGACATCCTGTCCCCTCAGTTCATGTAC**<br>**GGCTCCAAGGCCTACGTGAAGCACCCCGCCGACATCCCCGACTACTTGAAGCTGTCCTTCCCCGAGGGCTT**<br>**CAAGTGGGAGCGCGTGATGAACTTCGAGGACGGCGGCGTGGTGACCGTGACCCAGGACTCCTCCCTGCAG**<br>**GACGGCGAGTTCATCTACAAGGTGAAGCTGCGCGGCACCAACTTCCCCTCCGACGGCCCCGTAATGCAGA**<br>**AGAAGACCATGGGCTGGGAGGCCTCCTCCGAGCGGATGTACCCCGAGGACGGCGCCCTGAAGGGCGAGA**<br>**TCAAGCAGAGGCTGAAGCTGAAGGACGGCGGCCACTACGACGCTGAGGTCAAGACCACCTACAAGGCCA**<br>**AGAAGCCCGTGCAGCTGCCCGGCGCCTACAACGTCAACATCAAGTTGGACATCACCTCCCACAACGAGGA**<br>**CTACACCATCGTGGAACAGTACGAACGCGCCGAGGGCCGCCACTCCACCGGCGGCATGGACGAGTTATAC**<br>**AAG**TAATGAGGATCT*CCCGGCATGAAGTCTGACCGGGTAGTATGAGGGTTCATCGTCACCTTGATAGAATAAT*<br>*AGACGATAAAGCAGGCCACGGGCAGGTACCGATTGTCAATCCGGCAGGTTAGGAGGCGTGTTGGAAATGAGT*<br>*TTATGGGTTATGGTCAAATCGGATAGTATGAGGTACATAGTTTGTAAATCTCAAGATTATTTTCTTCCTTAATCT*<br>*TGCACGTCGCATGAGAGGGACCGAGAAGAGAATTGATGAAGGGCTCTTGAAGATGAGATGAATCACGTGGTT*<br>*GCTGAAGCTTCAGTAGTCTCGGGTACCTGTTCTTTCCCACAAACAGTAGCCAGGCTAGAGGTACTGAGTACCC*<br>*GCTCACCGTATCTAATCATCCGACCTGAAATCTTCAAGCTGTTTTATTGACACTTCGAGTCCATCTTCATTCAC*<br>*GTAAGGAGAACTTCTAGGACATCACTTATCCCGCCATATTTAGCTGCAAGGAGTCAATTGCAATGTCAGATTCC*<br>*GCTCCTAAGAGGAAACAGGGCCCTGGCGGCTCAGATGGCTCGGCATTGAAGAAGAGAAAGGTATGATGACAA*<br>*GAATGCTTGCTACAAATTACCCAGTAGCCGGGCACTAACAGCTCCCTGGCCTAGGTAGACTACCTACCTCAAG*<br>*GTACGACACATGGCAGCACTGGAGGGGGAATAGGCAGACTGGACGACAGTGGACAAGATACGGTCGCACAA*<br>*CCTTTGTCGTGGCATCGCGAGAATAATCGTCACAAGCTTCACGTATGCAGACGGAGACAAGATGATTTGGTTG*<br>*TCGAAGTCATGAATTCACTTCTATCTAGTTTTTTTGTTCCCTTTTGTTTTGCATTCCCAGAGAAGTTCTGATGGA*<br>*ACCCTTATTCCCAGCCTCTCAATTAACGTGCCTCGATTCATAGTCGAGTGCTCATGCATAGCAACATTGATCGT*<br>*TTCGTCGTAGAAGTGAGCGCATGGTGGTGCCCACCTGGAGAAACCTCACGAGGGACCCCAGAACATCAGGT*<br>*GTTGATGATGGGTATCGC*GGCCGGCCTTA***GCGGAGGAGCATGAAGATGTCCTGGTAGTTGCCCATCTGGTC***<br>***GTTGTGGAACTGGCCGTGCTGGTGAAGGGGTCGTCCGGAAAGGGCTCCATGTAGTTGAAGCTGGGGAAG***<br>***TCGAGGTTGTCCTCAAGCTCGTTCCAGAGAGGGTCGCTCTGGACCTCGAGATCGCACATGAACTCGGGGCT***<br>***AGCCACGTGGTTGGAGCCGGAGGTGTCGGTGTGGAGGTCGGGGACGCTGTCGCTGGTGTCGAAGTGCATG***<br>***AGGTCGTTGAGAGGCTGAGGAATGGGCGACGTGGTGGTCATGTTGTAGCCCATGGGGCCCGTCTGGCCGA***<br>***GGGTGCTGATGACGGGGAGCTGATCCTCAAACTCGGGGTACTGCGTGATGCTGGTGGGCATGCTGCCGGA***<br>***GCCGACCTTGCGCTTCTTCTTAGGAGGGCTAGCCGATTGTCGGGAGAGAGCAGCCCAGAGCGATTCCTCTA***<br>***CCCCCGTAAGCAACTCATCCGTTAGAGAGAGATAATCGTTTTCGATCATCTCATAGACCTCCATAAACGATC***<br>***CGAATAGGATGGCGATCAGGGCATTCTCGGGCAAGTTTCGAATTACGCCCTGTTTCTGTCCCTCTCGAAAG***<br>***AAGGTGCAGACGAACTCAACAAGTTTTTGGTATGCAAGGCGTGACTCTTCGGTTAGGAATGTACCTTGGGA***<br>***ATGTGTCTTGATAAATCCCAAGGCGCGCGGATGGTTCTTTGTGAATGTGACCATTCCCTCGAAGATATGATG***<br>***GAACCCATCGCGATAACCGTCCCTTTCGTTCGCCAAGCCACTCTCGATACATTGCAAAAATTCATTAACGTG***<br>***CTGCTGGAACAGCTCGTTGACCAGACTCTCCTTATTCTTAAAGTATCGGTAAATCGTTCCTGCGCCGACCTT***<br>***AGCATTTTCAGCGATCATCGGCATCGTAGTGGCGTCAAACCCGCGTTCGGCGAACAGAAGGAGCGAGGCA***<br>***GAAAAAATAGCTTTTTGTTTCGTGGGTGTGGACTCCAT***TGTTATAAGTGGTGATGGTTGGTATTCAACAAAGA |

TABLE 1-continued

DNA sequences of example sTF-expression cassettes and reporter expression cassettes for testing the engineered plant-based transcription activation domains. The functional DNA parts are indicated: 8×sTF-specific binding site (black bolded text); core promoters (underlined text); mCherry coding region (black bolded underlined text); terminators (italics); and sTF (bolded italics) including the plant-based activation domain (bolded underlined italics).
Example DNA sequences of the tested expression systems with selected activation domains

| | |
|---|---|
| | ATGTTTGTGTTTGGAGAGTTGAGAAAGAGGAGTTGAGTGAATGTGGTGATGGTTGTAGATGAGTGTGCTGATG |
| | AGGATGGAAAAGATTGTTGGATGGCGGGAATCGAGGTCTTCTTTATACTTTTTTTCTGGCCCTCTTCATCTTC |
| | CAGCTCTCGCAGGCTGTTGCTAGAAATCTCGACGCGCAATTAACCCTCACGGGCGCGGCCGC |
| B | TTTGCAGGCATTTGCTCGGCTAGTCGGAATGAACATTCATTCCGAGACCTAGGATGTGACGGAATGAAGGTT |
| 8BS(Bm3R1)- | CATTCCGGACTCTAGATAAGCACGGAATGAACTTTCATTCCGCTGAAGCTTGTCAATCGGAATGAAGGTTCAT |
| An_201cp- | TCCGGCTAGTCGGAATGAACATTCATTCCGAGACCTAGGATGTGACGGAATGAAGGTTCATTCCGGACTCTA |
| mCherry- | GATAAGCACGGAATGAACTTTCATTCCGCTGAAGCTTGTCAATCGGAATGAAGGTTCATTCCGGCTAGTTCTC |
| Tr_PDC1t + | CCCGGAAACTGTGGCCATATGTTCAAAGACTAGGATGGATAAATGGGGTATATAAAGCACCCTGACTCCCTTC |
| Tr_hfb2cp- | CTCCAAGTTCTATCTAACCAGCCATCCTACACTCTACATATCCACACCAATCTACTACAATTAATTAAAATGGTG |
| BM3R1_Bn- | AGCAAGGGCGAGGAGGATAACATGGCCATCATCAAGGAGTTCATGCGCTTCAAGGTGCACATGGAGGGCT |
| TAF1M- | CCGTGAACGGCCACGAGTTCGAGATCGAGGGCGAGGGCGAGGGCCGCCCCTACGAGGGCACCCAGACCG |
| Tr_TEF1t | CCAAGCTGAAGGTGACCAAGGGTGGCCCCCTGCCCTTCGCCTGGGACATCCTGTCCCCTCAGTTCATGTAC |
| | GGCTCCAAGGCCTACGTGAAGCACCCCGCCGACATCCCCGACTACTTGAAGCTGTCCTTCCCCGAGGGCTT |
| | CAAGTGGGAGCGCGTGATGAACTTCGAGGACGGCGGCGTGGTGACCGTGACCCAGGACTCCTCCCTGCAG |
| | GACGGCGAGTTCATCTACAAGGTGAAGCTGCGCGGCACCAACTTCCCCTCCGACGGCCCCGTAATGCAGA |
| | AGAAGACCATGGGCTGGGAGGCCTCCTCCGAGCGGATGTACCCCGAGGACGGCGCCCTGAAGGGCGAGA |
| | TCAAGCAGAGGCTGAAGCTGAAGGACGGCGGCCACTACGACGCTGAGGTCAAGACCACCTACAAGGCCA |
| | AGAAGCCCGTGCAGCTGCCCGGCGCCTACAACGTCAACATCAAGTTGGACATCACCTCCCACAACGAGGA |
| | CTACACCATCGTGGAACAGTACGAACGCGCCGAGGGCCGCCACTCCACCGGCGGCATGGACGAGTTATAC |
| | AAGTAATGAGGATCTCCCGGCATGAAGTCTGACCGGGTAGTATGAGGGTTCATCGTCACCTTGATAGAATAAT |
| | AGACGATAAAGCAGGCCACGGGCAGGTACCGATTGTCAATCCGGCAGGTTAGGAGGCGTGTTGGAAATGAGT |
| | TTATGGGTTATGGTCAAATCGGATAGTATGAGGTACATAGTTTGTAAATCTCAAGATTATTTTCTTCCTTAATCT |
| | TGCACGTCGCATGAGAGGGACCGAGAAGAGAATTGATGAAGGGCTCTTGAAGATGAGATGAATCACGTGGTT |
| | GCTGAAGCTTCAGTAGTCTCGGGTACCTGTTCTTTCCCACAAACAGTAGCCAGGCTAGAGGTACTGAGTACCC |
| | GCTCACCGTATCTAATCATCCGACCTGAAATCTTCAAGCTGTTTTATTGACACTTCGAGTCCATCTTCATTCAC |
| | GTAAGGAGAACTTCTAGGACATCACTTATCCCGCCATATTTAGCTGCAAGGAGTCAATTGCAATGTCAGATTCC |
| | GCTCCTAAGAGGAAACAGGGCCCTGGCGGCTCAGATGGCTCGGCATTGAAGAAGAGAAAGGTATGATGACAA |
| | GAATGCTTGCTACAAATTACCCAGTAGCCGGGCACTAACAGCTCCCTGGCCTAGGTAGACTACCTACCTCAAG |
| | GTACGACACATGGCAGCACTGGAGGGGGAATAGGCAGACTGGACGACAGTGGACAAGATACGGTCGCACAA |
| | CCTTTGTCGTGGCATCGCGAGAATAATCGTCACAAGCTTCACGTATGCAGACGGAGACAAGATGATTTGGTTG |
| | TCGAAGTCATGAATTCACTTCTATCTAGTTTTTTTGTTCCCTTTTGTTTTGCATTCCCAGAGAAGTTCTGATGGA |
| | ACCCTTATTCCCAGCCTCTCAATTAACGTGCCTCGATTCATAGTCGAGTGCTCATGCATAGCAACATTGATCGT |
| | TTCGTCGTAGAAGTGAGCGCATGGTGGTGCCCACCTGGAGAAACCTCACGAGGGACCCCAGAACATCAGGT |
| | GTTGATGATGGGTATCGCGGCCGGCCCTAGTAAGGCTTGGGCATGTTGTACATGAACATGTCCTGCAGGGG |
| | AAACAGCTGGTTGCTGCCGCCGCCGCCAAAGGCGGTGGCGTCGATGTAGTTGAAGCCGAAGTCGAGGGAG |
| | TTGTCGTCGTTGGCAGCGCCGGACCAGTCGTCCCAGAGGGGCTCGCTCTGGACCTCGCTGGTGAACTCGG |
| | GGCTGACGACCTGCTCGCTGCAGCTGCTCTCGGTGGTGTGGAGGTCGGGGACGCTGTCGCTGGTGTCGAA |
| | GTAGACGAAGTCGTTGGGCATGACAGGCGGAGGAGGCATGCCCATCTCGCTGCCGGAGCCGACCTTGCGC |
| | TTCTTCTTAGGAGGGCTAGCCGATTGTCGGGAGAGAGCAGCCCAGAGCGATTCCTCTACCCCCGTAAGCAA |
| | CTCATCCGTTAGAGAGAGATAATCGTTTTCGATCATCTCATAGACCTCCATAAACGATCCGAATAGGATGGC |
| | GATCAGGGCATTCTCGGGCAAGTTTCGAATTACGCCCTGTTTCTGTCCCTCTCGAAAGAAGGTGCAGACGA |
| | ACTCAACAAGTTTTTGGTATGCAAGGCGTGACTCTTCGGTTAGGAATGTACCTTGGGAATGTGTCTTGATAA |
| | ATCCCAAGGCGCGCGGATGGTTCTTTGTGAATGTGACCATTCCCTCGAAGATATGATGGAACCCATCGCGA |
| | TAACCGTCCCTTTCGTTCGCCAAGCCACTCTCGATACATTGCAAAAATTCATTAACGTGCTGCTGGAACAGC |
| | TCGTTGACCAGACTCTCCTTATTCTTAAAGTATCGGTAAATCGTTCCTGCGCCGACCTTAGCATTTTCAGCGA |
| | TCATCGGCATCGTAGTGGCGTCAAACCCGCGTTCGGCGAACAGAAGGAGCGAGGCAGAAAAAATAGCTTT |
| | TTGTTTCGTGGGTGTGGACTCCATTGTTATAAGTGGTGATGGTTGGTATTCAACAAAGAATGTTTGTGTTTGGA |
| | GAGTTGAGAAAGAGGAGTTGAGTGAATGTGGTGATGGTTGTAGATGAGTGTGCTGATGAGGATGGAAAAGAT |
| | TGTTGGATGGCGGGAATCGAGGTCTTCTTTATACTTTTTTTCTGGCCCTCTTCATCTTCCAGCTCTCGCAGGC |
| | TGTTGCTAGAAATCTCGACGCGCAATTAACCCTCACGGGCGCGGCCGC |
| C | GGGTTAATTGCGCGTCGAGGCTAGCAACCCAAAGTAATAAGTCTGTAGTAATTGGTCTCGCCCTGAATTCCAA |
| An_008cp- | ACTATAAATCAACCACTTTCCCTCCTCCCCCCCGCCCCCACTTGGTCGATTCTTCGTTTTCTCTCTACCTTCTTT |
| BM3R1_Bn- | CTATTCGGTTTTCTTCTTCTTTTATTTTCCCTCTCCCATCAATCAAATTCATATTTGAAAAAAATTAACATTAATAA |
| TAF1M- | ATATCTACAATGGAATCTACTCCTACTAAGCAAAAAGCCATCTTCTCTGCCTCCTTGTTGTTGTTCGCTGAGA |
| Tr_TEF1t | GAGGTTTCGACGCTACCACTATGCCAATGATTGCCGAAAACGCTAAGGTTGGTGCTGGTACTATCTACAGAT |
| | ACTTCAAGAACAAAGAATCCTTAGTTAATGAGTTGTTTCAACAACACGTCAATGAATTTTTGCAATGTATCGA |
| | ATCTGGTTTGGCTAACGAAAGAGATGGTTACAGAGACGGTTTCCACCACATCTTCGAAGGTATGGTCACCTT |
| | CACCAAGAACCATCCTAGAGCCTTAGGTTTCATCAAGACCCACTCTCAAGGTACTTTTTTGACCGAAGAATC |
| | CAGATTGGCTTATCAAAAGTTGGTCGAATTTGTCTGTACTTTCTTCAGAGAAGGTCAAAAGCAAGGTGTCAT |
| | CAGAAATTTGCCAGAAAACGCTTTGATTGCTATCTTGTTCGGTTCTTTCATGGAAGTCTACGAAATGATTGAA |
| | AACGATTATTTGTCTTTGACTGATGAATTATTAACCGGTGTTGAGGAATCCTTGTGGGCTGCCTTGTCTCGTC |
| | AATCTGCTAGCCCACCTAAGAAGAAGCGTAAAGTGGGCAGTGGCTCTGAGATGGGTATGCCTCCTCCACCT |
| | GTTATGCCTAACGACTTCGTGTATTTTGATACGTCAGATTCTGTTCCCGACTTGCATACTACGGAATCCTCTT |
| | GTTCAGAGCAGGTTGTATCACCAGAATTTACATCTGAAGTCCAATCAGAACCACTGTGGGACGATTGGTCA |
| | GGTGCCGCAAACGATGACAATTCACTTGATTTTGGTTTTAATTACATCGATGCAACCGCATTTGGTGGCGGA |
| | GGCAGTAATCAGCTGTTTCCATTGCAGGATATGTTCATGTACAACATGCCTAAGCCTTATTGAGGCCGGCCG |
| | CGATACCCATCATCAACACCTGATGTTCTGGGGTCCCTCGTGAGGTTTCTCCAGGTGGGCACCACCATGCGC |
| | TCACTTCTACGACGAAACGATCAATGTTGCTATGCATGAGCACTCGACTATGAATCGAGGCACGTTAATTGAG |
| | AGGCTGGGAATAAGGGTTCCATCAGAACTTCTCTGGGAATGCAAAACAAAAGGGAACAAAAAAACTAGATAGA |

TABLE 1-continued

DNA sequences of example sTF-expression cassettes and reporter expression cassettes for testing the engineered plant-based transcription activation domains. The functional DNA parts are indicated: 8×sTF-specific binding site (black bolded text); core promoters (underlined text); mCherry coding region (black bolded underlined text); terminators (italics); and sTF (bolded italics) including the plant-based activation domain (bolded underlined italics).
Example DNA sequences of the tested expression systems with selected activation domains

| | |
|---|---|
| | AGTGAATTCATGACTTCGACAACCAAATCATCTTGTCTCCGTCTGCATACGTGAAGCTTGTGACGATTATTCTC |
| | GCGATGCCACGACAAAGGTTGTGCGACCGTATCTTGTCCACTGTCGTCCAGTCTGCCTATTCCCCCTCCAGTG |
| | CTGCCATGTGTCGTACCTTGAGGTAGGTAGTCTACCTAGGCCAGGGAGCTGTTAGTGCCCGGCTACTGGGTA |
| | ATTTGTAGCGCTGGAGCG |
| D | GGGTTAATTGCGCGTCGAGGCTAGCAACCCAAAGTAATAAGTCTGTAGTAATTGGTCTCGCCCTGAATTCCAA |
| An_008cp- | ACTATAAATCAACCACTTTCCCTCCTCCCCCCCGCCCCCACTTGGTCGATTCTTCGTTTTCTCTCTACCTTCTTT |
| BM3R1_So- | CTATTCGGTTTTCTTCTTCTTTTATTTTCCCTCTCCCATCAATCAAATTCATATTTGAAAAAAATTAACATTAATAA |
| NAC102M- | ATATCTACAATGGAATCTACTCCTACTAAGCAAAAAGCCATCTTCTCTGCCTCCTTGTTGTTGTTCGCTGAGA |
| Tr_TEF1t | GAGGTTTCGACGCTACCACTATGCCAATGATTGCCGAAAACGCTAAGGTTGGTGCTGGTACTATCTACAGAT |
| | ACTTCAAGAACAAAGAATCCTTAGTTAATGAGTTGTTTCAACAACACGTCAATGAATTTTTGCAATGTATCGA |
| | ATCTGGTTTGGCTAACGAAAGAGATGGTTACAGAGACGGTTTCCACCACATCTTCGAAGGTATGGTCACCTT |
| | CACCAAGAACCATCCTAGAGCCTTAGGTTTCATCAAGACCCACTCTCAAGGTACTTTTTTGACCGAAGAATC |
| | CAGATTGGCTTATCAAAAGTTGGTCGAATTTGTCTGTACTTTCTTCAGAGAAGGTCAAAAGCAAGGTGTCAT |
| | CAGAAATTTGCCAGAAAACGCTTTGATTGCTATCTTGTTCGGTTCTTTCATGGAAGTCTACGAAATGATTGAA |
| | AACGATTATTTGTCTTTGACTGATGAATTATTAACCGGTGTTGAGGAATCCTTGTGGGCTGCCTTGTCTCGTC |
| | AATCTGCTAGCCCACCTAAGAAGAAGCGTAAAGTGGGCTCAGGATCTATGCCAACCAGTATTACTCAATAT |
| | CCAGAGTTTGAGGATCAGTTACCAGTCATTTCAACCTTAGGACAGACAGGCCCAATGGGCTACAATATGAC |
| | AACCACGTCTCCCATCCCCCAGCCATTGAACGATCTGATGCATTTCGATACAAGTGACTCCGTTCCAGACTT |
| | GCATACGGATACGTCTGGCTCCAACCATGTGGCCTCCCCTGAATTTATGTGTGATTTAGAAGTTCAGTCTGA |
| | CCCTCTGTGGAACGAGTTAGAGGATAACTTGGACTTCCCCAGTTTTAACTATATGGAGCCCTTTCCAGACGA |
| | TCCTTTTACGAGTACAGCACAGTTCCACAACGACCAGATGGGTAATTATCAAGATATTTTTATGCTACTAAG |
| | GTGAGGCCGGCCGCGATACCCATCATCAACACCTGATGTTCTGGGGTCCCTCGTGAGGTTTCTCCAGGTGGG |
| | CACCACCATGCGCTCACTTCTACGACGAAACGATCAATGTTGCTATGCATGAGCACTCGACTATGAATCGAGG |
| | CACGTTAATTGAGAGGCTGGGAATAAGGGTTCCATCAGAACTTCTCTGGGAATGCAAAACAAAAGGGAACAAA |
| | AAAACTAGATAGAAGTGAATTCATGACTTCGACAACCAAATCATCTTGTCTCCGTCTGCATACGTGAAGCTTGT |
| | GACGATTATTCTCGCGATGCCACGACAAAGGTTGTGCGACCGTATCTTGTCCACTGTCGTCCAGTCTGCCTAT |
| | TCCCCCTCCAGTGCTGCCATGTGTCGTACCTTGAGGTAGGTAGTCTACCTAGGCCAGGGAGCTGTTAGTGCC |
| | CGGCTACTGGGTAATTTGTAGCGCTGGAGCG |
| E | ATTTAAATAGGGCCCGTTTAAACCCGCTGATCAGCCTCGACAGTTTCCGGGGAGAAGTAGTATGATACGAAA |
| 8BS(PhIF)- | CGTACCGTATCGTTAAGGTAGACCTAGGATGTGAATGATACGAAACGTACCGTATCGTTAAGGTGACTCTAG |
| Mm_Eef2c | ATAAGCCATGATACGAAACGTACCGTATCGTTAAGGTCTGAAGCTTGTCAATATGATACGAAACGTACCGTA |
| p-mCherry- | TCGTTAAGGTGCTAGTATGATACGAAACGTACCGTATCGTTAAGGTAGACCTAGGATGTGAATGATACGAAA |
| SV40t + | CGTACCGTATCGTTAAGGTGACTCTAGATAAGCCATGATACGAAACGTACCGTATCGTTAAGGTCTGAAGCT |
| Mm_Atp5b | TGTCAATATGATACGAAACGTACCGTATCGTTAAGGTGCTAGCCGAGCAAATGCCTGCCGGACGAGCACCC |
| cp-PhIF- | GGCGCCGTCACGTGACGCACCCAACCGGCGTTGACCTATAAAAGGCCGGGCGTTGACGTCAGCGGTCTCTT |
| So- | CCGCCGCAGCCGCCGCCATCGTCGGCGCGCTTCCCTGTTCACCTCTGACTCTGAGAATCCGTCGCCATCCG |
| NAC102M- | CCACCATGGTGAGCAAGGGCGAGGAGGATAACATGGCCATCATCAAGGAGTTCATGCGCTTCAAGGTGCA |
| Mn_FTH1t | CATGGAGGGCTCCGTGAACGGCCACGAGTTCGAGATCGAGGGCGAGGGCGAGGGCCGCCCCTACGAGGG |
| | CACCCAGACCGCCAAGCTGAAGGTGACCAAGGGTGGCCCCCTGCCCTTCGCCTGGGACATCCTGTCCCCT |
| | CAGTTCATGTACGGCTCCAAGGCCTACGTGAAGCACCCCGCCGACATCCCCGACTACTTGAAGCTGTCCTT |
| | CCCCGAGGGCTTCAAGTGGGAGCGCGTGATGAACTTCGAGGACGGCGGCGTGGTGACCGTGACCCAGGA |
| | CTCCTCCCTGCAGGACGGCGAGTTCATCTACAAGGTGAAGCTGCGCGGCACCAACTTCCCCTCCGACGGC |
| | CCCGTAATGCAGAAGAAGACCATGGGCTGGGAGGCCTCCTCCGAGCGGATGTACCCCGAGGACGGCGCC |
| | CTGAAGGGCGAGATCAAGCAGAGGCTGAAGCTGAAGGACGGCGGCCACTACGACGCTGAGGTCAAGACC |
| | ACCTACAAGGCCAAGAAGCCCGTGCAGCTGCCCGGCGCCTACAACGTCAACATCAAGTTGGACATCACCT |
| | CCCACAACGAGGACTACACCATCGTGGAACAGTACGAACGCGCCGAGGGCCGCCACTCCACCGGCGGCA |
| | TGGACGAGCTGTACAAGTCCGGACTCAGATCTCGAGCTCAAGCTTCGAATTCTGCAGTCGACGGTACCGCG |
| | GGCCCGGGATCCACCGGATCTAGATAACTGATCATAATCAGCCATACCACATTTGTAGAGGTTTTACTTGCTT |
| | TAAAAAACCTCCCACACCTCCCCCTGAACCTGAAACATAAAATGAATGCAATTGTTGTTGTTAACTTGTTTATTG |
| | CAGCTTATAATGGTTACAAATAAAGCAATAGCATCACAAATTTCACAAATAAAGCATTTTTTTCACTGCATTCTA |
| | GTTGTGGTTTGTCCAAACTCATCAATGTATCTTAACGCGTAAATTGTAAGCGTTAATATTTTGTTAAAATTCGCG |
| | TTAAATTTTTGATTTAAATGGCGCGCCGCCGTCACTGACCCAGTCAAAGGCACACAAGCAGCGACACCCAGGA |
| | GTGTGTTCCCACGACAGTCTAGCATGTAACTCAGAACCAAGAGTACTTAATAGTCCTGCCTGAAAACACCTGT |
| | ATTTTACGATCTTTCCCAAACTAAGGAGTTTAATAAACGTGAATATTCTTTTAGGTGTTTCAGTGTGATTAGTATA |
| | ACTGGCGGTGAAGCAACTGGAAGCTGGAATGCTTATCCTCAATCACAAAGAAAAGAAGCTGGGTACCAAAATT |
| | CTTTATTTGAAGAAATGGTACAAATTAAAGAACTTAAGCAGATGTTTTGGTGCAACTTATAGAAAAGATGAAGG |
| | CAGCCTGACATGCATGCACTGCCTCAGTGACCAGTAAAGTCACGTGGCTTTGGGGAAGTTAACGCAGAAGCA |
| | TGAATATATCTTGGTAATTTCCCATCTGATCGTTATGGAACTGTGCAGTAGAGGTAAAGGGATCATCAGGAA |
| | AAGGTTCCATGTAATTGAAGCTGGGGAAGTCAAGATTGTCCTCCAATTCATTCCAGAGTGGGTCAGATTGCA |
| | CCTCCAGATCGCACATAAATTCTGGGGAGGCAACGTGGTTGGAACCGCTAGTGTCAGTGTGCAGGTCGGG |
| | AACACTGTCAGATGTATCAAAATGCATCAAATCGTTCAAAGGCTGAGGTATGGGTGAAGTTGTAGTCATATT |
| | GTAGCCCATTGGACCGGTCTGCCCCAAAGTGGAAATAACTGGCAGTTGGTCTTCGAACTCGGGGTACTGTG |
| | TAATGGAGGTAGGCATTACCTTTCGTTTCTTCTTGGGAGGTCTCTGGGTGCCGGGGCACACGCCGTTGATCA |
| | GCAGAAAGGTGAATTCCTCGATATCCTGTTCCACGGTCAGCTGCTCGGTCAGCAGTCTGTACCAGCAGAAG |
| | CCGAAGATCATATCCAGCAGCAGTTCCCGGTTGGTGTCCTTGGGCAGCTCGCCGTTGCTGATGGCGTTTTC |
| | CACCAGTTTCTTGGGCATCTCTCTCCGCCGTTCCATGAACTGGTCCTTCAGCTGGGTCAGTGTGGCAGGGTC |
| | CAGCTGGGCCTCAGCGATCACGCATCTGAAGGCCTCGCCGCAGATGGTTTCCCGCCACACTTTCCACAGGT |
| | TCCGCAGCAGGAAGTCCAGATCGGCCTTGAAGCTGCCCAGGTCGGGGAACTTTCGGACCTGCTCGCTCTC |
| | GTTCTCGTACACCTCGGCGATCAGGGCGGCCTTGTTTGTCCACCACCGGTAGATGGTGGGCTTGGAGGCGC |

TABLE 1-continued

DNA sequences of example sTF-expression cassettes and reporter expression cassettes for testing the engineered plant-based transcription activation domains. The functional DNA parts are indicated: 8xsTF-specific binding site (black bolded text); core promoters (underlined text); mCherry coding region (black bolded underlined text); terminators (italics); and sTF (bolded italics) including the plant-based activation domain (bolded underlined italics).

| Example DNA sequences of the tested expression systems with selected activation domains | |
|---|---|
| | CAGCCCTTCTAGCCACAGACTCGATGCTCAGGCCGCTGTAGCCGCACTCTTTCAGGATCTCGATGGTGCTG |
| | GTCAGGATGGCCTTGTGGGTGTGGGGGCTTCTCAGAGATCCGATGCTGCTTCTGCTGGGGGTCCGGGCCAT |
| | GGCGGAATCCGGGTGGAGACTGAGCGCCGAAGCGGTCCTCTCCGCCGGTCCTGCAGCTGGGGGGGCAA |
| | CCTCCGCCGTAGGCACAGTAATTGGGTGATTTTGCTGTTCGTCATCACCACTAACGCTTCTATAGGGTAAAAA |
| | AACTCGGAGCTTATCAGCTATTGGTCTAAACTGGTGCCAATGGCGCGCCACGTCCGAGGGCGGCCGC |
| F | ATTTAAATAGGGCCCGTTTAAACCCGCTGATCAGCCTCGACAGTTTCCGGGGAGAAGTAGTATAGACTGGCCT |
| 8BS(McbR)- | GTCTAATTGACAAGCTTCAGATAGACTTGAGTGTCTAGGCTTATCTAGAGTCATAGACAGAGCAGTCTATCAC |
| Mm_Atp5bcp- | ATCCTAGGTCTATAGACGTTAACGTCTAACTAGCATAGACTCCGGAGTCTAATTGACAAGCTTCAGATAGACT |
| mCherry- | AGTCAGTCTAGGCTTATCTAGAGTCATAGACACGCTTGTCTATCACATCCTAGGTCTATAGACTGAATCGTCT |
| SV40t + | ACCTACTTGAGCAAATGCCTGATTGGCACCAGTTTAGACCAATAGCTGATAAGCTCCGAGTTTTTTACCCTAT |
| Mm_Eef2c | AGAAGCGTTAGTGGTGATGACGAACAGCAAAATCACCCAATTACTGTGCCTACGGCGGAGGTTGCCCCGCCC |
| p-McbR- | CAGCTGCAGGACCGGCGGAGAGGACCGCTTCGGCGCTCAGTCTCCACCCGGATTCCGCCATGGTGAGCAA |
| Bn- | GGGCGAGGAGGATAACATGGCCATCATCAAGGAGTTCATGCGCTTCAAGGTGCACATGGAGGGCTCCGTG |
| TAF1M- | AACGGCCACGAGTTCGAGATCGAGGGCGAGGGCGAGGGCCGCCCCTACGAGGGCACCCAGACCGCCAAG |
| Mn_FTH1t | CTGAAGGTGACCAAGGGTGGCCCCCTGCCCTTCGCCTGGGACATCCTGTCCCCTCAGTTCATGTACGGCTC |
| | CAAGGCCTACGTGAAGCACCCCGCCGACATCCCCGACTACTTGAAGCTGTCCTTCCCCGAGGGCTTCAAGT |
| | GGGAGCGCGTGATGAACTTCGAGGACGGCGGCGTGGTGACCGTGACCCAGGACTCCTCCCTGCAGGACG |
| | GCGAGTTCATCTACAAGGTGAAGCTGCGCGGCACCAACTTCCCCTCCGACGGCCCCGTAATGCAGAAGAA |
| | GACCATGGGCTGGGAGGCCTCCTCCGAGCGGATGTACCCCGAGGACGGCGCCCTGAAGGGCGAGATCAA |
| | GCAGAGGCTGAAGCTGAAGGACGGCGGCCACTACGACGCTGAGGTCAAGACCACCTACAAGGCCAAGAA |
| | GCCCGTGCAGCTGCCCGGCGCCTACAACGTCAACATCAAGTTGGACATCACCTCCCACAACGAGGACTAC |
| | ACCATCGTGGAACAGTACGAACGCGCCGAGGGCCGCCACTCCACCGGCGGCATGGACGAGCTGTACAAGT |
| | CCGGACTCAGATCTCGAGCTCAAGCTTCGAATTCTGCAGTCGACGGTACCGCGGGCCCGGGATCCACCGG |
| | ATCTAGATAACTGATCATAATCAGCCATACCACATTTGTAGAGGTTTTACTTGCTTTAAAAAACCTCCCACACCT |
| | CCCCCTGAACCTGAAACATAAAATGAATGCAATTGTTGTTGTTAACTTGTTTATTGCAGCTTATAATGGTTACAA |
| | ATAAAGCAATAGCATCACAAATTTCACAAATAAAGCATTTTTTTCACTGCATTCTAGTTGTGGTTTGTCCAAACT |
| | CATCAATGTATCTTAACGCGTAAATTGTAAGCGTTAATATTTTGTTAAAATTCGCGTTAAATTTTTGATTTAAATG |
| | GCGCGCCGCCGTCACTGACCCAGTCAAAGGCACACAAGCAGCGACACCCAGGAGTGTGTTCCCACGACAGT |
| | CTAGCATGTAACTCAGAACCAAGAGTACTTAATAGTCCTGCCTGAAAACACCTGTATTTTACGATCTTTCCCAA |
| | ACTAAGGAGTTTAATAAACGTGAATATTCTTTTAGGTGTTTCAGTGTGATTAGTATAACTGGCGGTGAAGCAAC |
| | TGGAAGCTGGAATGCTTATCCTCAATCACAAAGAAAAGAAGCTGGGTACCAAAATTCTTTATTTGAAGAAATGG |
| | TACAAATTAAAGAACTTAAGCAGATGTTTTGGTGCAACTTATAGAAAAGATGAAGGCAGCCTGACATGCATGCA |
| | CTGCCTCAGTGACCAGTAAAGTCACGTGGCTTTGGGGAAGTTAGTAAGGCTTTGGCATGTTATACATAAACAT |
| | ATCCTGAAGAGGAAACAACTGGTTACTACCTCCTCCACCGAAGGCAGTAGCATCTATATAGTTAAAACCGA |
| | AGTCGAGACTATTGTCGTCGTTTGCAGCTCCGCTCCAATCATCCCACAAGGGTTCAGATTGTACCTCTGAGG |
| | TGAACTCAGGTGAAACAACCTGCTCGGAACAGGAGGACTCTGTGGTATGCAAGTCAGGTACGCTATCTGAA |
| | GTATCAAAGTAAACGAAGTCATTAGGCATCACGGGGGGAGGTGGCATGCCCATCTCTACCTTTCGTTTCTTC |
| | TTGGGAGGGATAGAGTAGTCGGCAGGGGGGGCAGAGAGCAGCTGTCTGGCCAGATCTCTGGCGGTTTCCA |
| | GGGGGCTGATATTGTGCACCAGTCTGCTGCCGGCCAGGCCGCCATCCAGAAACACCAGCAGCTGGTTGGC |
| | CTGTGTGGTGCCAGGGTAGCCGTTCTTCTCGGTCAGCAGGTCGGTCAGGGTCTTGTGGCACCACTCTCTGT |
| | GTTCCAGCACGGCGGCCACAATGCCCTTCTCGCTATCGGTTTCGGGTCTGGGGTACTCGGAGGCGGCGTTC |
| | TGGAAGTGGCTGCCCCGGAAGTCCTTCTCGGGTTCTTCCTCGATGCACTGGTCGAAGAAGGCGATAATCTT |
| | GTCCTCGGGGTCCTTCATGCCCACGGTTCTTTCCCGCCAGGCTTCGCGCCACAGCTGGTCCAGGTTTTCCA |
| | GGTAGGCGATCACGAGGGCATCCTTGCTGCCGAACAGGCTGTACAGGCTGGCCTTGGCCACATCGGCCTC |
| | GCGCAGGATCCGGTCGATGCCGATCACTCTGATGCCCTCGGTGGTGAACAGGTTGGTGGCGCTGTCCAGC |
| | AGTCTCTGTCTAGGGCTGGGTCTGTTTCTCCGCCGGTTGGCGCCAGCGCTTGTTTTGCTCTTGCCGCTGGCG |
| | CTGGCGGCCATGGTGGCGGATGGCGACGGATTCTCAGAGTCAGAGGTGAACAGGGAAGCGCGCCGACGAT |
| | GGCGGCGGCTGCGGCGGAAGAGACCGCTGACGTCAACGCCCGGCCTTTTATAGGTCAACGCCGGTTGGGTG |
| | CGTCACGTGACGGCGCCGGGTGCTCGTCCGGGGCGCGCCACGTCCGAGGGCGGCCGC |

Example 2

Mutagenesis of the Selected Activation Domains to Improve their Activity

To increase the activity of plant-based transcription activation domains, rational mutagenesis was performed on two selected activation domains derived from transcription factors found in edible plant species: spinach (*Spinacia oleracea*) and rapeseed/canola (*Brassica napus*). The So_NAC102-AD and Bn_TAF1-AD (Example 1) contain significant amounts of acidic (glutamate and aspartate) and hydrophobic (leucine, isoleucine, phenylalanine) amino acids, which indicates that they could belong to a group of acidic/hydrophobic transcription activation domains, which are typically enriched with these types of amino acids. There are, however, some basic amino acids (lysine and arginine) present in the native sequences of these activation domains. Some of these amino acids were mutated (and other changes were introduced) to modify the sequences of these selected activation domains to gain more pronounced acid/hydrophobic pattern. Two novel activation domains were designed:

So_NAC102M (SEQ ID NO: 10)-AD=So_NAC102-AD with following amino-acid changes: Removal (deletion) of amino acids 1-3, and mutations K18L, K44L, R58D, C59L, K78L, K85L, and K91 D.

Bn_TAF1M (SEQ ID NO: 11)-AD=Bn_TAF1-AD with following amino-acid changes: K25D, K51 L, K53D, K62D.

The new activation domains were tested in the setup identical to the Example 1, following the same steps. The domains were implemented in the reporter expression system (FIG. 1), and the fluorescence of the *T. reesei* strains containing the corresponding reporter expression systems was analyzed and it is shown in FIG. 4. It was demonstrated that the modifications introduced into So_NAC102-AD and Bn_TAF1-AD resulted in significantly more active activation domains, So_NAC102M-AD and Bn_TAF1M-AD.

Example 3

Production of Prokaryotic Xylanase in *Trichoderma reesei* by Synthetic Expression System Containing Plant-Derived Activation Domains The five best performing expression systems containing plant-based activation domains according to the results presented in FIG. 4 (marked with an arrow), as well as the expression systems with So_NAC102-AD and Bn_TAF1-AD, were compared to the expression system containing the VP16-AD (as a benchmark control). The comparison was performed in experiments where an example heterologous protein product was produced (secreted into medium) by *Trichoderma reesei*. The expression systems described in Example 1 and Example 2 were modified by the replacement of the mCherry coding sequence by the DNA sequence encoding an alkaline xylanase (thermo-stable mutated version xynHB_N188A SEQ ID NO: 31) of *Bacillus pumilus* origin previously produced in *Pichia pastoris* (Lu, Y. et al. 2016, Scientific Reports volume 6, Article number: 37869). The xylanase coding DNA was codon-optimized for *Trichoderma reesei* and an appropriate secretion signal sequence (SS) with the Kex2 recognition site was added in-frame into its 5'-end. This resulted in a DNA encoding a fusion protein (SS-Kex2-xynHB_N188A; target gene in FIG. 1), which can be efficiently processed and secreted into a medium by *T. reesei*.

The xylanase expression cassettes were transformed into *T. reesei* by the protocol described in Example 1. *Trichoderma reesei* strain M1909 was used as the parental strain, and the DNA was transformed into the *T. reesei* protoplasts by the CRISPR-Cas9 protein transformation protocol. The selection of the transformed colonies and the analysis of the strains was done as described above (in Example 1), except the xynHB_N188A gene instead of the mCherry gene was targeted in qPCR analysis.

The xylanase production was tested in small-scale liquid cultures and analyzed in the culture supernatants by SDS-PAGE (FIG. 5). Four mL of the YE-glc medium (20 g/L glucose, 10 g/L yeast extract, 15 g/L $KH_2PO_4$, 5 g/L $(NH_4)_2SO_4$, 1 mL/L trace elements (3.7 mg/L $COCl_2$, 5 mg/L $FeSO_4·7H_2O$, 1.4 mg/L $ZnSO_4·7H_2O$, 1.6 mg/L $MnSO_4·7H_2O$), 2.4 mM $MgSO_4$, and 4.1 mM $CaCl_2$, pH adjusted to 4.8) in 24-well cultivation plates was inoculated by the conidia of the selected clones collected from the PDA plates. The cultures were incubated at 28° C. at 800 rpm (Infors HT Microtron) for 3 days, and centrifuged to pellet the mycelium. One hundred μL of each culture supernatant was mixed with 50 μL of 4×SDS-loading buffer (400 mL/L Glycerol; 240 mM Tris·HCl pH=6.8; 80 g/L SDS; 0.4 g/L bromophenol blue; and 50 mL/L β-mercaptoethanol), and incubated at 95° C. for 4 minutes. Fifteen μL of the mixture was loaded on the 4-20% SDS-PAGE gradient gel next to the molecular weight standard. After complete protein separation in an electric field (PowerPac HC; BioRad), the gel was stained with colloidal coomassie stain (PageBlue Protein Staining Solution; THERMO FISHER SCIENTIFIC®) according to the manufacture's protocol. The visualization of the stained gel was performed on the ODYSSEY® CLx Imaging System instrument (LI-COR® Biosciences). The scan of the stained gel is shown in FIG. 5. The relative amount of xylanase produced somewhat corresponded to the mCherry fluorescence levels shown in FIG. 4; the best performing expression systems with the plant-based activation domains were So_NAC102M- and Bn_TAF1M-containing systems. The two corresponding strains, and the strain producing xylanase with the expression system containing VP16-AD, were tested in a 1 L bioreactor setup for the assessment of the xylanase production.

The 1 L bioreactor cultivations were carried out in the Sartorius Stedim BIOSTAT® Q Plus Fermentor Bioreactor System. Pre-cultures (inoculated by conidia) were grown for 24 hours in 100 mL of YE-glc medium to produce sufficient amount of mycelium for bioreactor inoculations. The bioreactor cultivations were started by inoculating 80 mL of the pre-culture into 800 mL of the YE-glucose medium (10 g/L glucose, 20 g/L yeast extract, 5 g/L $KH_2PO_4$, 5 g/L $NH_4SO_4$, 1 mL/L trace elements, 2.4 mM $MgSO_4$, and 4.1 mM $CaCl_2$), 1 mL/L Antifoam J647, pH 4.8). These cultures were continuously fed with 500 g/L glucose (with WATSON-MARLOW® 120 U/DV peristaltic pump at flow rate 0.3-0.7 rpm), air flow at 0.5 slpm (0.4-0.6 vvm), and stirring at 900-1200 rpm. The cultivation was carried out for 6 days, samples taken every day. A subset of the culture supernatants was analyzed by SDS-PAGE (FIG. 6), and for the xylanase activity (FIG. 7).

Equivalent of 2 μL of different time-points culture supernatants from each culture was loaded on a gel (4-20% gradient) and the proteins were separated in in an electric field (PowerPac HC; BioRad). The gel was stained with colloidal coomassie (PageBlue Protein Staining Solution; THERMO FISHER SCIENTIFIC®), and the visualization was performed on the ODYSSEY® CLx Imaging System instrument (LI-COR® Biosciences). The scan of the stained gel is shown in FIG. 6. The xylanase seemed to be produced equally well in all three strains, demonstrating the utility of the selected plant-based activation domains in possible replacement of the viral-based VP16 activation domain for the heterologous protein production in *Trichoderma reesei*.

The culture supernatants from xylanase production bioreactor cultures (day 5 and day 6), and a culture supernatant from a bioreactor culture performed under same conditions with *T. reesei* strain not containing the xylanase production expression system (day 6, negative control—NC in FIG. 7) were serially diluted in 50 mM Tris·HCl (pH 8.0), and assayed for the xylanase activity by EnzCheck® Ultra Xylanase Assay Kit (INVITROGEN®). Fifty μL of the culture supernatant dilutions were mixed with 50 μL of 50 μg/mL xylanase substrate (component A of the kit) solution in 50 mM Tris·HCl (pH 8.0) in black 96-well plates (Black Cliniplate; THERMO SCIENTIFIC®). The reactions were incubated in dark for 25 minutes at room temperature. The fluorescence of the xylanase reaction product (released by the action of the xylanase from the substrate) was measured using the VARIOSKAN® (Thermo Electron Corporation) fluorometer. The settings for the measurement were 358 nm (excitation) and 455 nm (emission), respectively. The activity was calculated and expressed in arbitrary units per mL of the culture supernatant (AU/mL). The obtained xylanase activities are shown in FIG. 7. Also these results clearly indicate that the selected plant-based activation domains can be successfully used instead of the viral-based VP16 AD for expression of heterologous genes without loss of the expression levels. In fact, the xylanase activity in supernatants from cultures with strains containing the plant-based ADs in the expression systems seems higher than the corresponding activity from the VP16-control (day 5, FIG. 7). In addition, the results clearly indicate that the xylanase protein produced in *Trichoderma reesei* is functional catalytically active enzyme.

Example 4

Production of Prokaryotic Phytase in *Pichia pastoris* by Synthetic Expression System Containing Plant-Derived Activation Domains The five best performing plant-based activation domains according to the results presented in FIG. 4 (marked with an arrow) and the VP16-AD (as a benchmark control) were selected for construction of synthetic expression systems for *Pichia pastoris*. The comparison of these genetic constructs (transcription activation domains) was performed in experiments where an example heterologous protein product was produced (secreted into medium) by *Pichia pastoris*. The expression systems (FIG. 2) were constructed as two separate DNA molecules (plasmids).

The first DNA was composed of: 1) sTF expression cassette; 2) selection marker (SM) expression cassette, 3) genome integration DNA regions (flanks); and 4) regions needed for propagation of the plasmids in *E. coli*. The sTF expression cassette was consisting of a core promoter (An_008cp SEQ ID NO: 22), a sTF coding sequence, and a terminator (see Table 1C and 1 D for example sequences of sTF expression cassettes used in *Pichia pastoris*). The sTF gene was encoding a fusion protein (synthetic transcription factor) composed of bacterial DNA binding protein, Bm3R1, whose encoding DNA sequence was codon-optimized for *Saccharomyces cerevisiae*, nuclear localization signal SV40 NLS, short peptide linker, and the transcription activation domain (AD). The activation domains encoding DNA sequences were codon optimized for *Pichia pastoris*. The control AD was the VP16-AD. The terminator was the *Trichoderma reesei* tef1 terminator (Tr_TEF1t). The SM cassette was the expression cassette allowing expression of the kanR gene (encoding aminoglycoside phosphotransferase enzyme) in *Pichia pastoris* using a suitable promoter and terminator. The genome integration DNA regions (flanks) were used to allow integration of the construct into the URA3 locus of *P. pastoris* (JGI38543; genome.jgi.doe.gov/Picpa1/Picpa1.home.html). The URA3-integration flanks contained DNA sequences corresponding to outside DNA regions of the URA3 coding region: URA3-5' was a sequence 500 to 1 bp upstream of the start codon; URA3-3' was a sequence 1 to 499 bp downstream of the stop codon.

The second DNA was composed of: 1) target gene expression cassette; 2) selection marker (SM) expression cassette; 3) genome integration DNA regions (flanks); and 4) regions needed for propagation of the plasmids in *E. coli*. The target gene expression cassette contained eight Bm3R1-biding sites (BS; sequences shown in Table 1A and 1B); An_201 core promoter (An_201cp SEQ ID NO: 23; sequence shown in Table 1A and 1B); target gene encoding DNA (target gene); and the *Saccharomyces cerevisiae* ADH1 terminator (Sc_ADH1t). The target gene was a DNA sequence encoding a phytase enzyme (thermo-stable mutated version AppA_K24E amino acid SEQ ID NO: 24) of *Escherichia coli* origin previously produced in *Pichia pastoris* (Zhang J. et al, 2016, Biosci. Biotech. Res. Comm. 9(3): 357-365). The phytase coding DNA was codon-optimized for *Pichia pastoris* and an appropriate secretion signal sequence (SS) with the Kex2 recognition site was added in-frame into its 5'-end. This resulted in a DNA encoding a fusion protein (SS-Kex2-AppA_K24E; target gene in FIG. 2), which can be efficiently processed and secreted into a medium by *P. pastoris*. The SM cassette was the expression cassette allowing expression of the URA3 gene (encoding orotidine 5'-phosphate decarboxylase enzyme) in *Pichia pastoris* using a suitable promoter and terminator. The genome integration DNA regions (flanks) were used to allow integration of the construct into the AOX2 locus of *P. pastoris* (JG139494; genome.jgi.doe.gov/Picpa1/Picpa1.home.html). The AOX2-integration flanks contained DNA sequences corresponding to DNA regions within and outside of the AOX2 coding region: AOX2-5' was a sequence 504 to 6 bp upstream of the start codon; AOX2-3' was a sequence starting at bp 1806 of the coding region and ending at bp 313 after the stop codon.

Each cassette was integrated into separate loci of the *P. pastoris* genome. The transformations were done sequentially; first, the sTF expression cassette-containing constructs were integrated into the *P. pastoris* parental strain forming the sTF-background strains; and then the target gene expression cassette-containing construct was integrated into the sTF-background strains forming the final production strains.

*Pichia pastoris* strain Y-11430 (currently also called *Komagataella phafii*, the strain obtained from NRRL Culture Collection) was used as the parental strain. The sTF-expression-cassette-containing constructs (FIG. 2) were integrated into URA3 locus (replacing the native coding region) using the corresponding flanking regions for homologous recombination. The transformations were done by using the CRISPR-Cas9-protein transformation protocol: Isolated *P. pastoris* protoplasts were suspended into 600 μL of STC solution (1.33 M sorbitol, 10 mM Tris-HCl, 50 mM $CaCl_2$, pH 8.0). For each transformation, one hundred μL of protoplast suspension was mixed with 5 μg of donor DNA (linear fragment corresponding to the construct shown in FIG. 2) and 50 μL of URA3-targeting RNP-solution (1 μM Cas9 protein (IDT), 1 μM synthetic crRNA (IDT), and 1 μM tracrRNA (IDT)) and 100 μL of the transformation solution (25% PEG 6000, 50 mM $CaCl_2$, 10 mM Tris-HCl, pH 7.5). The mixture was incubated on ice for 20 min. Two mL of transformation solution was added and the mixture was incubated 5 min at room temperature. Four mL of STC was added followed by addition of 7 mL of the molten (50° C.) top agar (200 g/L D-sorbitol, 20 g/L bacto peptone, 10 g/L yeast extract, 1 g/L uracil, 20 g/L D-glucose, 500 mg/L G418, and 20 g/L agar). The mixture was poured onto selection plates (200 g/L D-sorbitol, 20 g/L bacto peptone, 10 g/L yeast extract, 1 g/L uracil, 20 g/L D-glucose, 500 mg/L G418, and 20 g/L agar). Cultivation was done at 30° C. for five or seven days, until the colonies appeared. The colonies were picked and re-cultivated on YPD-G418 selection plates (20 g/L bacto peptone, 10 g/L yeast extract, 1 g/L uracil, 20 g/L D-glucose, 500 mg/L G418, and 20 g/L agar).

The transformed clones were first tested for growth in absence of uracil, and those not able to grow were analyzed by qPCR. The genomic DNA of each selected strain was isolated and used as a template DNA in qPCR reactions. The qPCR signal of the sTF gene (Bm3R1) was compared to a qPCR signal of a unique native sequence in each strain. In addition, the correct deletion of the URA3 gene was confirmed by absent qPCR signal of the URA3 target. Strains with correct URA3 deletions and single-copy sTF cassette integrated in the genome (sTF-background strains) were selected for second round of transformations.

The second transformation was done by a lithium-acetate protocol: The sTF-background strains were cultivated in YPD+URA medium (20 g/L bacto bacto peptone, 10 g/L yeast extract, 1 g/L uracil, 20 g/L D-glucose) to reach OD600=0.6-1.0. Fifty mL of each culture was centrifuged, the cell pellet was washed with water and then with LiAc/TE solution (100 mM lithium acetate; 10 mM Tris·HCl (pH=7.5); 1 mM EDTA). The washed cell pellets were resuspended in 0.5 mL of LiAc/TE solution. Fifty μL of the cell suspension was mixed with 10 μg of the AppA-expression construct DNA (linear AppA-target gene expression cassette fragment corresponding to the construct shown in FIG. 2), and with 400 μL of LiAc transformation solution (40% polyethylene glycol 4000 (PEG-4000); 100 mM lithium acetate; 10 mM Tris·HCl (pH=7.5); 1 mM EDTA; 400 μg/mL herring sperm DNA). The mixtures were incubated at 30° C. for 30 minutes, and then at 42° C. for 20 minutes. The transformation mix was centrifuged, the cell pellet resuspended in 200 μL of water and plated on SCD-URA plates (6.7 g/L of yeast nitrogen base (YNB, Becton, Dickinson and Company), synthetic complete amino acid without uracil, 20 g/L D-glucose, and 20 g/L agar). Cultivation was done at 30° C. for three or five days, until the colonies appeared. The colonies were picked and re-cultivated on SCD-URA plates.

The genomic DNA of each selected clone was isolated and used as a template DNA in qPCR reactions. The qPCR signal of the target gene (AppA) was compared to a qPCR signal of a unique native sequence in each strain. Strains with single-copy target-gene-cassette cassette integrated in the genome were used in phytase production experiments.

The phytase production was tested in small-scale liquid cultures and analyzed in the culture supernatants by SDS-PAGE (FIG. 8). Four mL of the BMG medium (20 g/L glucose, 10 g/L yeast extract, 20 g/L bacto peptone, 13.4 g/L YNB, 0.4 mg/L Biotin, and 100 mM $KH_2PO_4$ pH=6.0) in 24-well cultivation plates was inoculated by the cells of the selected clones. The cultures were incubated at 28° C. at 800 rpm (Infors HT Microtron) for 2 days, and then centrifuged to pellet the cells. One hundred μL of each culture supernatant was mixed with 50 μL of 4× SDS-loading buffer (400 mL/L Glycerol; 240 mM Tris·HCl pH=6.8; 80 g/L SDS; 0.4 g/L bromophenol blue; and 50 mL/L β-mercaptoethanol), and incubated at 95° C. for 4 minutes. Fifteen μL of the mixture was loaded on the 4-20% SDS-PAGE gradient gel next to the molecular weight standard. After complete protein separation in an electric field (PowerPac HC; BioRad), the gel was stained with colloidal coomassie stain (PageBlue Protein Staining Solution; THERMO FISHER SCIENTIFIC®) according to the manufacture's protocol. The visualization of the stained gel was performed on the ODYSSEY® CLx Imaging System instrument (LI-COR® Biosciences). The scan of the stained gel is shown in FIG. 8. Based on the results it seemed that the best performing expression systems with the plant-based activation domains were So_NAC102M- and Bn_TAF1M-containing systems. The two corresponding strains, and the strain producing the phytase with the expression system containing VP16-AD, were tested in a 1 L bioreactor setup for the assessment of the phytase production.

The 1 L bioreactor cultivations were carried out in the Sartorius Stedim BIOSTAT® Q Plus Fermentor Bioreactor System. Pre-cultures were grown for 24 hours in 100 mL of BMG medium to produce sufficient amount of biomass for bioreactor inoculations. The bioreactor cultivations were started by inoculating 80 mL of the pre-culture into 800 mL of the BMG medium containing 1 mL/L Antifoam J647. These cultures were continuously fed with 500 g/L glucose (with WATSON-MARLOW® 120 U/DV peristaltic pump at flow rate 0.3-0.7 rpm), air flow at 0.5 slpm (0.4-0.6 vvm), and stirring at 900-1200 rpm. The cultivation was carried out for 6 days, samples taken every day. The culture supernatants was analyzed by SDS-PAGE (FIG. 9), and for the phytase activity (FIG. 10).

Equivalent of 2 μL of different time-points culture supernatants from each culture was loaded on a gel (4-20% gradient) and the proteins were separated in in an electric field (PowerPac HC; BioRad). The gel was stained with colloidal coomassie (PageBlue Protein Staining Solution; THERMO FISHER SCIENTIFIC®), and the visualization was performed on the ODYSSEY® CLx Imaging System instrument (LI-COR® Biosciences). The scan of the stained gel is shown in FIG. 9. The AppA_K24E phytase seemed to be produced equally well in all three strains, demonstrating the utility of the selected plant-based activation domains in possible replacement of the viral-based VP16 activation domain for the heterologous protein production in *Pichia pastoris*.

The culture supernatants from the phytase production bioreactor cultures (day 4 and day 6), and a culture supernatant from a bioreactor culture performed under same conditions with *P. pastoris* strain not containing the phytase production expression system (negative control—NC in FIG. 10) were subjected to a gel filtration to remove phosphate, which would interfere with the phytase assay. The gel filtration was performed on PD-10 desalting columns (Bio-Rad) with 100 mM Na-acetate (pH 4.7). The eluent from the gel-filtration was assayed for the phytase activity by the Phytase Assay Kit (MyBioSource). Fourteen μL of the eluent diluted in phytase reaction buffer was combined with 56 μL of the substrate solution (containing phytic acid; reagent #1 of the kit) in a transparent 96-well plate (THERMO SCIENTIFIC®), and incubated for 30 min at 37° C. Seventy μL of the reaction ter-mination solution (reagent #2 of the kit) was added, followed by addition of 70 μL of the color development solution. The solutions were mixed and incubated for 10 min at room temperature. The absorbance of the phosphomolybdate complex (phytase reaction product released by the action of the phytase from the phytic acid conjugated to molybdate) was measured using the VARIOSKAN® (Thermo Electron Corporation) instrument. The absorbance of the solutions were determined at 700 nm. The activity was calculated and expressed in arbitrary units per mL of the culture supernatant (AU/mL). The obtained phytase activities are shown in FIG. 10. These results clearly indicate that the selected plant-based activation domains can be successfully used instead of the viral-based VP16 AD for expression of heterologous genes without loss of the expression levels in *Pichia pastoris*. In addition, the results clearly indicate that the phytase protein produced is functional catalytically active enzyme.

Example 5

Production of Prokaryotic Xylanase in *Myceliophthora thermophila* by Synthetic Expression System Containing the Plant-Derived Activation Domains The two best performing plant-based activation domains (So_NAC102M and Bn_TAF1M) according to the results presented in FIG. 5, FIG. 6, FIG. 7, FIG. 8, and FIG. 9, were compared to the VP16-AD in an experiment where an example heterologous protein product was produced (secreted into medium) by *Myceliophthora thermophila*. The expression systems described in Example 3, xylanase expression cassettes containing So_NAC102M-AD, Bn_TAF1M-AD, or VP16-AD, were modified by the replacement of the pyr4 selection marker (SM) expression cassette with the hygR selection marker (SM) expression cassette allowing expression of the hygR gene (encoding Hygromycin-B 4-O-kinase) in *Myceliophthora thermophila.*

*Myceliophthora thermophila* strain D-76003 (also called *Thielavia heterothallica*, VTT culture collection) was used as the parental strain, and the DNA was transformed into the *M. thermophila* protoplasts by the PEG transformation protocol: Isolated *M. thermophila* protoplasts were suspended into 400 µL of STC solution (1.33 M sorbitol, 10 mM Tris-HCl, 50 mM $CaCl_2$), pH 8.0). For each transformation, one hundred µL of protoplast suspension was mixed with 30 µg of the expression construct DNA dissolved in <100 µL of solution (linear fragment corresponding to the construct shown in FIG. 1) and with 100 µL of the transformation solution (25% PEG 6000, 50 mM $CaCl_2$), 10 mM Tris-HCl, pH 7.5). The mixture was incubated on ice for 20 min. Two mL of transformation solution was added and the mixture was incubated 5 min at room temperature. Four mL of STC was added followed by addition of 7 mL of the molten (50° C.) top agar (200 g/L D-sorbitol, 20 g/L D-glucose, 20 g/L bacto peptone, 10 g/L yeast extract, 200 mg/L hygromycin-B; and 20 g/L agar). The mixture was poured onto a selection plate (200 g/L D-sorbitol, 20 g/L D-glucose, 20 g/L bacto peptone, 10 g/L yeast extract, 200 mg/L hygromycin-B; and 20 g/L agar). Cultivation was done at 35° C. for four to seven days, colonies were picked and re-cultivated on the YPD-HYG plates (20 g/L D-glucose, 20 g/L bacto peptone, 10 g/L yeast extract, 200 mg/L hygromycin-B; and 20 g/L agar).

Four clones from each transformation were selected for small-scale liquid cultures and analysis of the culture supernatants by SDS-PAGE (FIG. 8). Four mL of the BMG medium (20 g/L glucose, 10 g/L yeast extract, 20 g/L bacto peptone, 13.4 g/L YNB, 0.4 mg/L Biotin, and 100 mM $KH_2PO_4$ pH=6.0) in 24-well cultivation plates was inoculated by the mix of mycelium and conidia collected from the clones growing on the YPD-HYG plates. The cultures were incubated at 35° C. at 800 rpm (Infors HT Microtron) for 3 days, and then centrifuged to pellet the mycelium. One hundred µL of each culture supernatant was mixed with 50 µL of 4× SDS-loading buffer (400 mL/L Glycerol; 240 mM Tris·HCl pH=6.8; 80 g/L SDS; 0.4 g/L bromophenol blue; and 50 mL/L β-mercaptoethanol), and incubated at 95° C. for 4 minutes. Fifteen µL of the mixture was loaded on the 4-20% SDS-PAGE gradient gel next to the molecular weight standard. After complete protein separation in an electric field (PowerPac HC; BioRad), the gel was stained with colloidal coomassie stain (PageBlue Protein Staining Solution; THERMO FISHER SCIENTIFIC®) according to the manufacture's protocol. The visualization of the stained gel was performed on the ODYSSEY® CLx Imaging System instrument (LI-COR® Biosciences). The scan of the stained gel is shown in FIG. 11. There is a large variability in the xylanase production levels between the individual clones, which is a result of a random DNA integration (transformed DNA is not targeted into a specific genomic locus). In this type of transformation, the expression cassettes are typically integrated in one or more integration events into diverse unknown genomic loci. However, the range of the obtained xylanase production levels, and especially the maximal xylanase production in specific clones, indicates that the plant-based activation domains (So_NAC102M, and Bn_TAF1M) can provide similar, or higher level expression of heterologous genes than the viral-based VP16 AD. Therefore, it is evident that the plant-based activation domains can be successfully used instead of the virus-based activation domains for recombinant protein production in *Myceliophthora thermophila.*

The culture supernatants from cultures of *M. thermophila* strains transformed by the xylanase expression constructs, and a culture supernatant from a culture performed under same conditions with the parental *M. thermophila* strain (NC in FIG. 12) were serially diluted in 50 mM Tris·HCl (pH 8.0), and assayed for the xylanase activity by EnzCheck® Ultra Xylanase Assay Kit (INVITROGEN®). Fifty µL of the culture supernatant dilutions were mixed with 50 µL of 50 µg/mL xylanase substrate (component A of the kit) solution in 50 mM Tris·HCl (pH 8.0) in black 96-well plates (Black Cliniplate; THERMO SCIENTIFIC®). The reactions were incubated in dark for 25 minutes at room temperature. The fluorescence of the xylanase reaction product (released by the action of the xylanase from the substrate) was measured using the VARIOSKAN® (Thermo Electron Corporation) fluorometer. The settings for the measurement were 358 nm (excitation) and 455 nm (emission), respectively. The activity was calculated and expressed in arbitrary units per mL of the culture supernatant (AU/mL). The obtained xylanase activities are shown in FIG. 12. These results closely correlate with the results presented in FIG. 11, clearly indicating that the xylanase protein produced in *Myceliophthora thermophila* is functional catalytically active enzyme.

Example 6

Test of the Selected Plant-Derived Activation Domains in CHO Cells (*Cricetulus griseus*)

The two best plant-based activation domains based on fungal experiments, So_NAC102M and Bn_TAF1M, are used to construct artificial expression systems for the CHO cells (*Cricetulus griseus*) (see Table 1E and 1F for example sequences of the expression cassettes for CHO cells). The CHO K1 cell line is transformed with a plasmid comprising eight sTF-specific binding sites (8 BS) positioned upstream of a core promoter Mm_Atp5Bcp (SEQ ID NO: 26). The target gene, mCherry, is positioned right after the core promoter. The transcription of the mCherry is terminated at the SV40 terminator. Adjacent to mCherry expression cassette, in opposite direction, there is the sTF expression cassette, which consist of a core promoter Mm_Eef2cp (SEQ ID NO: 27), the PhlF repressor, a nuclear localization signal, the SV40 NLS, and the transcription activation domain (AD) of plant origin. The transcription of the sTF gene is terminated on the terminator sequence FTH1 terminator of *Mus musculus* origin. The plasmid contains also a pac gene encoding puromycin N-acetyltransferase enzyme giving resistance to puromycin antibiotics. The performance of these expression systems are compared to the expression system using the CMV (cytomegalovirus) promoter for the expression of mCherry, and to the artificial expression system where the VP64 activation domain (of herpes simplex virus origin) (SEQ ID NO: 30) is used instead of plant-based ADs.

CHO-K1 cells are maintained in RPMI media (Thermo Fischer) supplemented with 2 mM L-glutamine, 10% fetal bovine serum and penicillin streptomycin solution to a final concentration of 100 units penicillin and 0.1 g/l streptomycin. Cells are grown at 37° C. in presence of 5% $CO_2$. The day before transfection 70-80% con-fluent CHO cells are washed with PBS, pH ~7.4 and after that trypsinized for by adding 2 mL of trypsin into cultures in 250 mL, 75 $cm^2$ flasks and incubating them in +37° C. for 2-4 minutes until the cells have dissociated. Eight mL of fresh RPMI media with the above mentioned supplements is added into flask. One hundred µL of the cell solution is pipetted on to each well of a 24 well plate containing 400 µL of RPMI media (1/5 dilution) supplemented with 2 mM L-glutamine, 10% fetal bovine serum and penicillin streptomycin solution to a final concentration of 100 units penicillin and 0.1 g/l streptomycin. The following day the media is removed by pipetting and replaced immediately with 400 μL of fresh RPMI media without antibiotic supplements. Cells are incubated for 20 minutes in 37° C. with 5% $CO_2$. For each transfection, two μL of Lipofectamine LTX (Thermo Fischer) is combined with 25 μL of Opti-MEM medium (Thermo Fischer), and 0.5-1 μg of plasmid DNA is combined with 0.5 μL of Plus reagent (provided with the Lipofectamine LTX reagent) and 25 μL of Opti-MEM medium. Opti-MEM diluted DNA is then mixed with diluted Lipofectamine® LTX reagent, and incubated for 5 minutes in room temperature. DNA-lipid complex is immediately added to the CHO cell by slow pipetting on top of each culture. The cells are incubated for 1-2 days in 37° C. in presence of 5% $CO_2$. The expression of mCherry can by visualized and analyzed by fluorescent microscopy or by flow-cytometry. For selection of stably transfected cells, the media is replaced by puromycin (1-10 μg/mL) supplemented RPMI medium 2-4 days after transfection.

Example 7

Production of Bovine β-Lactoglobulin B Protein (LGB) in *Aspergillus oryzae* by Synthetic Expression System Containing the Plant-Derived Activation Domain The expression system containing one example plant-based activation domain, Bn_TAF1M-AD (SEQ ID NO: 11), was constructed and tested in *Aspergillus* oryzae for the production of an example heterologous protein product secreted into the culture medium. The expression system described in Example 2 (and its scheme shown in FIG. 1), containing the Bn_TAF1M-AD, was modified by the replacement of the mCherry coding sequence by the DNA sequence encoding a bovine β-Lactoglobulin B protein (LGB SEQ ID NO: 29). The LGB coding DNA was extended by an appropriate secretion signal sequence (SS) with the Kex2 recognition site added in-frame into its 5'-end. This resulted in a DNA encoding a fusion protein (SS-Kex2-LGB; target gene in FIG. 1), which can be efficiently processed and secreted into a medium by *A. oryzae*. The expression system was also further modified by providing an *A. oryzae*-specific selection marker (SM in FIG. 1) and the genome-integration DNA regions (shown as EGL1-5' and EGL1-3' in FIG. 1) for targeting selected *A. oryzae* genomic loci. The selection marker was the pyrG gene of *A. oryzae* with suitable promoter and terminator regions. The genome-integration DNA regions were chosen to allow integration of the construct into the gaaC locus of *A. oryzae*—AO090011000868 (fungi.ensembl.org/). The gaaC-integration flanks contained DNA sequences corresponding to the outside DNA regions of the gaaC coding region in the genome: The gaaC-5' was a sequence spanning from 600 bp upstream of the start codon to 15 bp downstream of the start codon; the gaaC-3' was a sequence 1 to 600 bp downstream of the stop codon. Another set of genome-integration DNA regions were chosen to allow integration of the construct into the gluC locus of *A. oryzae*—AO090701000403 (fungi.ensembl.org/). The gluC-integration flanks contained DNA sequences corresponding to outside DNA regions of the gluC coding region in the genome: The gluC-5' was a sequence 600 to 29 bp upstream of the start codon; gluC-3' was a sequence 1 to 600 bp downstream of the stop codon. Therefore, two LGB expression cassettes were constructed: One targeted into the gaaC locus and the other into gluC locus of *A. oryzae*.

*Aspergillus oryzae* strain D-171652 (VTT culture collection) was used as a parental strain. This strain was first modified by deleting two genes: the AO090011000868 gene (fungi.ensembl.org/) encoding the orotidine 5'-phosphate decarboxylase (pyrG) enzyme, and the A0090120000322 gene (fungi.ensembl.org/) encoding homolog of NHEJ complex subunit (lig4) protein. The resulting strain (called here *A. oryzae* pyrGΔ/lig4Δ) is not able to grow in absence of uracil and it is defective in non-homologous end-joining DNA-repair pathway.

The two LGB-expression cassettes were transformed into the protoplasts prepared from the *A. oryzae* pyrGΔ/lig4Δ strain by the PEG transformation protocol: Isolated *A. oryzae* pyrGΔ/lig4Δ protoplasts were suspended into 400 μL of STC solution (1.33 M sorbitol, 10 mM Tris-HCl, 50 mM $CaCl_2$), pH 8.0). For the transformation, one hundred μL of protoplast suspension was mixed with 20 μg of the LGB expression construct with the gaaC-genome-integration flanks dissolved in 50 μL of solution (linear fragment corresponding to the construct shown in FIG. 1, where the EGL1-5' and EGL1-3' regions are replaced with gaaC-5' and gaaC-3' regions), 20 μg of the LGB expression construct with gluC-genome-integration flanks dissolved in 50 μL of solution (linear fragment corresponding to the construct shown in FIG. 1, where the EGL1-5' and EGL1-3' regions are replaced with gluC-5' and gluC-3' regions), and with 100 μL of the transformation solution (25% PEG 6000, 50 mM $CaCl_2$), 10 mM Tris-HCl, pH 7.5). The mixture was incubated on ice for 20 min. Two mL of transformation solution was added and the mixture was incubated 5 min at room temperature. Four mL of STC was added followed by addition of 7 mL of the molten (50° C.) top agar (200 g/L D-sorbitol, 6.7 g/L of yeast nitrogen base (YNB, Becton, Dickinson and Company), synthetic complete amino acid without uracil; and 20 g/L agar). The mixture was poured onto a selection plate (200 g/L D-sorbitol, 20 g/L D-glucose, 6.7 g/L of yeast nitrogen base (YNB, Becton, Dickinson and Company), synthetic complete amino acid without uracil; and 20 g/L agar). Cultivation was done at 28° C. for four to seven days; colonies were picked and re-cultivated on the SDC-URA plates (6.7 g/L of yeast nitrogen base (YNB, Becton, Dickinson and Company), synthetic complete amino acid without uracil, 20 g/L D-glucose, and 20 g/L agar).

Transformed strains were tested by qPCR of the genomic DNA isolated from the strains. The qPCR signal of the LGB gene was compared to a qPCR signal of a unique native sequence in each strain. In addition the correct simultaneous deletion of the gaaC and gluC genes was confirmed by absent qPCR signal of the gaaC and gluC targets. Four correct selected strains were sporulated on PDA agar plates (39 g/L BD-Difco Potato dextrose agar). Spores (conidia) were collected from the PDA plates, and used as inoculum in liquid cultivations for the LBG production experiment.

Four selected clones were tested in small-scale liquid cultures and analysis of the culture supernatants by SDS-PAGE were done in day 2, day 3, and day4 (FIG. 13). Four mL of the BMG medium (20 g/L glucose, 10 g/L yeast extract, 20 g/L bacto peptone, 13.4 g/L YNB, 0.4 mg/L Biotin, and 100 mM $KH_2PO_4$ pH=6.0) in 24-well cultivation plates was inoculated by the conidia collected from the PDA plates. The cultures were incubated at 28° C. at 800 rpm (Infors HT Microtron), and each indicated day centrifuged to partially pellet the mycelium. Fifty μL of each culture supernatant was mixed with 25 μL of 4×SDS-loading buffer (400 mL/L Glycerol; 240 mM Tris·HCl pH=6.8; 80 g/L SDS; 0.4 g/L bromophenol blue; and 50 mL/L β-mercaptoethanol), and incubated at 95° C. for 4 minutes. Fifteen μL of the mixtures were loaded on the 4-20% SDS-PAGE gradient gel next to the molecular weight standard, and commercially avaible pure β-Lactoglobulin B from bovine milk. After complete protein separation in an electric field (PowerPac HC; BioRad), the gel was stained with colloidal coomassie stain (PageBlue Protein Staining Solution; THERMO FISHER SCIENTIFIC®) according to the manufacture's protocol. The visualization of the stained gel was performed on the ODYSSEY® CLx Imaging System instrument (LI-COR® Biosciences). The scan of the stained gel is shown in FIG. 13. There was clear consistent production of a protein (identical to pure LGB as determined by a molecular mass) into the culture supernatant in all tested strains. The high-level production of LGB in all four tested clones was achieved by expression system containing the Bn_TAF1M activation domain. Therefore, it is evident that the plant-based activation domain(s) can be successfully used for recombinant protein production in *Aspergillus oryzae*.

Example 8

Testing of Transcription Activation Domain Bn-TAF1M as a Part of Synthetic Expression System Controlled by Doxycycline in *Trichoderma reesei, Pichia Pastoris*, and *Yarrowia lipolytica*

The reporter expression system for testing doxycycline-dependent expression in *Trichoderma reesei* was constructed as a single DNA molecule (plasmid) (FIG. 1, Table 2A). The plasmid contained same parts as described in Example 1, except for the DNA-binding domain of the sTF and the sTF-dependent binding sites (Table 2A). The reporter expression system for testing doxycycline-dependent expression in *Pichia pastoris* (Table 2B), and *Yarrowia lipolytica* (Table 2C) were constructed as single DNA molecules (plasmids) (FIG. 14).

In all three expression cassettes, the DNA-binding-domain (DBD) was TetR (transcriptional regulator from *Escherichia coli*, GenBank: EFK45326.1) extended by SV40 NLS. The DBD encoding DNA was codon optimized for *Saccharomyces cerevisiae* in case of the construct used in *Pichia pastoris* (Table 2B), or for *Aspergillus niger* in case of the constructs used in *Trichoderma reesei* (Table 2A) and *Yarrowia lipolytica* (Table 2C).

The transcription activation domain (AD) was Bn-TAF1M (SEQ ID NO: 11) in all expression cassettes; The AD encoding DNA was codon optimized for *Aspergillus niger* in case of the constructs used in *Trichoderma reesei* and *Yarrowia lipolytica* (Table 2A and 2B), or for *Pichia pastoris* for in case of the construct used in *Pichia pastoris* (Table 2C).

The expression cassettes contained target gene cassette, which consisted of eight TetR-binding sites (BS; sequences shown in Table 2A, 2B, and 2C); *Aspergillus niger* 201 core promoter (An_201cp; sequence shown in Table 2A and 2B), or *Yarrowia lipolytica* 565 core promoter (Yl_565cp; sequence shown in Table 2C); mCherry encoding DNA (target gene; sequence shown in Table 2A, 2B and 2C); and *Trichoderma reesei* pdc1 terminator (Tr_PDC1t; Table 2A), or *Saccharomyces cerevisiae* ADH1 terminator (Sc_ADH1t; Table 2B and 2C). The plasmids further contained synthetic transcription factor (sTF) expression cassette, which consisted of *Trichoderma reesei* hfb2 core promoter (Tr_hfb2cp; sequence shown in Table 2A), or *Aspergillus niger* 008 core promoter (An_008cp; Table 2B), or *Yarrowia lipolytica* 242 core promoter (Yl_242cp; Table 2C); the sTF coding region; and *Trichoderma reesei* tef1 terminator (Tr_TEF1 t; Table 2A, 2B and 2C).

The expression cassette for *Pichia pastoris* also contained a selection marker allowing expression of the kanR gene, and genome integration DNA flanks for targeting the ADE1 gene. The expression cassette for *Yarrowia lipolytica* also contained a selection marker allowing expression of the NAT gene, and genome integration DNA flanks for targeting the anti gene.

*Trichoderma reesei* strain M1909 (VTT culture collection), *Pichia pastoris* Y-11430 strain, and *Yarrowia lipolytica* strain C-00365 (VTT culture collection) were used as the parental strains. The expression system (FIG. 1, Table 2A) was transformed into *T. reesei* by the PEG transformation protocol (described in Example 5); the expression systems (FIG. 14, Table 2B and 2C) were transformed into *P. pastoris* or *Y. lipolytica*, respectively, by a lithium-acetate protocol (described in Example 4). The transformed cells of *T. reesei* were selected for growth on media lacking uracil, the transformed cells of *P. pastoris* were selected on media containing 500 mg/L of G418, and the transformed cells of *Y. lipolytica* were selected on media containing 150 mg/L Nourseothricin.

Three randomly selected colonies from each transformation were analyzed for mCherry fluorescence in liquid cultures, in absence of doxycycline (DOX), and in presence of 1 mg/L or 3 mg/L doxycycline (DOX) (FIG. 15).

For the quantitative fluorometry analysis of the mCherry production in the mycelia of the *T. reesei* strains or in the cells of *P. pastoris* and *Y. lipolytica* strains (FIG. 15), four mL of the BMG medium (20 g/L glucose, 10 g/L yeast extract, 20 g/L bacto peptone, 13.4 g/L YNB, 0.4 mg/L Biotin, and 100 mM $KH_2PO_4$ pH=6.0) containing no doxycycline, or containing 1 mg/L or 3 mg/L doxycycline in 24-well cultivation plates was inoculated to OD600=0.1 by the spores/cells of the selected clones. The cultures were grown for 24 hours at 800 rpm (Infors HT Microtron) and 28° C., centrifuged, pellets washed with water, and resuspended in 0.5 mL of sterile water. Two hundred μL of each mycelium/cell suspension was analyzed in black 96-well plates (Black Cliniplate; THERMO SCIENTIFIC®) using the VARIOSKAN® (Thermo Electron Corporation) fluorometer. The settings for mCherry were 587 nm (excitation) and 610 nm (emission), respectively. For normalization of the fluorescence results, the analyzed mycelium/cell-suspensions were diluted 100× and OD600 was measured in transparent 96-well microtiter plates (NUNC) using VARIOSKAN® (Thermo Electron Corporation). The results from the analysis are shown in FIG. 15. These results clearly indicate that the selected plant-based activation domain can be successfully used in a doxycycline-dependent expression system (TET-OFF) for controlled expression of heterologous genes in diverse fungal species.

Example 9

Developing a Synthetic Expression System Based on Plant-Derived Activation Domain for High-Level Gene Expression in *Yarrowia lipolytica* and *Cutaneotrichosporon oleaginosus*

Microbial lipid production is becoming increasingly attractive topic in biotechnology, including food applications. Several promising production hosts have been identified and some of them are being established in diverse lipid compounds production bioprocesses. Further development of the production hosts is, however, often hindered by limited amount of robust gene expression tools available for genetic manipulation, such as heterologous gene expression. Synthetic expression system based on the sTF containing plant-derived activation domain was tested and optimized for two yeast species known for high-level lipid production, *Yarrowia lipolytica* and *Cutaneotrichosporon oleaginosus.*

One of the best performing plant-based activation domain identified and extensively tested in previous examples, Bn_TAF M, was chosen as an activation domain for development of expression systems for *Yarrowia lipolytica* and *Cutaneotrichosporon oleaginosus*. The expression systems were constructed as a single DNA molecule (FIG. 14), where the DBD was Bm3R1 and the target gene was a reporter mCherry. The terminators used in the cassettes were *S. cerevisiae* ADH1 terminator (term1 in FIG. 14) and *T. reesei* tef1 terminator (term2 in FIG. 14). The constructs also contained a selection marker (SM in FIG. 14) allowing expression of the NAT gene, and genome integration DNA flanks for targeting the anti gene of *Y. lipolytica* (5' and 3' in FIG. 14). A control expression system containing virus-based VP16 activation domain instead of the Bn_TAF1M-AD shown in FIG. 14 was also constructed and tested.

In case of *Yarrowia lipolytica*, the expression system (FIG. 14, FIG. 16) contained different combinations of core promoters (cp), one upstream of the target gene (cp1 in the target gene cassette in FIG. 14) and the other upstream of sTF (cp2 in the sTF cassette in FIG. 14). The following cp1—core promoters were tested: An_201cp (SEQ ID NO: 23), YI_205cp (SEQ ID NO: 34), YI_565cp (SEQ ID NO: 32), YI_137cp (SEQ ID NO: 36), YI_113cp (SEQ ID NO: 37), and YI_697cp (SEQ ID NO: 38). The following cp2—core promoters were tested: An_008cp (SEQ ID NO: 22), YI_TEF1cp (SEQ ID NO: 35), YI_242cp (SEQ ID NO: 33), and Cc_MFScp (SEQ ID NO: 40). The Bm3R1 (DBD in FIG. 14) was codon optimized for *Aspergillus niger.*

In case of *Cutaneotrichosporon oleaginosus*, the expression system (FIG. 14, FIG. 16) contained different combinations of core promoters (cp), one upstream of the target gene (cp1 in the target gene cassette in FIG. 14) and the other upstream of sTF (cp2 in the sTF cassette in FIG. 14). The following cp1—core promoters were tested: An_201cp (SEQ ID NO: 23), Cc_RAScp (SEQ ID NO: 39), Cc_GSTcp (SEQ ID NO: 42), Cc_AKRcp (SEQ ID NO: 43), and Cc_FbPcp (SEQ ID NO: 44). The following cp2—core promoters were tested: An_008cp (SEQ ID NO: 22), Cc_HSP9cp (SEQ ID NO: 41), and Cc_MFScp (SEQ ID NO: 40). The Bm3R1 (DBD in FIG. 14) was codon optimized for *Cutaneotrichosporon oleaginosus*. The DNA sequence of an example expression system containing Cc_FbPcp and Cc_MFScp is shown in Table 2D.

*Yarrowia lipolytica* strain C-00365 (VTT culture collection) and *Cutaneotrichosporon oleaginosus* (previously known as *Trichosporon oleaginosus, Cryptococcus curvatus*, Apiotrichum curvatum or *Candida curvata*) strain ATCC 20509 were used as the parental strains. The expression systems were transformed into *Y. lipolytica* by a lithium-acetate protocol (described in Example 4). The expression systems were transformed into *C. oleaginosus* by electroporation (following protocol is for 1 transformation): 20 mL of liquid culture grown in YPD to reach OD-1.0 was centrifuged shortly (4000 rpm/1 min) to pellet the cells. The cells were washed with 10 mL of ice cold sterile EB-solution (10 mM Tris pH=7.5; 270 mM sucrose; 1 mM $MgCl_2$) and resuspended in 5 mL of IB-solution (25 mM DTT; 20 mM HEPES pH=8.0; in YPD). The cell suspension was incubated at 30° C. shaking at 22 rpm for 30 min, then centrifuge shortly (4000 rpm/1 min) to pellet the cells. The cells were washed with washed with 20 mL of EB-solution, and the cell pellet after centrifugation (4000 rpm/1 min) was resuspended in 500 μL of EB-solution to prepare transformation competent cells. 400 μL of this cells suspension was mixed with 5-10 ug of DNA (expression system DNA cassette) in electroporation cuvette (4 mm gap) and incubated on ice for 15 min. Two consecutive electroporations were performed (BioRad GenePulser; 1800V; 1000 Ω; 25 uF). The transformation mix was diluted with 1 mL of YPD and incubated at 30° C. shaking 220 rpm for 4 h prior to spreading the cells on selective agar plates.

The transformed cells of *Y. lipolytica* and *C. oleaginosus* were selected for growth on media (YPD agar) containing 150 mg/L Nourseothricin. Three colonies from each transformation were analyzed for mCherry fluorescence in liquid cultures.

For the quantitative fluorometry analysis of the mCherry production in the the cells of *P. pastoris* (FIG. 16), four mL of the YPD medium in 24-well cultivation plates was inoculated to OD600=0.1 by the cells of the selected clones. The cultures were grown for 24 hours at 800 rpm (Infors HT Microtron) and 28° C., centrifuged, pellets washed with water, and resuspended in 0.5 mL of sterile water. Two hundred μL of each cell suspension was analyzed in black 96-well plates (Black Cliniplate; THERMO SCIENTIFIC®) using the VARIOSKAN® (Thermo Electron Corporation) fluorometer. The settings for mCherry were 587 nm (excitation) and 610 nm (emission), respectively. For normalization of the fluorescence results, the analyzed cell-suspensions were diluted 100× and OD600 was measured in transparent 96-well microtiter plates (NUNC) using VARIOSKAN® (Thermo Electron Corporation). The results from the analysis are shown in FIG. 16. These results clearly indicate that the selected plant-based (such as edible plant-based) activation domain can be successfully used instead of the viral-based VP16 AD for high-level expression of a heterologous gene in *Y. lipolytica* and *C. oleaginosus*. The control system with the VP16-AD was also tested in *C. oleaginosus*, but no fluorescence was detected in the transformed cells (data not shown), the lack of mCherry expression was however likely due to non-functional core promoters An_201cp and An_008 rather than non-functional VP16-AD in *C. oleaginosus*.

TABLE 2

DNA sequences of example doxycycline-repressible reporter expression cassettes for testing the engineered plant-based transcription activation domains in Trichoderma reesei (A), Pichia pastoris (B), Yarrowia lipolytica (C), and an example expression system used in Cutaneotrichosporon oleaginosus (D). The functional DNA parts are indicated: 8xsTF-specific binding site (black bolded text); core promoters (underlined text); mCherry coding region (black bolded underlined text); terminators (italics); and sTF (bolded italics) including the plant-based activation domain (bolded underlined italics).

Example DNA sequences of the tested expression systems with the TetR-based sTF allowing doxycycline-repressible expression of a reporter gene.

| | |
|---|---|
| A | TTTGCTCGGCTAGCTCTCTATCACTGATAGGGAGTATTGACAAGCTTTCTCTATCACTGATAGGAGTGGCTT |
| 8BS(TetR)- | ATCTAGATCTCTATCACTGATAGGGAGTTCACATCCTAGGTCTCTATCACTGATAGGGAGTACTAGCTCTCT |
| An_201cp- | ATCACTGATAGGGAGTATTGACAAGCTTTCTCTATCACTGATAGGAGTGGCTTATCTAGATCTCTATCACTG |
| mCherry- | ATAGGGAGTTCACATCCTAGGTCTCTATCACTGATAGGGAGTACTAGTTCTCCCCGGAAACTGTGGCCATA |
| Tr_PDC1t + | TGTTCAAAGACTAGGATGGATAAATGGGGTATATAAAGCACCCTGACTCCCTTCCTCCAAGTTCTATCTAAC |
| Tr_hfb2cp- | CAGCCATCCTACACTCTACATATCCACACCAATCTACTACAATTAATTAAAATGGTGAGCAAGGGCGAGGA |
| BM3R1_BnT | GGATAACATGGCCATCATCAAGGAGTTCATGCGCTTCAAGGTGCACATGGAGGGCTCCGTGAACGGCCA |
| AF1M- | CGAGTTCGAGATCGAGGGCGAGGGCGAGGGCCGCCCCTACGAGGGCACCCAGACCGCCAAGCTGAAG |
| Tr_TEF1t | GTGACCAAGGGTGGCCCCCTGCCCTTCGCCTGGGACATCCTGTCCCCTCAGTTCATGTACGGCTCCAAG |
| | GCCTACGTGAAGCACCCCGCCGACATCCCCGACTACTTGAAGCTGTCCTTCCCCGAGGGCTTCAAGTGG |
| | GAGCGCGTGATGAACTTCGAGGACGGCGGCGTGGTGACCGTGACCCAGGACTCCTCCCTGCAGGACGG |
| | CGAGTTCATCTACAAGGTGAAGCTGCGCGGCACCAACTTCCCCTCCGACGGCCCCGTAATGCAGAAGAA |
| | GACCATGGGCTGGGAGGCCTCCTCCGAGCGGATGTACCCCGAGGACGGCGCCCTGAAGGGCGAGATCA |
| | AGCAGAGGCTGAAGCTGAAGGACGGCGGCCACTACGACGCTGAGGTCAAGACCACCTACAAGGCCAAG |
| | AAGCCCGTGCAGCTGCCCGGCGCCTACAACGTCAACATCAAGTTGGACATCACCTCCCACAACGAGGAC |
| | TACACCATCGTGGAACAGTACGAACGCGCCGAGGGCCGCCACTCCACCGGCGGCATGGACGAGTTATA |
| | CAAGTAATGAGGATCTCCCGGCATGAAGTCTGACCGGGTAGTATGAGGGTTCATCGTCACCTTGATAGAAT |
| | AATAGACGATAAAGCAGGCCACGGGCAGGTACCGATTGTCAATCCGGCAGGTTAGGAGGCGTGTTGGAAA |
| | TGAGTTTATGGGTTATGGTCAAATCGGATAGTATGAGGTACATAGTTTGTAAATCTCAAGATTATTTTCTTCC |
| | TTAATCTTGCACGTCGCATGAGAGGGACCGAGAAGAGAATTGATGAAGGGCTCTTGAAGATGAGATGAATC |
| | ACGTGGTTGCTGAAGCTTCAGTAGTCTCGGGTACCTGTTCTTTCCCACAAACAGTAGCCAGGCTAGAGGTA |
| | CTGAGTACCCGCTCACCGTATCTAATCATCCGACCTGAAATCTTCAAGCTGTTTTATTGACACTTCGAGTCC |
| | ATCTTCATTCACGTAAGGAGAACTTCTAGGACATCACTTATCCCGCCATATTTAGCTGCAAGGAGTCAATTG |
| | CAATGTCAGATTCCGCTCCTAAGAGGAAACAGGGCCCTGGCGGCTCAGATGGCTCGGCATTGAAGAAGAG |
| | AAAGGTATGATGACAAGAATGCTTGCTACAAATTACCCAGTAGCCGGGCACTAACAGCTCCCTGGCCTAGG |
| | TAGACTACCTACCTCAAGGTACGACACATGGCAGCACTGGAGGGGGAATAGGCAGACTGGACGACAGTGG |
| | ACAAGATACGGTCGCACAACCTTTGTCGTGGCATCGCGAGAATAATCGTCACAAGCTTCACGTATGCAGAC |
| | GGAGACAAGATGATTTGGTTGTCGAAGTCATGAATTCACTTCTATCTAGTTTTTTGTTCCCTTTTGTTTTGCA |
| | TTCCCAGAGAAGTTCTGATGGAACCCTTATTCCCAGCCTCTCAATTAACGTGCCTCGATTCATAGTCGAGTG |
| | CTCATGCATAGCAACATTGATCGTTTCGTCGTAGAAGTGAGCGCATGGTGGTGCCCACCTGGAGAAACCTC |
| | ACGAGGGACCCCAGAACATCAGGTGTTGATGATGGGTATCGCGGCCGGCCCTAGTAAGGCTTGGGCATGT |
| | TGTACATGAACATGTCCTGCAGGGGAAACAGCTGGTTGCTGCCGCCGCCGCCAAAGGCGGTGGCGTCGA |
| | TGTAGTTGAAGCCGAAGTCGAGGGAGTTGTCGTCGTTGGCAGCGCCGGACCAGTCGTCCCAGAGGGGCT |
| | CGCTCTGGACCTCGCTGGTGAACTCGGGGCTGACGACCTGCTCGCTGCAGCTGCTCTCGGTGGTGTGGA |
| | GGTCGGGGACGCTGTCGCTGGTGTCGAAGTAGACGAAGTCGTTGGGCATGACAGGCGGAGGAGGCATG |
| | CCCATCTCGCTGCCGGAGCCGACCTTGCGCTTCTTCTTAGGAGGGCTAGCGGACCCAGACTCACACTTG |
| | AGTTGCTTCTCGAGCCCACAAATGATCAATTCCAAGCCGAATAGAAACGCAGGCTCGGCGCCTTGGTGAT |
| | CGAACAACTCTATCGCCTGTCTCAGCAGGGGTGGCATGGAATCTGTGGTGGGAGTCTCTCTTTCTTCTTTA |
| | GCGACTTGATGTTCTTGGTCTTCCAGAACACAACCTAGGGTGAAGTGTCCGACTGCAGACAAGGCGTAAA |
| | GTGCATTTTCCAAGGAGAAACCCTGCTGGCAGAGAAATGCGAGTTGATTCTCAAGCGTCTCATACTGCTT |
| | CTCGGTTGGTCGGGTCCCGAGATGAACTTTAGCACCGTCCCGATGACTCAGCAAGGCACAACGGAAAGA |
| | CTTGGCGTTGTTGCGAAGAAAGTCTTGCCACGACTCTCCTTCCAGTGGACAAAAATGGGTATGATGTCTA |
| | TCCAACATCTCGATTGCAAGTGCATCCAGCAGTGCTCTCTTATTTTTGACGTGCCAGTAAAGGGTTGGCTG |
| | CTCGACGCCGAGCTTTTGCGCAAGTTTTCGCGTCGTCAAACCCTCAATTCCAACCTCATTAAGGAGTTCC |
| | AACGCGGAATTAATGACCTTCGACTTATCCAGACGTGACATTGTATTTAAATGTGATGGTTGGTATTCAACA |
| | AAGAATGTTTGTGTTTGGAGAGTTGAGAAAGAGGAGTTGAGTGAATGTGGTGATGGTTGTAGATGAGTGTG |
| | CTGATGAGGATGGAAAAGATTGTTGGATGGCGGGAATCGAGGTCTTCTTTATACTTTTTTTTCTGGCCCTCT |
| | TCATCTTCCAGCTCTCGCAGGCTGTTGCTAGAAATCTCGACGCGCAATTAACCCTCACGGGCGCGGCCGC |
| B | TTTGCTCGGCTAGCTCTCTATCACTGATAGGGAGTATTGACAAGCTTTCTCTATCACTGATAGGAGTGGCTT |
| 8BS(TetR)- | ATCTAGATCTCTATCACTGATAGGGAGTTCACATCCTAGGTCTCTATCACTGATAGGGAGTACTAGCTCTCT |
| An_201cp- | ATCACTGATAGGGAGTATTGACAAGCTTTCTCTATCACTGATAGGAGTGGCTTATCTAGATCTCTATCACTG |
| mCherry- | ATAGGGAGTTCACATCCTAGGTCTCTATCACTGATAGGGAGTACTAGTTCTCCCCGGAAACTGTGGCCATA |
| Sc_ADH1t + | TGTTCAAAGACTAGGATGGATAAATGGGGTATATAAAGCACCCTGACTCCCTTCCTCCAAGTTCTATCTAAC |
| An_008cp - | CAGCCATCCTACACTCTACATATCCACACCAATCTACTACAATTATTAATTAAAATGGTGAGCAAGGGCGAG |
| TetR (Sc- | GAGGATAACATGGCCATCATCAAGGAGTTCATGCGCTTCAAGGTGCACATGGAGGGCTCCGTGAACGGC |
| opt)_Bn- | CACGAGTTCGAGATCGAGGGCGAGGGCGAGGGCCGCCCCTACGAGGGCACCCAGACCGCCAAGCTGA |
| TAF1M (Pp- | AGGTGACCAAGGGTGGCCCCCTGCCCTTCGCCTGGGACATCCTGTCCCCTCAGTTCATGTACGGCTCCA |
| opt) | AGGCCTACGTGAAGCACCCCGCCGACATCCCCGACTACTTGAAGCTGTCCTTCCCCGAGGGCTTCAAGT |
| Tr_TEF1t | GGGAGCGCGTGATGAACTTCGAGGACGGCGGCGTGGTGACCGTGACCCAGGACTCCTCCCTGCAGGAC |
| | GGCGAGTTCATCTACAAGGTGAAGCTGCGCGGCACCAACTTCCCCTCCGACGGCCCCGTAATGCAGAAG |
| | AAGACCATGGGCTGGGAGGCCTCCTCCGAGCGGATGTACCCCGAGGACGGCGCCCTGAAGGGCGAGAT |
| | CAAGCAGAGGCTGAAGCTGAAGGACGGCGGCCACTACGACGCTGAGGTCAAGACCACCTACAAGGCCA |
| | AGAAGCCCGTGCAGCTGCCCGGCGCCTACAACGTCAACATCAAGTTGGACATCACCTCCCACAACGAGG |
| | ACTACACCATCGTGGAACAGTACGAACGCGCCGAGGGCCGCCACTCCACCGGCGGCATGGACGAGTTA |
| | TACAAGTAATGAGGATCCGAATTTCTTATGATTTATGATTTTTATTATTAAATAAGTTATAAAAAAAATAAGTGT |
| | ATACAAATTTTAAAGTGACTCTTAGGTTTTAAAACGAAAATTCTTATTCTTGAGTAACTCTTTCCTGTAGGTCA |
| | GGTTGCTTTCTCAGGTATAGCATGAGGTCGCTCTTATTGACCACACCTCTACCGGCCAGCTTTTGTTCCCTT |
| | TAGTGAGGGTTAATTGCGCGTCGAGGCTAGCAACCCAAAGTAATAAGTCTGTAGTAATTGGTCTCGCCCTG |

TABLE 2-continued

DNA sequences of example doxycycline-repressible reporter expression cassettes for testing the engineered plant-based transcription activation domains in Trichoderma reesei (A), Pichia pastoris (B), Yarrowia lipolytica (C), and an example expression system used in Cutaneotrichosporon oleaginosus (D). The functional DNA parts are indicated: 8xsTF-specific binding site (black bolded text); core promoters (underlined text); mCherry coding region (black bolded underlined text); terminators (italics); and sTF (bolded italics) including the plant-based activation domain (bolded underlined italics).
Example DNA sequences of the tested expression systems with the TetR-based sTF allowing doxycycline-repressible expression of a reporter gene.

| | |
|---|---|
| | AATTCCAAACTATAAATCAACCACTTTCCCTCCTCCCCCCCGCCCCCACTTGGTCGATTCTTCGTTTTCTCTC<br>TACCTTCTTTCTATTCGGTTTTCTTCTTCTTTTATTTTCCCTCTCCCATCAATCAAATTCATATTTGAAAAAAT<br>TAACATTAATTTAAATACAATGAGTAGATTAGACAAATCAAAAGTGATAAATTCTGCATTAGAATTGTTGAA<br>TGAAGTAGGCATTGAAGGTTTGACTACCCGTAAGTTAGCTCAGAAACTAGGTGTTGAACAACCTACATTA<br>TACTGGCACGTTAAAAATAAAAGGGCATTGTTGGATGCGCTTGCCATTGAGATGTTGGATAGGCATCATA<br>CCCACTTTTGCCCATTAGAAGGAGAGTCTTGGCAGGACTTTTTGAGGAATAATGCCAAGTCATTTAGATGT<br>GCATTGTTGTCTCATAGAGATGGGGCCAAGGTTCATCTAGGTACCCGTCCTACGGAAAAACAATATGAGA<br>CGTTGGAAAATCAGTTAGCGTTCTTATGCCAACAAGGCTTTAGCTTGGAAAATGCTTTATATGCTCTATCA<br>GCTGTCGGTCATTTTACATTGGGATGCGTTTTAGAAGACCAGGAGCACCAGGTGGCAAAGGAAGAAAGA<br>GAAACACCAACAACTGATTCAATGCCACCCCTACTGAGACAAGCTATCGAATTATTTGATCATCAAGGTG<br>CGGAACCTGCCTTCTTGTTTGGCCTAGAATTGATCATTTGTGGTTTAGAAAAGCAGTTAAAATGTGAGAGT<br>GGCTCAGAATTCCCACCCAAGAAGAAGCGTAAAGTGGGCAGTGGCTCTGAGATGGGTATGCCTCCTCCA<br>CCTGTTATGCCTAACGACTTCGTGTATTTTGATACGTCAGATTCTGTTCCCGACTTGCATACTACGGAATC<br>CTCTTGTTCAGAGCAGGTTGTATCACCAGAATTTACATCTGAAGTCCAATCAGAACCACTGTGGGACGAT<br>TGGTCAGGTGCCGCAAACGATGACAATTCACTTGATTTTGGTTTTAATTACATCGATGCAACCGCATTTGG<br>TGGCGGAGGCAGTAATCAGCTGTTTCCATTGCAGGATATGTTCATGTACAACATGCCTAAGCCTTATTGA<br>GGCCGGCCGCGATACCCATCATCAACACCTGATGTTCTGGGGTCCCTCGTGAGGTTTCTCCAGGTGGGCA<br>CCACCATGCGCTCACTTCTACGACGAAACGATCAATGTTGCTATGCATGAGCACTCGACTATGAATCGAGG<br>CACGTTAATTGAGAGGCTGGGAATAAGGGTTCCATCAGAACTTCTCTGGGAATGCAAAACAAAAGGGAACA<br>AAAAAACTAGATAGAAGTGAATTCATGACTTCGACAACCAAATCATCTTGTCTCCGTCTGCATACGTGAAGCT<br>TGTGACGATTATTCTCGCGATGCCACGACAAAGGTTGTGCGACCGTATCTTGTCCACTGTCGTCCAGTCTG<br>CCTATTCCCCCTCCAGTGCTGCCATGTGTCGTACCTTGAGGTAGGTAGTCTA |
| C<br>8BS(TetR)-<br>YI_565cp-<br>mCherry-<br>Sc_ADH1t +<br>YI_242cp-<br>TetR_Bn-<br>TAF1M-<br>Tr_TEF1t | TTTGCTCGGCTAGCTCTCTATCACTGATAGGGAGTATTGACAAGCTTTCTCTATCACTGATAGGAGTGGCTT<br>ATCTAGATCTCTATCACTGATAGGGAGTTCACATCCTAGGTCTCTATCACTGATAGGGAGTACTAGCTCTCT<br>ATCACTGATAGGGAGTATTGACAAGCTTTCTCTATCACTGATAGGAGTGGCTTATCTAGATCTCTATCACTG<br>ATAGGGAGTTCACATCCTAGGTCTCTATCACTGATAGGGAGTACTAGTTCTCCCCGGAAACTGTGGCCATA<br>TGCCTCTGCTTGCAATGAAGCTGTGGGTGGAGTAAACGGTGCCGCTTAATACAGGGATGGTGCGTGAGATA<br>GGAGATTTGGAGCCGTCTACTCTGTCGGCCAACGACATAAATAGACCCCCTCAGTCACCTTAGACACAGCA<br>GAATTCCACCAGATCAGCTTCCTTAATTAATCATGGTGAGCAAGGGCGAGGAGGATAACATGGCCATCAT<br>CAAGGAGTTCATGCGCTTCAAGGTGCACATGGAGGGCTCCGTGAACGGCCACGAGTTCGAGATCGAGG<br>GCGAGGGCGAGGGCCGCCCCTACGAGGGCACCCAGACCGCCAAGCTGAAGGTGACCAAGGGTGGCCC<br>CCTGCCCTTCGCCTGGGACATCCTGTCCCCTCAGTTCATGTACGGCTCCAAGGCCTACGTGAAGCACCCC<br>GCCGACATCCCCGACTACTTGAAGCTGTCCTTCCCCGAGGGCTTCAAGTGGGAGCGCGTGATGAACTTC<br>GAGGACGGCGGCGTGGTGACCGTGACCCAGGACTCCTCCCTGCAGGACGGCGAGTTCATCTACAAGGT<br>GAAGCTGCGCGGCACCAACTTCCCCTCCGACGGCCCCGTAATGCAGAAGAAGACCATGGGCTGGGAGG<br>CCTCCTCCGAGCGGATGTACCCCGAGGACGGCGCCCTGAAGGGCGAGATCAAGCAGAGGCTGAAGCTG<br>AAGGACGGCGGCCACTACGACGCTGAGGTCAAGACCACCTACAAGGCCAAGAAGCCCGTGCAGCTGCC<br>CGGCGCCTACAACGTCAACATCAAGTTGGACATCACCTCCCACAACGAGGACTACACCATCGTGGAACA<br>GTACGAACGCGCCGAGGGCCGCCACTCCACCGGCGGCATGGACGAGTTATACAAGTAATGATCAGAATT<br>TCTTATGATTTATGATTTTTATTATTAAATAAGTTATAAAAAAAATAAGTGTATACAAATTTTAAAGTGACTCTTA<br>GGTTTTAAAACGAAAATTCTTATTCTTGAGTAACTCTTTCCTGTAGGTCAGGTTGCTTTCTCAGGTATAGCAT<br>GAGGTCGCTCTTATTGACCACACCTCTACCGGCCAGCTTTTGTTCCCTTTAGTGAGGGTTAATTGCGCGTCG<br>AGGCTACTAGTCATTAGCTTGTTGACAAAACCTTATGCGTCGCAGAGCATATACGCTCGGAAGCCTACCCC<br>GTCACCTCCGTGACATGATGTAACTCCTTTACTATATATAGACGTGTGTTCGTATCGAAAATAGCCAGACACT<br>CTTTGCTCCATCACTCACATTTAAATACAATGTCACGTCTGGATAAGTCGAAGGTCATTAATTCCGCGTTGG<br>AACTCCTTAATGAGGTTGGAATTGAGGGTTTGACGACGCGAAAACTTGCGCAAAAGCTCGGCGTCGAGC<br>AGCCAACCCTTTACTGGCACGTCAAAAATAAGAGAGCACTGCTGGATGCACTTGCAATCGAGATGTTGGA<br>TAGACATCATACCCATTTTTGTCCACTGGAAGGAGAGTCGTGGCAAGACTTTCTTCGCAACAACGCCAAG<br>TCTTTCCGTTGTGCCTTGCTGAGTCATCGGGACGGTGCTAAAGTTCATCTCGGGACCCGACCAACCGAGA<br>AGCAGTATGAGACGCTTGAGAATCAACTCGCATTTCTCTGCCAGCAGGGTTTCTCCTTGGAAAATGCACT<br>TTACGCCTTGTCTGCAGTCGGACACTTCACCCTAGGTTGTGTTCTGGAAGACCAAGAACATCAAGTCGCT<br>AAAGAAGAAAGAGAGACTCCCACCACAGATTCCATGCCACCCCTGCTGAGACAGGCGATAGAGTTGTTC<br>GATCACCAAGGCGCCGAGCCTGCGTTTCTATTCGGCTTGGAATTGATCATTTGTGGGCTCGAGAAGCAAC<br>TCAAGTGTGAGTCTGGGTCCGCTAGCCCTCCTAAGAAGAAGCGCAAGGTCGGCTCCGGCAGCGAGATGG<br>GCATGCCTCCTCCGCCTGTCATGCCCAACGACTTCGTCTACTTCGACACCAGCGACAGCGTCCCCGACCT<br>CCACACCACCGAGAGCAGCTGCAGCGAGCAGGTCGTCAGCCCCGAGTTCACCAGCGAGGTCCAGAGCG<br>AGCCCCTCTGGGACGACTGGTCCGGCGCTGCCAACGACGACAACTCCCTCGACTTCGGCTTCAACTACA<br>TCGACGCCACCGCCTTTGGCGGCGGCGGCAGCAACCAGCTGTTTCCCCTGCAGGACATGTTCATGTACA<br>ACATGCCCAAGCCTTACTAGGGCCGGCCGCGATACCCATCATCAACACCTGATGTTCTGGGGTCCCTCGT<br>GAGGTTTCTCCAGGTGGGCACCACCATGCGCTCACTTCTACGACGAAACGATCAATGTTGCTATGCATGAG<br>CACTCGACTATGAATCGAGGCACGTTAATTGAGAGGCTGGGAATAAGGGTTCCATCAGAACTTCTCTGGGA<br>ATGCAAAACAAAAGGGAACAAAAAAACTAGATAGAAGTGAATTCATGACTTCGACAACCAAATCATCTTGTCT<br>CCGTCTGCATACGTGAAGCTTGTGACGATTATTCTCGCGATGCCACGACAAAGGTTGTGCGACCGTATCTT<br>GTCCACTGTCGTCCAGTCTGCCTATTCCCCCTCCAGTGCTGCCATGTGTCGTACCTTGAGGTAGGTAGTCT |

TABLE 2-continued

DNA sequences of example doxycycline-repressible reporter expression cassettes for testing the engineered plant-based transcription activation domains in Trichoderma reesei (A), Pichia pastoris (B), Yarrowia lipolytica (C), and an example expression system used in Cutaneotrichosporon oleaginosus (D). The functional DNA parts are indicated: 8xsTF-specific binding site (black bolded text); core promoters (underlined text); mCherry coding region (black bolded underlined text); terminators (italics); and sTF (bolded italics) including the plant-based activation domain (bolded underlined italics).
Example DNA sequences of the tested expression systems with the TetR-based sTF allowing doxycycline-repressible expression of a reporter gene.

| | |
|---|---|
| | ACCTAGGCCAGGGAGCTGTTAGTGCCCGGCTACTGGGTAATTTGTAGCGCTGGAGCGATTCGGTCACAGG |
| | CGTCAAGAGTGCTGTAGCAATGTCCGACGCCATTGATCCTGATATCAAATACCACCTGGGCAGGTCTGGGT |
| | ATGTGAGGTCTTGTCGGATGTGTCGAGTTCTTCTCCAACGTAGTGTTCATTCGCGCTCAT |
| D | TTTGCAGGCATTTGCTCGGCTAGTCGGAATGAACATTCATTCCGAGACCTAGGATGTGACGGAATGAAGG |
| 8BS(Bm3r1)- | TTCATTCCGGACTCTAGATAAGCACGGAATGAACTTTCATTCCGCTGAAGCTTGTCAATCGGAATGAAGGT |
| Co_FbPcp- | TCATTCCGGCTAGTCGGAATGAACATTCATTCCGAGACCTAGGATGTGACGGAATGAAGGTTCATTCCGG |
| mCherry- | ACTCTAGATAAGCACGGAATGAACTTTCATTCCGCTGAAGCTTGTCAATCGGAATGAAGGTTCATTCCGGC |
| Sc_ADH1t + | TAGTTCTCCCCGGAAACTGTGGCCATATGCCTCAGCCAGTCTCCCACGCTCTCACCCTACCCCCACGCACC |
| Cc_MFScp - | TCCCGTTATAAGAAGCCGACGACGTGGCTAAGCCCCCAAAGCCTCCACCACCTTCCATCCGTCTCTCTCTT |
| Bm3R1_Bn- | CTCCTACTACCACAACTTAATTAATCATGGTGAGCAAGGGCGAGGAGGATAACATGGCCATCATCAAGGA |
| TAF1M- | GTTCATGCGCTTCAAGGTGCACATGGAGGGCTCCGTGAACGGCCACGAGTTCGAGATCGAGGGCGAGG |
| Tr_TEF1t | GCGAGGGCCGCCCCTACGAGGGCACCCAGACCGCCAAGCTGAAGGTGACCAAGGGTGGCCCCCTGCCC |
| | TTCGCCTGGGACATCCTGTCCCCTCAGTTCATGTACGGCTCCAAGGCCTACGTGAAGCACCCCGCCGAC |
| | ATCCCCGACTACTTGAAGCTGTCCTTCCCCGAGGGCTTCAAGTGGGAGCGCGTGATGAACTTCGAGGAC |
| | GGCGGCGTGGTGACCGTGACCCAGGACTCCTCCCTGCAGGACGGCGAGTTCATCTACAAGGTGAAGCTG |
| | CGCGGCACCAACTTCCCCTCCGACGGCCCCGTAATGCAGAAGAAGACCATGGGCTGGGAGGCCTCCTC |
| | CGAGCGGATGTACCCCGAGGACGGCGCCCTGAAGGGCGAGATCAAGCAGAGGCTGAAGCTGAAGGAC |
| | GGCGGCCACTACGACGCTGAGGTCAAGACCACCTACAAGGCCAAGAAGCCCGTGCAGCTGCCCGGCGC |
| | CTACAACGTCAACATCAAGTTGGACATCACCTCCCACAACGAGGACTACACCATCGTGGAACAGTACGA |
| | ACGCGCCGAGGGCCGCCACTCCACCGGCGGCATGGACGAGTTATACAAGTAATGATCAGAATTTCTTATG |
| | ATTTATGATTTTTATTATTAAATAAGTTATAAAAAAAATAAGTGTATACAAATTTTAAAGTGACTCTTAGGTTTT |
| | AAAACGAAAATTCTTATTCTTGAGTAACTCTTTCCTGTAGGTCAGGTTGCTTTCTCAGGTATAGCATGAGGTC |
| | GCTCTTATTGACCACACCTCTACCGGCCAGCTTTTGTTCCCTTTAGTGAGGGTTAATTGCGCGTCGAGGCTA |
| | CTAGTGGAAGCTGGCTGTTGAGGCTGTTGAGGCTGATCGGCCGAGCGAGAGAATATAAGTCACCCCAACA |
| | CTGCCACCGCCGATCACCTCCACTCCCTCCACTACCTCACCACTACCACCTCACCTCATTTCATTTAAATAC |
| | AATGGAGTCGACGCCTACCAAGCAGAAGGCGATCTTCTCCGCCTCGCTGCTCCTCTTCGCTGAGCGCGG |
| | CTTCGACGCCACCACCATGCCCATGATCGCGGAGAACGCTAAGGTCGGCGCCGGTACTATCTACCGCTA |
| | TTTCAAGAACAAGGAGTCCCTTGTGAACGAGCTCTTCCAGCAGCACGTCAACGAGTTTCTTCAGTGTATC |
| | GAGTCCGGTCTCGCCAACGAGCGCGACGGCTACCGCGACGGCTTCCACCACATTTTCGAGGGCATGGTC |
| | ACCTTTACCAAGAACCACCCCCGTGCCCTTGGTTTCATCAAGACACACTCGCAGGGCACCTTCCTCACCG |
| | AGGAGTCCCGTCTTGCGTACCAGAAGCTCGTCGAGTTTGTCTGCACGTTTTTCCGTGAGGGTCAGAAGCA |
| | GGGCGTCATCCGTAACCTCCCGGAGAACGCGCTTATTGCCATTCTCTTTGGTTCGTTCATGGAGGTCTAC |
| | GAGATGATCGAGAACGATTACCTTTCGCTCACGGACGAGCTCCTTACCGGCGTCGAGGAGTCGCTCTGG |
| | GCCGCCCTCTCGCGCCAGTCTGCTAGCCCTCCTAAGAAGAAGCGCAAGGTCGGCTCCGGCAGCGAGAT |
| | GGGCATGCCTCCTCCGCCTGTCATGCCCAACGACTTCGTCTACTTCGACACCAGCGACAGCGTCCCCGA |
| | CCTCCACACCACCGAGAGCAGCTGCAGCGAGCAGGTCGTCAGCCCCGAGTTCACCAGCGAGGTCCAGA |
| | GCGAGCCCCTCTGGGACGACTGGTCCGGCGCTGCCAACGACGACAACTCCCTCGACTTCGGCTTCAACT |
| | ACATCGACGCCACCGCCTTTGGCGGCGGCGGCAGCAACCAGCTGTTTCCCCTGCAGGACATGTTCATGT |
| | ACAACATGCCCAAGCCTTACTAGGGCCGGCCGCGATACCCATCATCAACACCTGATGTTCTGGGGTCCCT |
| | CGTGAGGTTTCTCCAGGTGGGCACCACCATGCGCTCACTTCTACGACGAAACGATCAATGTTGCTATGCAT |
| | GAGCACTCGACTATGAATCGAGGCACGTTAATTGAGAGGCTGGGAATAAGGGTTCCATCAGAACTTCTCTG |
| | GGAATGCAAAACAAAAGGGAACAAAAAAACTAGATAGAAGTGAATTCATGACTTCGACAACCAAATCATCTT |
| | GTCTCCGTCTGCATACGTGAAGCTTGTGACGATTATTCTCGCGATGCCACGACAAAGGTTGTGCGACCGTA |
| | TCTTGTCCACTGTCGTCCAGTCTGCCTATTCCCCCTCCAGTGCTGCCATGTGTCGTACCTTGAGGTAGGTA |
| | GTCTACCTAGGCCAGGGAGCTGTTAGTGCCCGGCTACTGGGTAATTTGTAGCGCTGGAGCGATTCGGTCA |
| | CAGGCGTCAAGAGTGCTGTAGCAATGTCCGACGCCATTGATCCTGATATCAAATACCACCTGGGCAGGTCT |
| | GGGTATGTGAGGTCTTGTCGGATGTGTCGAGTTCTTCTCCAACGTAGTGTTCATTCGCGCTCAT |

REFERENCES

Chavez A et al. (2015). "Highly efficient Cas9-mediated transcriptional programming." Nat Methods, 12(4), 326-328.

Lu, Y. et al. (2016). "High-level expression of improved thermo-stable alkaline xylanase variant in *Pichia Pastoris* through codon optimization, multiple gene insertion and high-density fermentation." Scientific Reports volume 6, Article number: 37869

Naseri G et al. (2017). "Plant-derived transcription factors for orthologous regulation of gene expression in the yeast *Saccharomyces cerevisiae*. ACS Synthetic Biology, 6, 1742-1756.

Olsen, A. N., H. A. Ernst, et al. (2005). "NAC transcription factors: structurally dis-tinct, functionally diverse." Trends Plant Sci 10(2): 79-87.

Tiwari, S. B., A. Belachew, et al. (2012). "The EDLL motif: a potent plant transcriptional activation domain from AP2/ERF transcription factors." The Plant Journal 70(5): 855-865.

Zhang, J. et al. (2016). "Site-directed mutagenesis and thermal stability analysis of phytase from *Escherichia coli*." Biosci. Biotech. Res. Comm. 9(3): 357-365.

The invention claimed is:

1. A polypeptide, wherein said polypeptide is a non-viral transcription activation domain for an artificial expression system in a eukaryotic host, wherein said transcription activation domain originates from a transcription factor found in a plant species, wherein said polypeptide consists of an amino acid sequence having 96%-100% sequence identity to SEQ ID NO: 10 or SEQ ID NO: 11.

2. The polypeptide of claim 1, wherein said polypeptide consists of an amino acid sequence having 96%, 97%, 98%, or 99% sequence identity, to SEQ ID NO: 10 or SEQ ID NO: 11.

3. An artificial transcription factor, wherein said artificial transcription factor comprises the polypeptide of claim 1, a DNA-binding domain and a nuclear localization signal.

4. A polynucleotide encoding the polypeptide of claim 1.

5. An expression cassette or an expression system comprising one or more expression cassettes, wherein said expression cassette or at least one of the expression cassettes of the expression system comprises the polynucleotide of claim 4.

6. A eukaryotic host comprising the polypeptide of claim 1.

7. The polypeptide of claim 1, wherein the eukaryotic host is a fungal host or an animal host, wherein the fungal host comprises a cell of *Trichoderma, Trichoderma reesei, Pichia, Pichia pastoris, Pichia kudriavzevii, Aspergillus, Aspergillus niger, Aspergillus oryzae, Myceliophthora, Myceliophthora thermophila, Saccharomyces, Saccharomyces cerevisiae, Yarrowia, Yarrowia lipolytica, Cutaneotrichosporon, Cutaneotrichosporon oleaginosus, Trichosporon oleaginosus, Cryptococcus curvatus*, or *Zygosaccharomyces*, or wherein the animal host comprises Chinese hamster ovary (CHO) cells or a cell of *Cricetulus griseus.*

8. A method for producing a desired protein product in a eukaryotic host comprising cultivating the host of claim 6 under suitable cultivation conditions.

9. A polynucleotide encoding the artificial transcription factor of claim 3.

10. A eukaryotic host comprising the artificial transcription factor of claim 3.

11. A eukaryotic host comprising the expression cassette or expression system of claim 5.

12. The artificial transcription factor of claim 3, wherein the eukaryotic host is a fungal host or an animal host, wherein the fungal host comprises a cell of *Trichoderma, Trichoderma reesei, Pichia, Pichia pastoris, Pichia kudriavzevii, Aspergillus, Aspergillus niger, Aspergillus oryzae, Myceliophthora, Myceliophthora thermophila, Saccharomyces, Saccharomyces cerevisiae, Yarrowia, Yarrowia lipolytica, Cutaneotrichosporon, Cutaneotrichosporon oleaginosus, Trichosporon oleaginosus, Cryptococcus curvatus*, or *Zygosaccharomyces*, or wherein the animal host comprises Chinese hamster ovary (CHO) cells or a cell of *Cricetulus griseus.*

13. The polynucleotide of claim 4, wherein the eukaryotic host is a fungal host or an animal host, wherein the fungal host comprises a cell of *Trichoderma, Trichoderma reesei, Pichia, Pichia pastoris, Pichia kudriavzevii, Aspergillus, Aspergillus niger, Aspergillus oryzae, Myceliophthora, Myceliophthora thermophila, Saccharomyces, Saccharomyces cerevisiae, Yarrowia, Yarrowia lipolytica, Cutaneotrichosporon, Cutaneotrichosporon oleaginosus, Trichosporon oleaginosus, Cryptococcus curvatus*, or *Zygosaccharomyces*, or wherein the animal host comprises Chinese hamster ovary (CHO) cells or a cell of *Cricetulus griseus*.

14. The polynucleotide of claim 9 wherein the eukaryotic host is a fungal host or an animal host, wherein the fungal host comprises a cell of *Trichoderma, Trichoderma reesei, Pichia, Pichia pastoris, Pichia kudriavzevii, Aspergillus, Aspergillus niger, Aspergillus oryzae, Myceliophthora, Myceliophthora thermophila, Saccharomyces, Saccharomyces cerevisiae, Yarrowia, Yarrowia lipolytica, Cutaneotrichosporon, Cutaneotrichosporon oleaginosus, Trichosporon oleaginosus, Cryptococcus curvatus*, or *Zygosaccharomyces*, or wherein the animal host comprises Chinese hamster ovary (CHO) cells or a cell of *Cricetulus griseus*.

15. The eukaryotic host of claim 6, wherein the eukaryotic host is a fungal host or an animal host, wherein the fungal host comprises a cell of *Trichoderma, Trichoderma reesei, Pichia, Pichia pastoris, Pichia kudriavzevii, Aspergillus, Aspergillus niger, Aspergillus oryzae, Myceliophthora, Myceliophthora thermophila, Saccharomyces, Saccharomyces cerevisiae, Yarrowia, Yarrowia lipolytica, Cutaneotrichosporon, Cutaneotrichosporon oleaginosus, Trichosporon oleaginosus, Cryptococcus curvatus*, or *Zygosaccharomyces*, or wherein the animal host comprises Chinese hamster ovary (CHO) cells or a cell of *Cricetulus griseus*.

16. A method for producing a desired protein product in a eukaryotic host comprising cultivating the host of claim 10 under suitable cultivation conditions.

17. A method for producing a desired protein product in a eukaryotic host comprising cultivating the host of claim 11 under suitable cultivation conditions.

* * * * *

SEQUENCE LISTING

<160> NUMBER OF SEQ ID NOS: 44

<210> SEQ ID NO 1
<211> LENGTH: 80
<212> TYPE: PRT
<213> ORGANISM: Artificial Sequence
<220> FEATURE:
<223> OTHER INFORMATION: VP16-AD was used as the transcription activation domain in a control construct

<400> SEQUENCE: 1

Ser Thr Ala Pro Pro Thr Asp Val Ser Leu Gly Asp Glu Leu His Leu
1 5 10 15

Asp Gly Glu Asp Val Ala Met Ala His Ala Asp Ala Leu Asp Asp Phe
20 25 30

Asp Leu Asp Met Leu Gly Asp Gly Asp Ser Pro Gly Pro Gly Phe Thr
35 40 45

Pro His Asp Ser Ala Pro Tyr Gly Ala Leu Asp Met Ala Asp Phe Glu
50 55 60

Phe Glu Gln Met Phe Thr Asp Ala Leu Gly Ile Asp Glu Tyr Gly Gly
65 70 75 80

<210> SEQ ID NO 2
<211> LENGTH: 90
<212> TYPE: PRT
<213> ORGANISM: Artificial Sequence
<220> FEATURE:
<223> OTHER INFORMATION: At_NAC102, Region of amino-acid sequence 126 - 215 from the AT5G63790 protein of Arabidopsis thaliana (GenBank: BAH57132.1)

<400> SEQUENCE: 2

Thr Ser Asp Ser Arg Cys Ser Ser His Val Ile Ser Pro Asp Val Thr
1 5 10 15

Cys Ser Asp Asn Trp Glu Val Glu Ser Glu Pro Lys Trp Ile Asn Leu
20 25 30

Glu Asp Ala Leu Glu Ala Phe Asn Asp Asp Thr Ser Met Phe Ser Ser
35 40 45

Ile Gly Leu Leu Gln Asn Asp Ala Phe Val Pro Gln Phe Gln Tyr Gln
50 55 60

Ser Ser Asp Phe Val Asp Ser Phe Gln Asp Pro Phe Glu Gln Lys Pro
65 70 75 80

Phe Leu Asn Trp Asn Phe Ala Pro Gln Gly
85 90

<210> SEQ ID NO 3
<211> LENGTH: 131
<212> TYPE: PRT
<213> ORGANISM: Artificial Sequence
<220> FEATURE:
<223> OTHER INFORMATION: So_NAC102, Region of amino-acid sequence 173 - 303 from the NAC domain-containing protein 2 of Spinacia oleracea (NCBI Reference Sequence: XP_021863783.1)

<400> SEQUENCE: 3

Pro Met Ser Met Pro Thr Ser Ile Thr Gln Tyr Pro Glu Phe Glu Asp
1 5 10 15

Gln Lys Pro Val Ile Ser Thr Leu Gly Gln Thr Gly Pro Met Gly Tyr
20 25 30

Asn Met Thr Thr Thr Ser Pro Ile Pro Gln Pro Lys Asn Asp Leu Met
35 40 45

```
His Phe Asp Thr Ser Asp Ser Val Pro Arg Cys His Thr Asp Thr Ser
    50                  55                  60

Gly Ser Asn His Val Ala Ser Pro Glu Phe Met Cys Asp Lys Glu Val
65                  70                  75                  80

Gln Ser Asp Pro Lys Trp Asn Glu Leu Glu Lys Asn Leu Asp Phe Pro
                85                  90                  95

Ser Phe Asn Tyr Met Glu Pro Phe Pro Asp Asp Pro Phe Thr Ser Thr
            100                 105                 110

Ala Gln Phe His Asn Asp Gln Met Gly Asn Tyr Gln Asp Ile Phe Met
        115                 120                 125

Leu Leu Arg
    130


<210> SEQ ID NO 4
<211> LENGTH: 101
<212> TYPE: PRT
<213> ORGANISM: Artificial Sequence
<220> FEATURE:
<223> OTHER INFORMATION: At_TAF1, Region of amino-acid sequence 129 -
      229 from the ATAF1 protein of Arabidopsis thaliana (GenBank:
      CAA52771.1)

<400> SEQUENCE: 4

Met Pro Pro Pro Pro Gln Gln Thr Ser Glu Phe Ala Tyr Phe Asp Thr
1               5                   10                  15

Ser Asp Ser Val Pro Lys Leu His Thr Thr Asp Ser Ser Cys Ser Glu
            20                  25                  30

Gln Val Val Ser Pro Glu Phe Thr Ser Glu Val Gln Ser Glu Pro Lys
        35                  40                  45

Trp Lys Asp Trp Ser Ala Val Ser Asn Asp Asn Asn Asn Thr Leu Asp
    50                  55                  60

Phe Gly Phe Asn Tyr Ile Asp Ala Thr Val Asp Asn Ala Phe Gly Gly
65                  70                  75                  80

Gly Gly Ser Ser Asn Gln Met Phe Pro Leu Gln Asp Met Phe Met Tyr
                85                  90                  95

Met Gln Lys Pro Tyr
            100


<210> SEQ ID NO 5
<211> LENGTH: 185
<212> TYPE: PRT
<213> ORGANISM: Artificial Sequence
<220> FEATURE:
<223> OTHER INFORMATION: So_NAC72, Region of amino-acid sequence 185 -
      369 from the NAC domain-containing protein 72 of Spinacia oleracea
      (NCBI Reference Sequence: XP_021840466.1)

<400> SEQUENCE: 5

Ser Ser His Leu Asp Asp Val Leu Glu Ser Leu Pro Glu Ile Asp His
1               5                   10                  15

Arg Ser Phe Ala Leu Pro Arg Met Asn Ser Phe Lys Asn Ser Asn Ser
            20                  25                  30

Asn Ser Asn Val Ala Gln Gln Gln Gln Gln Gln His Gln Gln Gln Gln
        35                  40                  45

Gln Gln Gln His Gln Gln Gln Gln Asn Pro Gln Ser His Lys Phe Asn
    50                  55                  60

Leu Gln Gln Leu Gly Ser Gly Ser Phe Asp Trp Ala Phe Leu Ala Gly
65                  70                  75                  80

Leu Thr Ser Val Pro Glu Tyr Thr Phe Asn Gly Ser Thr Gln Pro Gln
```

```
                85                  90                  95

Ser Gly Asn Asn Asn Gly Asn Asp Met Phe Val Pro Ser Leu Pro Pro
            100                 105                 110

Leu Ser Gln Val Glu Ser Ser Val Asp Asn Lys Leu Arg Thr Thr Arg
        115                 120                 125

Leu Ser Asp Glu Glu Val Gln Ser Gly Ile Ser Thr Asn Gln Arg Phe
    130                 135                 140

Asn Ser Gly Tyr Phe Asn His Asn Asn Thr Asn Val Phe Thr Gln Asn
145                 150                 155                 160

Tyr His Asn Ser Met Asp Leu Phe Gly Thr Gly His Ser Asn Gln Phe
                165                 170                 175

Ser Gly Phe Gly Phe Gly Phe Arg Gln
            180                 185


<210> SEQ ID NO 6
<211> LENGTH: 100
<212> TYPE: PRT
<213> ORGANISM: Artificial Sequence
<220> FEATURE:
<223> OTHER INFORMATION: Bn_TAF1, Region of amino-acid sequence 186 -
      286 from the NAC domain-containing protein 2 of Brassica napus
      (NCBI Reference Sequence: NP_001302866.1)

<400> SEQUENCE: 6

Glu Met Gly Met Pro Pro Pro Pro Val Met Pro Asn Asp Phe Val Tyr
1               5                   10                  15

Phe Asp Thr Ser Asp Ser Val Pro Lys Leu His Thr Thr Glu Ser Ser
            20                  25                  30

Cys Ser Glu Gln Val Val Ser Pro Glu Phe Thr Ser Glu Val Gln Ser
        35                  40                  45

Glu Pro Lys Trp Lys Asp Trp Ser Gly Ala Ala Asn Asp Lys Asn Ser
    50                  55                  60

Leu Asp Phe Gly Phe Asn Tyr Ile Asp Ala Thr Ala Phe Gly Gly Val
65                  70                  75                  80

Gly Ser Asn Gln Leu Phe Pro Leu Gln Asp Met Phe Met Tyr Asn Met
                85                  90                  95

Pro Lys Pro Tyr
            100


<210> SEQ ID NO 7
<211> LENGTH: 92
<212> TYPE: PRT
<213> ORGANISM: Artificial Sequence
<220> FEATURE:
<223> OTHER INFORMATION: At_JUB1, Region of amino-acid sequence 106 -
      197 from the NAC domain containing protein 42 of Arabidopsis
      thaliana (NCBI Reference Sequence: NP_001324496.1)

<400> SEQUENCE: 7

Val Ile Thr Leu Thr Asp Thr Cys Ser Lys Thr Ser Ser Leu Asp Ser
1               5                   10                  15

Asp His Thr Ser His Arg Thr Val Asp Ser Met Ser His Glu Pro Pro
            20                  25                  30

Leu Pro Gln Pro Gln Asn Pro Tyr Trp Asn Gln His Ile Val Gly Phe
        35                  40                  45

Asn Gln Pro Thr Tyr Thr Gly Asn Asp Asn Asn Leu Leu Met Ser Phe
    50                  55                  60

Trp Asn Gly Asn Gly Gly Asp Phe Ile Gly Asp Ser Ala Ser Trp Asp
65                  70                  75                  80
```

```
Glu Leu Arg Ser Val Ile Asp Gly Asn Thr Lys Pro
                85                  90


<210> SEQ ID NO 8
<211> LENGTH: 131
<212> TYPE: PRT
<213> ORGANISM: Artificial Sequence
<220> FEATURE:
<223> OTHER INFORMATION: So_JUB1, Region of amino-acid sequence 227 -
      357 from the JUNGBRUNNEN 1-like protein of Spinacia oleracea (NCBI
      Reference Sequence: XP_021854333.1)

<400> SEQUENCE: 8

Ser Arg Ser Lys Asn Ala Val Asn Ser Ser Ser Lys Thr Ser Ser Ile
1               5                   10                  15

Asp Ser Asn Thr Asn Gln Glu Cys Tyr Ile Ser Phe Gly Thr His Gln
            20                  25                  30

Ala Ala Ala Ala Leu Asp Asn Gly Tyr Asn Asn Leu Leu Val Ala Asn
        35                  40                  45

Gln Gly Asp Asn Asn Asn Asn Asn Thr Asn Asn Ile Tyr Thr Gly Asn
    50                  55                  60

Gln Asn Ile Thr Thr Gly Ser His Ala Asp His Gln Gln Trp Asn Leu
65                  70                  75                  80

Met Ser His Thr Pro Ser Cys Thr Ser Arg Pro Ser Thr Met Ser His
                85                  90                  95

Val Leu Thr Asn Asp Gly Asn Asp Leu Gln Asn Phe Ala Tyr Tyr Gln
            100                 105                 110

His Asn Trp Asp Asp Leu Asn Ser Val Val Glu Leu Ala Val Lys Asn
        115                 120                 125

Pro Phe Leu
    130


<210> SEQ ID NO 9
<211> LENGTH: 91
<212> TYPE: PRT
<213> ORGANISM: Artificial Sequence
<220> FEATURE:
<223> OTHER INFORMATION: Bn_JUB1, Region of amino-acid sequence 189 -
      279 from the JUNGBRUNNEN 1 protein of Brassica napus (NCBI
      Reference Sequence: XP_013670411.1)

<400> SEQUENCE: 9

Cys Ser Lys Thr Ser Ser Leu Asp Ser Asp His Thr Ser His Arg Val
1               5                   10                  15

Val Asp Ser Leu Ser His Lys Leu His Glu Pro His Leu Gln Leu Gln
            20                  25                  30

Ser Pro Thr Gln Asn Pro Tyr Trp Asn Gln Leu Thr Arg Phe Gly Phe
        35                  40                  45

Asn Gln Pro Thr Tyr Thr Cys His Asp Asn Ser Leu Leu Ser Phe Glu
    50                  55                  60

Asn Ile Asn Gly Gly Asp Phe Ile Gly Asp Ser Ala Ser Trp Asp Glu
65                  70                  75                  80

Leu Arg Ser Val Ile Asp Gly Asn Thr Lys His
                85                  90


<210> SEQ ID NO 10
<211> LENGTH: 128
<212> TYPE: PRT
<213> ORGANISM: Artificial Sequence
<220> FEATURE:
```

<223> OTHER INFORMATION: So_NAC102M, So_NAC102-AD with following amino-
acid changes: Removal (deletion) of amino acids 1-3, and mutations
K18L, K44L, R58D, C59L, K78L, K85L, and K91D

<400> SEQUENCE: 10

Met Pro Thr Ser Ile Thr Gln Tyr Pro Glu Phe Glu Asp Gln Leu Pro
1 5 10 15

Val Ile Ser Thr Leu Gly Gln Thr Gly Pro Met Gly Tyr Asn Met Thr
20 25 30

Thr Thr Ser Pro Ile Pro Gln Pro Leu Asn Asp Leu Met His Phe Asp
35 40 45

Thr Ser Asp Ser Val Pro Asp Leu His Thr Asp Thr Ser Gly Ser Asn
50 55 60

His Val Ala Ser Pro Glu Phe Met Cys Asp Leu Glu Val Gln Ser Asp
65 70 75 80

Pro Leu Trp Asn Glu Leu Glu Asp Asn Leu Asp Phe Pro Ser Phe Asn
85 90 95

Tyr Met Glu Pro Phe Pro Asp Asp Pro Phe Thr Ser Thr Ala Gln Phe
100 105 110

His Asn Asp Gln Met Gly Asn Tyr Gln Asp Ile Phe Met Leu Leu Arg
115 120 125

<210> SEQ ID NO 11
<211> LENGTH: 100
<212> TYPE: PRT
<213> ORGANISM: Artificial Sequence
<220> FEATURE:
<223> OTHER INFORMATION: Bn_TAF1M, Bn_TAF1-AD with following amino-acid
changes: K25D, K51L, K53D, K62D.

<400> SEQUENCE: 11

Glu Met Gly Met Pro Pro Pro Pro Val Met Pro Asn Asp Phe Val Tyr
1 5 10 15

Phe Asp Thr Ser Asp Ser Val Pro Asp Leu His Thr Thr Glu Ser Ser
20 25 30

Cys Ser Glu Gln Val Val Ser Pro Glu Phe Thr Ser Glu Val Gln Ser
35 40 45

Glu Pro Leu Trp Asp Asp Trp Ser Gly Ala Ala Asn Asp Asp Asn Ser
50 55 60

Leu Asp Phe Gly Phe Asn Tyr Ile Asp Ala Thr Ala Phe Gly Gly Gly
65 70 75 80

Gly Ser Asn Gln Leu Phe Pro Leu Gln Asp Met Phe Met Tyr Asn Met
85 90 95

Pro Lys Pro Tyr
100

<210> SEQ ID NO 12
<211> LENGTH: 102
<212> TYPE: PRT
<213> ORGANISM: Artificial Sequence
<220> FEATURE:
<223> OTHER INFORMATION: At_NAC102 with a nuclear localization signal

<400> SEQUENCE: 12

Pro Pro Lys Lys Lys Arg Lys Val Gly Ser Gly Ser Thr Ser Asp Ser
1 5 10 15

Arg Cys Ser Ser His Val Ile Ser Pro Asp Val Thr Cys Ser Asp Asn
20 25 30

Trp Glu Val Glu Ser Glu Pro Lys Trp Ile Asn Leu Glu Asp Ala Leu

```
        35                  40                  45

Glu Ala Phe Asn Asp Asp Thr Ser Met Phe Ser Ser Ile Gly Leu Leu
    50                  55                  60

Gln Asn Asp Ala Phe Val Pro Gln Phe Gln Tyr Gln Ser Ser Asp Phe
65                  70                  75                  80

Val Asp Ser Phe Gln Asp Pro Phe Glu Gln Lys Pro Phe Leu Asn Trp
                85                  90                  95

Asn Phe Ala Pro Gln Gly
            100


<210> SEQ ID NO 13
<211> LENGTH: 143
<212> TYPE: PRT
<213> ORGANISM: Artificial Sequence
<220> FEATURE:
<223> OTHER INFORMATION: So_NAC102 with a nuclear localization signal

<400> SEQUENCE: 13

Pro Pro Lys Lys Lys Arg Lys Val Gly Ser Gly Ser Pro Met Ser Met
1               5                   10                  15

Pro Thr Ser Ile Thr Gln Tyr Pro Glu Phe Glu Asp Gln Lys Pro Val
            20                  25                  30

Ile Ser Thr Leu Gly Gln Thr Gly Pro Met Gly Tyr Asn Met Thr Thr
        35                  40                  45

Thr Ser Pro Ile Pro Gln Pro Lys Asn Asp Leu Met His Phe Asp Thr
    50                  55                  60

Ser Asp Ser Val Pro Arg Cys His Thr Asp Thr Ser Gly Ser Asn His
65                  70                  75                  80

Val Ala Ser Pro Glu Phe Met Cys Asp Lys Glu Val Gln Ser Asp Pro
                85                  90                  95

Lys Trp Asn Glu Leu Glu Lys Asn Leu Asp Phe Pro Ser Phe Asn Tyr
            100                 105                 110

Met Glu Pro Phe Pro Asp Asp Pro Phe Thr Ser Thr Ala Gln Phe His
        115                 120                 125

Asn Asp Gln Met Gly Asn Tyr Gln Asp Ile Phe Met Leu Leu Arg
    130                 135                 140


<210> SEQ ID NO 14
<211> LENGTH: 113
<212> TYPE: PRT
<213> ORGANISM: Artificial Sequence
<220> FEATURE:
<223> OTHER INFORMATION: At_TAF1 with a nuclear localization signal

<400> SEQUENCE: 14

Pro Pro Lys Lys Lys Arg Lys Val Gly Ser Gly Ser Met Pro Pro Pro
1               5                   10                  15

Pro Gln Gln Thr Ser Glu Phe Ala Tyr Phe Asp Thr Ser Asp Ser Val
            20                  25                  30

Pro Lys Leu His Thr Thr Asp Ser Ser Cys Ser Glu Gln Val Val Ser
        35                  40                  45

Pro Glu Phe Thr Ser Glu Val Gln Ser Glu Pro Lys Trp Lys Asp Trp
    50                  55                  60

Ser Ala Val Ser Asn Asp Asn Asn Asn Thr Leu Asp Phe Gly Phe Asn
65                  70                  75                  80

Tyr Ile Asp Ala Thr Val Asp Asn Ala Phe Gly Gly Gly Gly Ser Ser
                85                  90                  95
```

Asn Gln Met Phe Pro Leu Gln Asp Met Phe Met Tyr Met Gln Lys Pro
100 105 110

Tyr

<210> SEQ ID NO 15
<211> LENGTH: 197
<212> TYPE: PRT
<213> ORGANISM: Artificial Sequence
<220> FEATURE:
<223> OTHER INFORMATION: So_NAC72 with a nuclear localisation signal

<400> SEQUENCE: 15

Pro Pro Lys Lys Lys Arg Lys Val Gly Ser Gly Ser Ser Ser His Leu
1 5 10 15

Asp Asp Val Leu Glu Ser Leu Pro Glu Ile Asp His Arg Ser Phe Ala
20 25 30

Leu Pro Arg Met Asn Ser Phe Lys Asn Ser Asn Ser Asn Ser Asn Val
35 40 45

Ala Gln Gln Gln Gln Gln Gln His Gln Gln Gln Gln Gln Gln Gln His
50 55 60

Gln Gln Gln Gln Asn Pro Gln Ser His Lys Phe Asn Leu Gln Gln Leu
65 70 75 80

Gly Ser Gly Ser Phe Asp Trp Ala Phe Leu Ala Gly Leu Thr Ser Val
85 90 95

Pro Glu Tyr Thr Phe Asn Gly Ser Thr Gln Pro Gln Ser Gly Asn Asn
100 105 110

Asn Gly Asn Asp Met Phe Val Pro Ser Leu Pro Pro Leu Ser Gln Val
115 120 125

Glu Ser Ser Val Asp Asn Lys Leu Arg Thr Thr Arg Leu Ser Asp Glu
130 135 140

Glu Val Gln Ser Gly Ile Ser Thr Asn Gln Arg Phe Asn Ser Gly Tyr
145 150 155 160

Phe Asn His Asn Asn Thr Asn Val Phe Thr Gln Asn Tyr His Asn Ser
165 170 175

Met Asp Leu Phe Gly Thr Gly His Ser Asn Gln Phe Ser Gly Phe Gly
180 185 190

Phe Gly Phe Arg Gln
195

<210> SEQ ID NO 16
<211> LENGTH: 112
<212> TYPE: PRT
<213> ORGANISM: Artificial Sequence
<220> FEATURE:
<223> OTHER INFORMATION: Bn_TAF1 with a nuclear localisation signal

<400> SEQUENCE: 16

Pro Pro Lys Lys Lys Arg Lys Val Gly Ser Gly Ser Glu Met Gly Met
1 5 10 15

Pro Pro Pro Pro Val Met Pro Asn Asp Phe Val Tyr Phe Asp Thr Ser
20 25 30

Asp Ser Val Pro Lys Leu His Thr Thr Glu Ser Ser Cys Ser Glu Gln
35 40 45

Val Val Ser Pro Glu Phe Thr Ser Glu Val Gln Ser Glu Pro Lys Trp
50 55 60

Lys Asp Trp Ser Gly Ala Ala Asn Asp Lys Asn Ser Leu Asp Phe Gly
65 70 75 80

Phe Asn Tyr Ile Asp Ala Thr Ala Phe Gly Gly Val Gly Ser Asn Gln
85 90 95

Leu Phe Pro Leu Gln Asp Met Phe Met Tyr Asn Met Pro Lys Pro Tyr
100 105 110

<210> SEQ ID NO 17
<211> LENGTH: 104
<212> TYPE: PRT
<213> ORGANISM: Artificial Sequence
<220> FEATURE:
<223> OTHER INFORMATION: At_JUB1 with a nuclear localization signal

<400> SEQUENCE: 17

Pro Pro Lys Lys Lys Arg Lys Val Gly Ser Gly Ser Val Ile Thr Leu
1 5 10 15

Thr Asp Thr Cys Ser Lys Thr Ser Ser Leu Asp Ser Asp His Thr Ser
20 25 30

His Arg Thr Val Asp Ser Met Ser His Glu Pro Pro Leu Pro Gln Pro
35 40 45

Gln Asn Pro Tyr Trp Asn Gln His Ile Val Gly Phe Asn Gln Pro Thr
50 55 60

Tyr Thr Gly Asn Asp Asn Asn Leu Leu Met Ser Phe Trp Asn Gly Asn
65 70 75 80

Gly Gly Asp Phe Ile Gly Asp Ser Ala Ser Trp Asp Glu Leu Arg Ser
85 90 95

Val Ile Asp Gly Asn Thr Lys Pro
100

<210> SEQ ID NO 18
<211> LENGTH: 139
<212> TYPE: PRT
<213> ORGANISM: Artificial Sequence
<220> FEATURE:
<223> OTHER INFORMATION: So_JUB1 with a nuclear localisation signal

<400> SEQUENCE: 18

Pro Pro Lys Lys Lys Arg Lys Val Ser Arg Ser Lys Asn Ala Val Asn
1 5 10 15

Ser Ser Ser Lys Thr Ser Ser Ile Asp Ser Asn Thr Asn Gln Glu Cys
20 25 30

Tyr Ile Ser Phe Gly Thr His Gln Ala Ala Ala Ala Leu Asp Asn Gly
35 40 45

Tyr Asn Asn Leu Leu Val Ala Asn Gln Gly Asp Asn Asn Asn Asn Asn
50 55 60

Thr Asn Asn Ile Tyr Thr Gly Asn Gln Asn Ile Thr Thr Gly Ser His
65 70 75 80

Ala Asp His Gln Gln Trp Asn Leu Met Ser His Thr Pro Ser Cys Thr
85 90 95

Ser Arg Pro Ser Thr Met Ser His Val Leu Thr Asn Asp Gly Asn Asp
100 105 110

Leu Gln Asn Phe Ala Tyr Tyr Gln His Asn Trp Asp Asp Leu Asn Ser
115 120 125

Val Val Glu Leu Ala Val Lys Asn Pro Phe Leu
130 135

<210> SEQ ID NO 19
<211> LENGTH: 103
<212> TYPE: PRT
<213> ORGANISM: Artificial Sequence
<220> FEATURE:
<223> OTHER INFORMATION: Bn_JUB1 with a nuclear localisation signal

<400> SEQUENCE: 19

Pro Pro Lys Lys Lys Arg Lys Val Gly Ser Gly Ser Cys Ser Lys Thr
1 5 10 15

Ser Ser Leu Asp Ser Asp His Thr Ser His Arg Val Val Asp Ser Leu
20 25 30

Ser His Lys Leu His Glu Pro His Leu Gln Leu Gln Ser Pro Thr Gln
35 40 45

Asn Pro Tyr Trp Asn Gln Leu Thr Arg Phe Gly Phe Asn Gln Pro Thr
50 55 60

Tyr Thr Cys His Asp Asn Ser Leu Leu Ser Phe Glu Asn Ile Asn Gly
65 70 75 80

Gly Asp Phe Ile Gly Asp Ser Ala Ser Trp Asp Glu Leu Arg Ser Val
85 90 95

Ile Asp Gly Asn Thr Lys His
100

<210> SEQ ID NO 20
<211> LENGTH: 140
<212> TYPE: PRT
<213> ORGANISM: Artificial Sequence
<220> FEATURE:
<223> OTHER INFORMATION: So_NAC102M with a nuclear localisation signal

<400> SEQUENCE: 20

Pro Pro Lys Lys Lys Arg Lys Val Gly Ser Gly Ser Met Pro Thr Ser
1 5 10 15

Ile Thr Gln Tyr Pro Glu Phe Glu Asp Gln Leu Pro Val Ile Ser Thr
20 25 30

Leu Gly Gln Thr Gly Pro Met Gly Tyr Asn Met Thr Thr Thr Ser Pro
35 40 45

Ile Pro Gln Pro Leu Asn Asp Leu Met His Phe Asp Thr Ser Asp Ser
50 55 60

Val Pro Asp Leu His Thr Asp Thr Ser Gly Ser Asn His Val Ala Ser
65 70 75 80

Pro Glu Phe Met Cys Asp Leu Glu Val Gln Ser Asp Pro Leu Trp Asn
85 90 95

Glu Leu Glu Asp Asn Leu Asp Phe Pro Ser Phe Asn Tyr Met Glu Pro
100 105 110

Phe Pro Asp Asp Pro Phe Thr Ser Thr Ala Gln Phe His Asn Asp Gln
115 120 125

Met Gly Asn Tyr Gln Asp Ile Phe Met Leu Leu Arg
130 135 140

<210> SEQ ID NO 21
<211> LENGTH: 112
<212> TYPE: PRT
<213> ORGANISM: Artificial Sequence
<220> FEATURE:
<223> OTHER INFORMATION: Bn_TAF1M with a nuclear localisation signal

<400> SEQUENCE: 21

Pro Pro Lys Lys Lys Arg Lys Val Gly Ser Gly Ser Glu Met Gly Met
1 5 10 15

Pro Pro Pro Pro Val Met Pro Asn Asp Phe Val Tyr Phe Asp Thr Ser
20 25 30

```
Asp Ser Val Pro Asp Leu His Thr Thr Glu Ser Ser Cys Ser Glu Gln
        35                  40                  45

Val Val Ser Pro Glu Phe Thr Ser Glu Val Gln Ser Glu Pro Leu Trp
    50                  55                  60

Asp Asp Trp Ser Gly Ala Ala Asn Asp Asp Asn Ser Leu Asp Phe Gly
65                  70                  75                  80

Phe Asn Tyr Ile Asp Ala Thr Ala Phe Gly Gly Gly Gly Ser Asn Gln
                85                  90                  95

Leu Phe Pro Leu Gln Asp Met Phe Met Tyr Asn Met Pro Lys Pro Tyr
            100                 105                 110


<210> SEQ ID NO 22
<211> LENGTH: 209
<212> TYPE: DNA
<213> ORGANISM: Artificial Sequence
<220> FEATURE:
<223> OTHER INFORMATION: An_008cp core promoter

<400> SEQUENCE: 22

aacccaaagt aataagtctg tagtaattgg tctcgccctg aattccaaac tataaatcaa      60

ccactttccc tcctcccccc cgcccccact tggtcgattc ttcgttttct ctctaccttc     120

tttctattcg gttttcttct tcttttattt tccctctccc atcaatcaaa ttcatatttg     180

aaaaaaatta acattaataa atatctaca                                        209


<210> SEQ ID NO 23
<211> LENGTH: 145
<212> TYPE: DNA
<213> ORGANISM: Artificial Sequence
<220> FEATURE:
<223> OTHER INFORMATION: An_201cp core promoter

<400> SEQUENCE: 23

ttctcttttc ttaagaatat gttcaaagac taggatggat aaatggggta tataaagcac      60

cctgactccc ttcctccaag ttctatctaa ccagccatcc tacactctac atatccacac     120

caatctacta caattattaa ttaaa                                            145


<210> SEQ ID NO 24
<211> LENGTH: 414
<212> TYPE: PRT
<213> ORGANISM: Artificial Sequence
<220> FEATURE:
<223> OTHER INFORMATION: a phytase enzyme, thermo-stable mutated version
      Ap-pA_K24E

<400> SEQUENCE: 24

Gln Ser Glu Pro Glu Leu Lys Leu Glu Ser Val Val Ile Val Ser Arg
1               5                   10                  15

His Gly Val Arg Ala Pro Thr Glu Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Thr Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Ser Val
```

-continued 100 105 110

His Thr Gln Ala Asp Thr Ser Ser Pro Asp Pro Leu Phe Asn Pro Leu
115 120 125

Lys Thr Gly Val Cys Gln Leu Asp Asn Ala Asn Val Thr Asp Ala Ile
130 135 140

Leu Ser Arg Ala Gly Gly Ser Ile Ala Asp Phe Thr Gly His Arg Gln
145 150 155 160

Thr Ala Phe Arg Glu Leu Glu Arg Val Leu Asn Phe Pro Gln Ser Asn
165 170 175

Leu Cys Leu Asn Arg Glu Lys Gln Asp Glu Ser Cys Ser Leu Thr Gln
180 185 190

Ala Leu Pro Ser Glu Leu Lys Val Ser Ala Asp Asn Val Ser Leu Thr
195 200 205

Gly Ala Val Ser Leu Ala Ser Met Leu Thr Glu Ile Phe Leu Leu Gln
210 215 220

Gln Ala Gln Gly Met Pro Glu Pro Gly Trp Gly Arg Ile Thr Asp Ser
225 230 235 240

His Gln Trp Asn Thr Leu Leu Ser Leu His Asn Ala Gln Phe Tyr Leu
245 250 255

Leu Gln Arg Thr Pro Glu Val Ala Arg Ser Arg Ala Thr Pro Leu Leu
260 265 270

Asp Leu Ile Met Thr Ala Leu Met Pro His Pro Pro Gln Lys Gln Val
275 280 285

Tyr Gly Val Thr Leu Pro Thr Ser Val Leu Phe Ile Ala Gly His Asp
290 295 300

Thr Asn Leu Ala Asn Leu Gly Gly Ala Leu Glu Leu Asn Trp Thr Leu
305 310 315 320

Pro Gly Gln Pro Asp Asn Thr Pro Pro Gly Gly Glu Leu Val Phe Glu
325 330 335

Arg Trp Arg Arg Leu Ser Asp Asn Ser His Trp Ile Gln Val Ser Leu
340 345 350

Val Phe Gln Thr Leu Gln Gln Met Arg Asp Lys Thr Pro Leu Ser Leu
355 360 365

Asn Thr Pro Pro Gly Glu Val Lys Leu Thr Leu Ala Gly Cys Glu Glu
370 375 380

Arg Asn Ala Gln Gly Met Cys Ser Leu Ala Gly Phe Thr Gln Ile Val
385 390 395 400

Asn Glu Ala Arg Ile Pro Ala Cys Ala Leu His Gln Asp Lys
405 410

<210> SEQ ID NO 25
<211> LENGTH: 200
<212> TYPE: DNA
<213> ORGANISM: Artificial Sequence
<220> FEATURE:
<223> OTHER INFORMATION: Tr_hfb2cp core promoter

<400> SEQUENCE: 25
aacagcctgc gagagctgga agatgaagag ggccagaaaa aaaagtataa agaagacctc 60
gattcccgcc atccaacaat cttttccatc ctcatcagca cactcatcta caaccatcac 120
cacattcact caactcctct ttctcaactc tccaaacaca aacattcttt gttgaatacc 180
aaccatcacc acttataaca 200

<210> SEQ ID NO 26

<211> LENGTH: 184
<212> TYPE: DNA
<213> ORGANISM: Artificial Sequence
<220> FEATURE:
<223> OTHER INFORMATION: Mm_Atp5Bcp core promoter

<400> SEQUENCE: 26
attggcacca gtttagacca atagctgata agctccgagt ttttttaccc tatagaagcg 60
ttagtggtga tgacgaacag caaaatcacc caattactgt gcctacggcg gaggttgccc 120
cgccccagct gcaggaccgg cggagaggac cgcttcggcg ctcagtctcc acccggattc 180
cgcc 184

<210> SEQ ID NO 27
<211> LENGTH: 161
<212> TYPE: DNA
<213> ORGANISM: Artificial Sequence
<220> FEATURE:
<223> OTHER INFORMATION: Mm_Eef2cp core promoter

<400> SEQUENCE: 27
ccggacgagc acccggcgcc gtcacgtgac gcacccaacc ggcgttgacc tataaaaggc 60
cgggcgttga cgtcagcggt ctcttccgcc gcagccgccg ccatcgtcgg cgcgcttccc 120
tgttcacctc tgactctgag aatccgtcgc catccgccac c 161

<210> SEQ ID NO 28
<211> LENGTH: 134
<212> TYPE: DNA
<213> ORGANISM: Artificial Sequence
<220> FEATURE:
<223> OTHER INFORMATION: Mm_Rpl4cp core promoter

<400> SEQUENCE: 28
ctctaatttg attttgataa ggggcaggat gcggaagacg agtggaagga tatatagagt 60
acaagtgaca agtctttcct tttcctgtgg gagcagccgg gtagagagga gcgtggcctt 120
ctcctctccc cgtc 134

<210> SEQ ID NO 29
<211> LENGTH: 162
<212> TYPE: PRT
<213> ORGANISM: Artificial Sequence
<220> FEATURE:
<223> OTHER INFORMATION: a bovine -Lactoglobulin B protein

<400> SEQUENCE: 29

Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
            20                  25                  30

Asp Ala Gln Ser Ala Pro Leu Arg Val Tyr Val Glu Glu Leu Lys Pro
        35                  40                  45

Thr Pro Glu Gly Asp Leu Glu Ile Leu Leu Gln Lys Trp Glu Asn Gly
    50                  55                  60

Glu Cys Ala Gln Lys Lys Ile Ile Ala Glu Lys Thr Lys Ile Pro Ala
65                  70                  75                  80

Val Phe Lys Ile Asp Ala Leu Asn Glu Asn Lys Val Leu Val Leu Asp
                85                  90                  95

Thr Asp Tyr Lys Lys Tyr Leu Leu Phe Cys Met Glu Asn Ser Ala Glu
            100                 105                 110

```
Pro Glu Gln Ser Leu Ala Cys Gln Cys Leu Val Arg Thr Pro Glu Val
        115                 120                 125

Asp Asp Glu Ala Leu Glu Lys Phe Asp Lys Ala Leu Lys Ala Leu Pro
    130                 135                 140

Met His Ile Arg Leu Ser Phe Asn Pro Thr Gln Leu Glu Glu Gln Cys
145                 150                 155                 160

His Ile


<210> SEQ ID NO 30
<211> LENGTH: 62
<212> TYPE: PRT
<213> ORGANISM: Artificial Sequence
<220> FEATURE:
<223> OTHER INFORMATION: VP64 activation domain

<400> SEQUENCE: 30

Ser Ala Ser Gly Ser Gly Arg Ala Asp Ala Leu Asp Asp Phe Asp Leu
1               5                   10                  15

Asp Met Leu Gly Ser Asp Ala Leu Asp Asp Phe Asp Leu Asp Met Leu
            20                  25                  30

Gly Ser Asp Ala Leu Asp Asp Phe Asp Leu Asp Met Leu Gly Ser Asp
        35                  40                  45

Ala Leu Asp Asp Phe Asp Leu Asp Met Leu Ile Asn Ser Arg
    50                  55                  60


<210> SEQ ID NO 31
<211> LENGTH: 201
<212> TYPE: PRT
<213> ORGANISM: Artificial Sequence
<220> FEATURE:
<223> OTHER INFORMATION: an alkaline xylanase, thermo-stable mutated
      version xynHB_N188A

<400> SEQUENCE: 31

Ala Glu Thr Ile Tyr Asp Asn Arg Ile Gly Thr His Ser Gly Tyr Asp
1               5                   10                  15

Phe Glu Leu Trp Lys Asp Tyr Gly Asn Thr Ser Met Thr Leu Asn Asn
            20                  25                  30

Gly Gly Ala Phe Ser Ala Ser Trp Asn Asn Ile Gly Asn Ala Leu Phe
        35                  40                  45

Arg Lys Gly Lys Lys Phe Asp Ser Thr Lys Thr His His Gln Leu Gly
    50                  55                  60

Asn Ile Ser Ile Asn Tyr Asn Ala Ala Phe Asn Pro Gly Gly Asn Ser
65                  70                  75                  80

Tyr Leu Cys Val Tyr Gly Trp Thr Gln Ser Pro Leu Ala Glu Tyr Tyr
                85                  90                  95

Ile Val Glu Ser Trp Gly Thr Tyr Arg Pro Thr Gly Thr Tyr Lys Gly
            100                 105                 110

Ser Phe Tyr Ala Asp Gly Gly Thr Tyr Asp Ile Tyr Glu Thr Leu Arg
        115                 120                 125

Val Asn Gln Pro Ser Ile Ile Gly Asp Ala Thr Phe Lys Gln Tyr Trp
    130                 135                 140

Ser Val Arg Gln Thr Lys Arg Thr Ser Gly Thr Val Ser Val Ser Glu
145                 150                 155                 160

His Phe Lys Lys Trp Glu Ser Leu Gly Met Pro Met Gly Lys Met Tyr
                165                 170                 175

Glu Thr Ala Leu Thr Val Glu Gly Tyr Arg Ser Ala Gly Ser Ala Asn
            180                 185                 190
```

```
Val Met Thr Asn Gln Leu Met Ile Arg
        195                 200


<210> SEQ ID NO 32
<211> LENGTH: 172
<212> TYPE: DNA
<213> ORGANISM: Artificial Sequence
<220> FEATURE:
<223> OTHER INFORMATION: Yl_565cp core promoter

<400> SEQUENCE: 32

cctctgcttg caatgaagct gtgggtggag taaacggtgc cgcttaatac agggatggtg     60

cgtgagatag gagatttgga gccgtctact ctgtcggcca acgacataaa tagaccccct    120

cagtcacctt agacacagca gaattccacc agatcagctt ccttaattaa tc            172


<210> SEQ ID NO 33
<211> LENGTH: 162
<212> TYPE: DNA
<213> ORGANISM: Artificial Sequence
<220> FEATURE:
<223> OTHER INFORMATION: Yl_242cp core promoter

<400> SEQUENCE: 33

cattagcttg ttgacaaaac cttatgcgtc gcagagcata tacgctcgga agcctacccc     60

gtcacctccg tgacatgatg taactccttt actatatata gacgtgtgtt cgtatcgaaa    120

atagccagac actctttgct ccatcactca catttaaata ca                       162


<210> SEQ ID NO 34
<211> LENGTH: 107
<212> TYPE: DNA
<213> ORGANISM: Artificial Sequence
<220> FEATURE:
<223> OTHER INFORMATION: Yl_205cp core promoter

<400> SEQUENCE: 34

agtgtacttt ttgggacggg cagtagcaat cgtgggcgga gaccccggtg tatataaagg     60

ggtggagagg acggattatt agcaccaaca cacacactta attaaca                  107


<210> SEQ ID NO 35
<211> LENGTH: 141
<212> TYPE: DNA
<213> ORGANISM: Artificial Sequence
<220> FEATURE:
<223> OTHER INFORMATION: Yl_TEF1cp core promoter

<400> SEQUENCE: 35

tgctttgtgg ttgggacttt agccaagggt ataaaagacc accgtccccg aattaccttt     60

cctcttcttt tctctctctc cttgtcaact cacacccgaa atcgttaagc atttccttct    120

gagtataaga atttaaatac a                                              141


<210> SEQ ID NO 36
<211> LENGTH: 110
<212> TYPE: DNA
<213> ORGANISM: Artificial Sequence
<220> FEATURE:
<223> OTHER INFORMATION: Yl_137cp core promoter

<400> SEQUENCE: 36

caagtctggg cacgtccact agccacaaca cgagaacgag taacaatata tataatggag     60

attgattgtg gatcctagag aacaacaacc gtctcacaac tttaattaaa               110
```

<210> SEQ ID NO 37
<211> LENGTH: 154
<212> TYPE: DNA
<213> ORGANISM: Artificial Sequence
<220> FEATURE:
<223> OTHER INFORMATION: Yl_113cp core promoter

<400> SEQUENCE: 37
gggtcacccg catgtgtgca caaccctcca aactcaatct ctcacttata tatacaagac 60
caccgtcgcc agccaaaccc ctttctcttc tcttttttcc ttcttctttc tagataaggt 120
ccgacctaaa aacacatttc gaattaatta aaca 154

<210> SEQ ID NO 38
<211> LENGTH: 149
<212> TYPE: DNA
<213> ORGANISM: Artificial Sequence
<220> FEATURE:
<223> OTHER INFORMATION: Yl_697cp core promoter

<400> SEQUENCE: 38
tcttgtaggc ccgataaaca ccccacgcga ttagagccag gcagctaaga tataaaggtg 60
agccatcccg caactagacc cctcctccaa acgacaccag tcacgacact gacaccaagc 120
gcagtcgcaa cccttacact taattaaac 149

<210> SEQ ID NO 39
<211> LENGTH: 114
<212> TYPE: DNA
<213> ORGANISM: Artificial Sequence
<220> FEATURE:
<223> OTHER INFORMATION: Cc_RAScp core promoter

<400> SEQUENCE: 39
tcgccaccgc tcaactcgca cccaacaatg ccctccactt tatcccatcc taataaacca 60
accccatcgt cattcccttc atcgtttgga cctccaacag actattaatt aatc 114

<210> SEQ ID NO 40
<211> LENGTH: 138
<212> TYPE: DNA
<213> ORGANISM: Artificial Sequence
<220> FEATURE:
<223> OTHER INFORMATION: Cc_MFScp core promoter

<400> SEQUENCE: 40
ggaagctggc tgttgaggct gttgaggctg atcggccgag cgagagaata taagtcaccc 60
caacactgcc accgccgatc acctccactc cctccactac ctcaccacta ccacctcacc 120
tcatttcatt taaataca 138

<210> SEQ ID NO 41
<211> LENGTH: 152
<212> TYPE: DNA
<213> ORGANISM: Artificial Sequence
<220> FEATURE:
<223> OTHER INFORMATION: Cc_HSP9cp core promoter

<400> SEQUENCE: 41
ggctggtcaa gttgggtgca cgacagaggc gccgagacgc tgatataaag cgttgctgcg 60
gtgtgcctct cttcgtcagt ctcagtctca acaactctct ctcctctgct ctttccgcac 120
caccaccacc caccacacaa catttaaata ca 152

-continued

<210> SEQ ID NO 42
<211> LENGTH: 110
<212> TYPE: DNA
<213> ORGANISM: Artificial Sequence
<220> FEATURE:
<223> OTHER INFORMATION: Cc_GSTcp core promoter

<400> SEQUENCE: 42
cctcctggcc cgtcccgcgg cccacgccgt acacgttggc ccacctctca tatattaact 60
ctgaacatct catctctact cactacgctt ctgcctctca ttaattaact 110

<210> SEQ ID NO 43
<211> LENGTH: 111
<212> TYPE: DNA
<213> ORGANISM: Artificial Sequence
<220> FEATURE:
<223> OTHER INFORMATION: Cc_AKRcp core promoter

<400> SEQUENCE: 43
cgctcaccca gagcccacct gttctcacgc cagccccagg ccgcaggctg tataaagctc 60
ttccccgtcc acttatcttt cctcccattc ttctctccca gttaattaac a 111

<210> SEQ ID NO 44
<211> LENGTH: 139
<212> TYPE: DNA
<213> ORGANISM: Artificial Sequence
<220> FEATURE:
<223> OTHER INFORMATION: Cc_FbPcp core promoter

<400> SEQUENCE: 44
cctcagccag tctcccacgc tctcacccta cccccacgca cctcccgtta taagaagccg 60
acgacgtggc taagccccca aagcctccac caccttccat ccgtctctct cttctcctac 120
taccacaact taattaatc 139